United States Patent
Quinlan et al.

(10) Patent No.: US 8,962,288 B2
(45) Date of Patent: Feb. 24, 2015

(54) METHODS FOR PRODUCING A FERMENTATION PRODUCT FROM CELLULOSIC MATERIAL IN THE PRESENCE OF A PEROXIDASE

(71) Applicant: Novozymes, Inc., Davis, CA (US)

(72) Inventors: Jason Quinlan, Albany, CA (US); Feng Xu, Davis, CA (US)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 13/861,838

(22) Filed: Apr. 12, 2013

(65) Prior Publication Data

US 2013/0203127 A1 Aug. 8, 2013

Related U.S. Application Data

(62) Division of application No. 12/638,920, filed on Dec. 15, 2009, now Pat. No. 8,426,158.

(60) Provisional application No. 61/139,373, filed on Dec. 19, 2008.

(51) Int. Cl.
*C12P 7/06* (2006.01)

(52) U.S. Cl.
USPC .......................................... 435/161; 435/165

(58) Field of Classification Search
USPC ................................................ 435/161, 165
IPC ................. C12N 1/22; C12P 7/10; Y02E 50/16
See application file for complete search history.

(56) References Cited

U.S. PATENT DOCUMENTS

| 8,148,495 | B2 * | 4/2012 | Harris et al. .................. 530/350 |
| 8,426,158 | B2 * | 4/2013 | Xu et al. ........................... 435/41 |
| 2007/0077630 | A1 * | 4/2007 | Harris et al. .................. 435/105 |

FOREIGN PATENT DOCUMENTS

| WO | 2005074656 A2 | 8/2005 |
| WO | 2008134259 A1 | 11/2008 |
| WO | 2010012579 A1 | 2/2010 |

OTHER PUBLICATIONS

Jonsson et al, 1998, Appl Microbiol Bioiechnol 49, 691-697.
Kedderis et al, 1983, J Biol Chem 258(13), 8129-8138.
Lobarzewski et al, 1985, Enzyme Microb Technol 7, 564-56.
Masaki et al, 1998, Arch Dermatol Res 290, 113-118.
Nicholls et al, 2000, Adv Inorg Chem PS006-02, 51-106.
Ramachandra et al, 1988, App Environ Microbiol 54(12), 3057-3063.
Steffen et al, 2007, Res Microbiol 158, 447-455.
Asgari et al. 1998, Canadian Journal of Chemistry 76, 1606-1615.
Goldstein et al. 1993, Free Radical Biology & Medicine 15, 435-445.
Sippola 2006, Industrial Chemistry Publication Series, 21, 1-59.

* cited by examiner

*Primary Examiner* — Ralph Gitomer
(74) *Attorney, Agent, or Firm* — Kelly Reynolds

(57) ABSTRACT

A method for production of a fermentation product from cellulosic material where a cellulosic material is saccharified with an enzyme composition in the presence of a peroxide-generating system and a polypeptide having peroxidase activity, the resultant saccharified cellulosic material is fermented and a fermentation product is recovered. Inclusion of the polypeptide having peroxidase activity increases saccharification of the cellulosic material.

16 Claims, 3 Drawing Sheets

METHODS FOR PRODUCING A FERMENTATION PRODUCT FROM CELLULOSIC MATERIAL IN THE PRESENCE OF A PEROXIDASE

CROSS-REFERENCE TO RELATED APPLICATIONS

This application is a divisional application of U.S. application Ser. No. 12/638,920, filed Dec. 15, 2009, now U.S. Pat. No. 8,426,158, which claims the benefit of U.S. Provisional Application No. 61/139,373, filed Dec. 19, 2008, which applications are fully incorporated herein by reference.

REFERENCE TO A SEQUENCE LISTING

This application contains a Sequence Listing filed electronically by EFS, which is incorporated herein by reference.

BACKGROUND OF THE INVENTION

1. Field of the Invention

The present invention relates to methods for increasing hydrolysis of cellulosic material with an enzyme composition.

2. Description of the Related Art

Cellulose is a polymer of the simple sugar glucose linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

It is well known in the art that oxidation of biomolecules such as DNA, lipids, or protein is a significant issue in biological systems. Consequently, treatment with a peroxidase may improve the performance of cellulose-hydrolyzing enzyme systems.

Different peroxide-decomposing enzymes often have different specificities and potencies. For example, catalase is very efficient only at high levels of hydrogen peroxide (0.1 M or above) because of its high Michaelis constant, $K_m$, on this substance ($K_m$ ranges from 0.1 to 1 M: see Nicholls et al., 2001, *Advances in Inorg. Chem.* 51: 52-106; and Masaki et al., 1998, *Archives of Dermatological Research* 290: 113-118). At low peroxide levels, a peroxidase can be significantly more efficient (than catalase) to decompose the peroxide, because of the enzyme's high affinity (sub-mM ranges) for the peroxide. For example, horseradish peroxidase, an archetypical peroxidase, has a $K_m$ of 0.02 mM on hydrogen peroxide or ethyl hydroperoxide (Kedderis and Hollenberg, 1983, *J. Biol. Chem.* 258: 8129-8138), and glutathione peroxidase has a $K_m$ of 0.025-0.06 mM (Masaki et al., 1998, supra). Since many biomass conversion techniques are prone to generate low level peroxide, peroxidase may be more effective than catalase to remove the peroxide to improve cellulose hydrolysis.

The present invention provides methods for increasing hydrolysis of cellulosic materials with enzyme compositions.

SUMMARY OF THE INVENTION

The present invention relates to methods for degrading or converting a cellulosic material, comprising: treating the cellulosic material with an enzyme composition in the presence of a polypeptide having peroxidase activity.

The present invention also relates to methods for producing a fermentation product, comprising:

(a) saccharifying a cellulosic material with an enzyme composition in the presence of a polypeptide having peroxidase activity;

(b) fermenting the saccharified cellulosic material with one or more (several) fermenting microorganisms to produce the fermentation product; and (c) recovering the fermentation product from the fermentation.

The present invention further relates to methods of fermenting a cellulosic material, comprising: fermenting the cellulosic material with one or more (several) fermenting microorganisms, wherein the cellulosic material is hydrolyzed with an enzyme composition in the presence of a polypeptide having peroxidase activity.

DEFINITIONS

Figure 1:
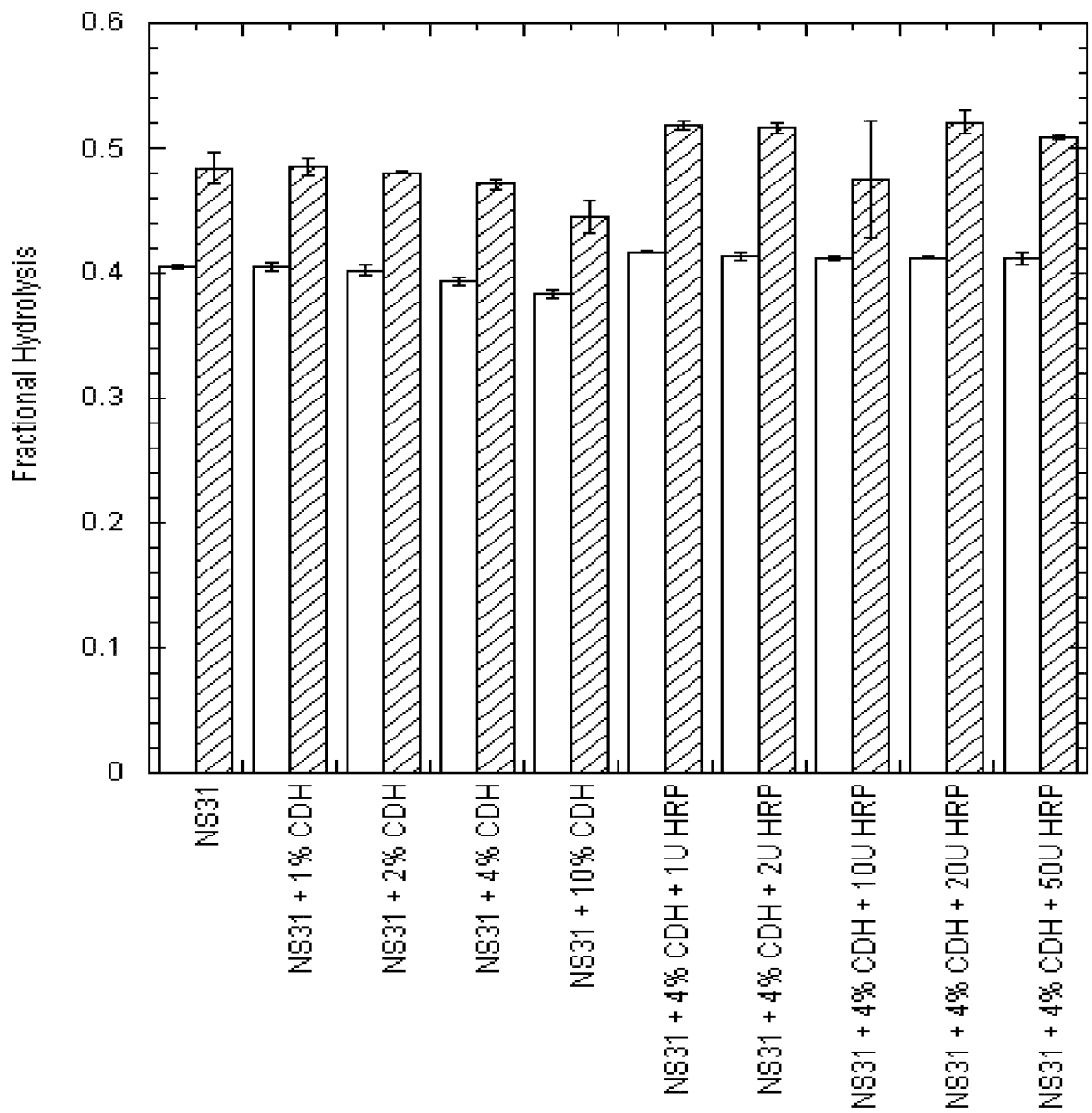
FIG. 1 shows horseradish peroxidase mitigation of cellulase-inhibition by cellobiose dehydrogenase. Fractional cellulose conversion is plotted for various reaction conditions. Solid bars: 1 day of hydrolysis; hatched bars: 3 days of hydrolysis.

Peroxide-generating system: The term "peroxide-generating system" is defined herein as either a peroxide generating enzyme as defined below, or as a chemical reaction leading to production of peroxide. Common examples of chemical methods of peroxide generation include, but are not limited to, UV-irradiation of Rose Bengal; the Reidl-Pfleiderer process of autoxidation of 2-ethyl-9,10-dihydroxyanthracene+$O_2$ to 2-ethylanthraquinone+$H_2O_2$; reaction of singlet state molecular oxygen $^1O_2$ with ascorbate; the oxidation of organic alcohols by molecular oxygen in the presence of various metal and metal complex catalysts; and the oxidation of unsaturated lipid by oxygen (after a radical initiation) to form lipid peroxide.

Peroxide-generating enzyme: The term "peroxide-generating enzyme" is defined herein as an donor:oxygen oxidoreductase (E.C. number 1.1.3.x) that catalyzes the reaction reduced substrate ($2e^-$)+$O_2$→oxidized substrate+$H_2O_2$, such as glucose oxidase that catalyzes the reaction glucose+$O_2$→gluconolactone+$H_2O_2$; and a donor: superoxide oxidoreductase (E.C. 1.15.1.x), such as superoxide dismutase that catalyzes the reaction $2O_2^-+2H^+$→$O_2+H_2O_2$. Other examples of peroxide-generating enzymes are provided herein. Alternatively oxidoreductases with side activities, wherein molecular oxygen can be used as electron acceptor by the enzyme, are also included within the term hydrogen-peroxide-generating enzyme. In addition to hydrogen peroxide, other peroxides may also be generated by these enzymes.

Peroxidase activity: The term "peroxidase activity" is defined herein as an enzyme activity that converts a peroxide, e.g., hydrogen peroxide, to a less oxidative species, e.g., water. It is understood herein that a polypeptide having peroxidase activity encompasses a peroxide-decomposing enzyme (defined below).

Peroxide-decomposing enzyme: The term "peroxide-decomposing enzyme" is defined herein as an donor:peroxide oxidoreductase (E.C. number 1.11.1.x) that catalyzes the reaction reduced substrate $(2e^-)$+ROOR'→oxidized substrate+ROH+R'OH; such as horseradish peroxidase that catalyzes the reaction phenol+$H_2O_2$→quinone+$H_2O$, and catalase that catalyzes the reaction $H_2O_2$+$H_2O_2$→$O_2$+$2H_2O$. In addition to hydrogen peroxide, other peroxides may also be decomposed by these enzymes.

Cellobiose dehydrogenase: The term "cellobiose dehydrogenase" is defined herein as a cellobiose:acceptor 1-oxidoreductase (E.C. 1.1.99.18) that catalyzes the conversion of cellobiose in the presence of an acceptor to cellobiono-1,5-lactone and a reduced acceptor. 2,6-Dichloroindophenol can act as acceptor, as can iron, especially $Fe(SCN)_3$, molecular oxygen, ubiquinone, or cytochrome C, and likely many other polyphenolics. Substrates of the enzyme include cellobiose, cello-oligosaccharides, lactose, and D-glucosyl-1,4-β-D-mannose, glucose, maltose, mannobiose, thiocellobiose, galactosyl-mannose, xylobiose, and xylose. Electron donors are preferably beta-1-4 dihexoses with glucose or mannose at the reducing end, though alpha-1-4 hexosides, hexoses, pentoses, and beta-1-4 pentomers have also been shown to act as substrates for these enzymes (Henriksson et al, 1998, *Biochimica et Biophysica Acta—Protein Structure and Molecular Enzymology;* 1383: 48-54; and Schou et al, 1998, *Biochem. J.* 330: 565-571).

Cellobiose dehydrogenases comprise two families, 1 and 2, differentiated by the presence of a cellulose binding motif (CBM). The 3-dimensional structure of cellobiose dehydrogenase features two globular domains, each containing one of two cofactors: a heme or a flavin. The active site lies at a cleft between the two domains. The catalytic cycle of cellobiose dehydrogenase follows an ordered sequential mechanism. Oxidation of cellobiose occurs via 2-electron transfer from cellobiose to the flavin, generating cellobiono-1,5-lactone and reduced flavin. The active FAD is regenerated by electron transfer to the heme group, leaving a reduced heme. The native state heme is regenerated by reaction with the oxidizing substrate at the second active site.

The oxidizing substrate is preferentially iron ferricyanide, cytochrome C, or an oxidized phenolic compound such as dichloroindophenol (DCIP), a substrate commonly used for colorimetric assays. Metal ions and $O_2$ are also substrates, but for most cellobiose dehydrogenases the reaction rate for these substrates is several orders of magnitude lower than that observed for iron or organic oxidants. Following cellobionolactone release, the product may undergo spontaneous ring-opening to generate cellobionic acid (Hallberg et al., 2003, *J. Biol. Chem.* 278: 7160-7166).

Cellulolytic activity: The term "cellulolytic activity" is defined herein as a biological activity that hydrolyzes a cellulosic material. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic activity is determined by measuring the increase in hydrolysis of a cellulosic material by cellulolytic enzyme(s) under the following conditions: 1-20 mg of cellulolytic protein/g of cellulose in PCS for 3-7 days at 50-65° C. compared to a control hydrolysis without addition of cellulolytic protein. Typical conditions are 1 ml reactions, washed or unwashed PCS, 5% insoluble solids, 50 mM sodium acetate pH 5, 1 mM $MnSO_4$, 50-65° C., 72 hours, sugar analysis by AMINEX® HPX-87H column (Bio-Rad Laboratories, Inc., Hercules, Calif., USA).

Endoglucanase: The term "endoglucanase" is defined herein as an endo-1,4-(1,3;1,4)-beta-D-glucan 4-glucanohydrolase (E.C. 3.2.1.4), which catalyses endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined based on a reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) hydrolysis according to the procedure of Ghose, 1987, *Pure and Appl. Chem.* 59: 257-268.

Cellobiohydrolase: The term "cellobiohydrolase" is defined herein as a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). For purposes of the present invention, cellobiohydrolase activity is determined using a fluorescent disaccharide derivative 4-methylumbelliferyl-β-D-lactoside according to the procedures described by van Tilbeurgh et al., 1982, FEBS Letters 149: 152-156 and van Tilbeurgh and Claeyssens, 1985, FEBS Letters 187: 283-288.

Beta-glucosidase: The term "beta-glucosidase" is defined herein as a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase activity is defined as 1.0 μmole of p-nitrophenol produced per minute at 40° C., pH 5 from 1 mM p-nitrophenyl-beta-D-glucopyranoside as substrate in 100 mM sodium citrate containing 0.01% TWEEN® 20.

Cellulolytic enhancing activity: The term "cellulolytic enhancing activity" is defined herein as a biological activity that enhances the hydrolysis of a cellulosic material by polypeptides having cellulolytic activity. For purposes of the present invention, cellulolytic enhancing activity is determined by measuring the increase in reducing sugars or the increase of the total of cellobiose and glucose from the hydrolysis of a cellulosic material by cellulolytic protein under the following conditions: 1-50 mg of total protein/g of cellulose in PCS, wherein total protein is comprised of 50-99.5% w/w cellulolytic protein and 0.5-50% w/w protein of cellulolytic enhancing activity for 1-7 day at 50-65° C. compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes A/S, Bagsærd, Denmark) in the presence of 3% of total protein weight *Aspergillus oryzae* beta-glucosidase (recombinantly produced in *Aspergillus oryzae* according to WO 02/095014) or 3% of total protein weight *Aspergillus fumigatus* beta-glucosidase (recombinantly produced in *Aspergillus oryzae* as described in WO 2002/095014) of cellulase protein loading is used as the source of the cellulolytic activity.

The polypeptides having cellulolytic enhancing activity enhance the hydrolysis of a cellulosic material catalyzed by proteins having cellulolytic activity by reducing the amount of cellulolytic enzyme required to reach the same degree of hydrolysis preferably at least 1.01-fold, more preferably at least 1.05-fold, more preferably at least 1.10-fold, more preferably at least 1.25-fold, more preferably at least 1.5-fold, more preferably at least 2-fold, more preferably at least 3-fold, more preferably at least 4-fold, more preferably at least 5-fold, even more preferably at least 10-fold, and most preferably at least 20-fold.

Family 61 glycoside hydrolase: The term "Family 61 glycoside hydrolase" or "Family GH61" is defined herein as a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. Presently, Henrissat lists the GH61 Family as unclassified indicating that properties such as mechanism, catalytic nucleophile/base, and catalytic proton donors are not known for polypeptides belonging to this family.

Xylan degrading activity: The terms "xylan degrading activity" or "xylanolytic activity" are defined herein as a biological activity that hydrolyzes xylan-containing material. The two basic approaches for measuring xylanolytic activity include: (1) measuring the total xylanolytic activity, and (2) measuring the individual xylanolytic activities (endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune*, FEBS Letters 580 (19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase activity: The term "xylanase activity" is defined herein as a 1,4-beta-D-xylan-xylohydrolase activity (E.C. 3.2.1.8) that catalyzes the endo-hydrolysis of 1,4-beta-D-xylosidic linkages in xylans. For purposes of the present invention, xylanase activity is determined using birchwood xylan as substrate. One unit of xylanase activity is defined as 1.0 μmole of reducing sugar (measured in glucose equivalents as described by Lever, 1972, A new reaction for colorimetric determination of carbohydrates, *Anal. Biochem* 47: 273-279) produced per minute during the initial period of hydrolysis at 50° C., pH 5 from 2 g of birchwood xylan per liter as substrate in 50 mM sodium acetate containing 0.01% TWEEN® 20.

Beta-xylosidase activity: The term "beta-xylosidase activity" is defined herein as a beta-D-xyloside xylohydrolase (E.C. 3.2.1.37) that catalyzes the exo-hydrolysis of short beta (1→4)-xylooligosaccharides, to remove successive D-xylose residues from the non-reducing termini. For purposes of the present invention, one unit of beta-xylosidase activity is defined as 1.0 μmole of p-nitrophenol produced per minute at 40° C., pH 5 from 1 mM p-nitrophenyl-beta-D-xyloside as substrate in 100 mM sodium citrate containing 0.01% TWEEN® 20.

Acetylxylan esterase activity: The term "acetylxylan esterase activity" is defined herein as a carboxylesterase activity (EC 3.1.1.72) that catalyses the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20. One unit of acetylxylan esterase activity is defined as the amount of enzyme capable of releasing 1 μmole of p-nitrophenolate anion per minute at pH 5, 25° C.

Feruloyl esterase activity: The term "feruloyl esterase activity" is defined herein as a 4-hydroxy-3-methoxycinnamoyl-sugar hydrolase activity (EC 3.1.1.73) that catalyzes the hydrolysis of the 4-hydroxy-3-methoxycinnamoyl(feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase activity equals the amount of enzyme capable of releasing 1 μmole of p-nitrophenolate anion per minute at pH 5, 25° C.

Alpha-glucuronidase activity: The term "alpha-glucuronidase activity" is defined herein as an alpha-D-glucosiduronate glucuronohydrolase activity (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase activity equals the amount of enzyme capable of releasing 1 μmole of glucuronic or 4-O-methyl-glucuronic acid per minute at pH 5, 40° C.

Alpha-L-arabinofuranosidase activity: The term "alpha-L-arabinofuranosidase activity" is defined herein as an alpha-L-arabinofuranoside arabinofuranohydrolase activity (EC 3.2.1.55) that catalyzes the hydrolysis of terminal non-reducing alpha-L-arabinofuranoside residues in alpha-L-arabinosides. The enzyme activity acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Cellulosic material: The cellulosic material can be any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, herbaceous material, agricultural residue, forestry residue, municipal solid waste, waste paper, and pulp and paper mill residue (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is lignocellulose.

In one aspect, the cellulosic material is herbaceous material. In another aspect, the cellulosic material is agricultural residue. In another aspect, the cellulosic material is forestry residue. In another aspect, the cellulosic material is municipal solid waste. In another aspect, the cellulosic material is waste paper. In another aspect, the cellulosic material is pulp and paper mill residue.

In another aspect, the cellulosic material is corn stover. In another aspect, the cellulosic material is corn fiber. In another aspect, the cellulosic material is corn cob. In another aspect, the cellulosic material is orange peel. In another aspect, the cellulosic material is rice straw. In another aspect, the cellulosic material is wheat straw. In another aspect, the cellulosic material is switch grass. In another aspect, the cellulosic material is miscanthus. In another aspect, the cellulosic material is bagasse.

In another aspect, the cellulosic material is microcrystalline cellulose. In another aspect, the cellulosic material is bacterial cellulose. In another aspect, the cellulosic material is algal cellulose. In another aspect, the cellulosic material is cotton linter. In another aspect, the cellulosic material is amorphous phosphoric-acid treated cellulose. In another aspect, the cellulosic material is filter paper.

The cellulosic material may be used as is or may be subjected to pretreatment, using conventional methods known in the art, as described herein. In a preferred aspect, the cellulosic material is pretreated.

Pretreated corn stover: The term "PCS" or "Pretreated Corn Stover" is defined herein as a cellulosic material derived from corn stover by treatment with heat and dilute sulfuric acid.

Xylan-containing material: The term "xylan-containing material" is defined herein as any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the methods of the present invention, any material containing xylan may be used. In a preferred aspect, the xylan-containing material is lignocellulose.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 97% pure, more preferably at least 98% pure, even more preferably at least 99% pure, most preferably at least 99.5% pure, and even most preferably 100% pure by weight of the total polypeptide material present in the preparation. The polypeptides are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Mature polypeptide: The term "mature polypeptide" is defined herein as a polypeptide in its final form following translation and any post-translational modifications, such as N-terminal processing, C-terminal truncation, glycosylation, phosphorylation, etc.

Mature polypeptide coding sequence: The term "mature polypeptide coding sequence" is defined herein as a nucleotide sequence that encodes a mature polypeptide.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Homologous sequence: The term "homologous sequence" is defined herein as a predicted protein having an E value (or expectancy score) of less than 0.001 in a tfasty search (Pearson, W. R., 1999, in *Bioinformatics Methods and Protocols*, S. Misener and S. A. Krawetz, ed., pp. 185-219) with a polypeptide of interest.

Polypeptide fragment: The term "polypeptide fragment" is defined herein as a polypeptide having one or more (several) amino acids deleted from the amino and/or carboxyl terminus of a mature polypeptide or a homologous sequence thereof, wherein the fragment has biological activity.

Subsequence: The term "subsequence" is defined herein as a nucleotide sequence having one or more (several) nucleotides deleted from the 5' and/or 3' end of a mature polypeptide coding sequence or a homologous sequence thereof, wherein the subsequence encodes a polypeptide fragment having biological activity.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99% pure, and even most preferably at least 99.5% pure by weight. The polynucleotides are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

cDNA: The term "cDNA" is defined herein as a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence.

Control sequences: The term "control sequences" is defined herein to include all components necessary for the expression of a polynucleotide encoding a polypeptide. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Expression: The term "expression" includes any step involved in the production of a polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

Modification: The term "modification" means herein any chemical modification of a polypeptide, as well as genetic manipulation of the DNA encoding the polypeptide. The modification can be a substitution, a deletion and/or an insertion of one or more (several) amino acids as well as replacements of one or more (several) amino acid side chains.

Artificial variant: When used herein, the term "artificial variant" means a polypeptide produced by an organism expressing a modified polynucleotide sequence encoding a polypeptide variant. The modified nucleotide sequence is obtained through human intervention by modification of the polynucleotide sequence.

DETAILED DESCRIPTION OF THE INVENTION

The present invention relates to methods for degrading or converting a cellulosic material, comprising: treating the cellulosic material with an enzyme composition in the presence of a polypeptide having peroxidase activity. In one aspect, the method further comprises recovering the degraded or converted cellulosic material.

The present invention also relates to methods for producing a fermentation product, comprising: (a) saccharifying a cellulosic material with an enzyme composition in the presence of a polypeptide having peroxidase activity; (b) fermenting the saccharified cellulosic material with one or more (several) fermenting microorganisms to produce the fermentation product; and (c) recovering the fermentation product from the fermentation.

The present invention further relates to methods of fermenting a cellulosic material, comprising: fermenting the cellulosic material with one or more (several) fermenting microorganisms, wherein the cellulosic material is hydrolyzed with an enzyme composition in the presence of a polypeptide having peroxidase activity. In one aspect, the fermenting of the cellulosic material produces a fermentation product. In another aspect, the method further comprises recovering the fermentation product from the fermentation.

In each of the methods described above, the presence of the polypeptide having peroxidase activity increases the hydrolysis of the cellulosic material compared to the absence of the polypeptide having peroxidase activity.

Preferably, the $K_m$ of the peroxide-decomposing enzyme or peroxidase is in the range of preferably 0.0001 to 50 mM, more preferably 0.001 to 10 mM, even more preferably 0.005 to 1 mM, and most preferably 0.01 to 0.1 mM. In one aspect, the $K_m$ of the peroxide-decomposing enzyme or peroxidase is in the range of 0.0001 to 50 mM. In another aspect, the $K_m$ of the peroxide-decomposing enzyme or peroxidase is in the range of 0.001 to 10 mM. In another aspect, the $K_m$ of the peroxide-decomposing enzyme or peroxidase is in the range of 0.005 to 1 mM. In another aspect, the $K_m$ of the peroxide-decomposing enzyme or peroxidase is in the range of 0.01 to 0.1 mM.

In one aspect, in each of the methods described above, the enzyme composition further comprises a peroxide-generating system. In another aspect, the cellulosic material comprises a peroxide-generating system. The presence of the peroxide-generating system and the polypeptide having peroxidase activity increases the hydrolysis of the cellulosic material compared to the presence of the peroxide-generating system and the absence of the polypeptide having peroxidase activity.

In another aspect, the peroxide-generating system is a hydrogen peroxide-generating enzyme.

The methods of the present invention can be used to saccharify a cellulosic material to fermentable sugars and convert the fermentable sugars to many useful substances, e.g., fuel, potable ethanol, and/or fermentation products (e.g., acids, alcohols, ketones, gases, and the like). The production of a desired fermentation product from cellulosic material typically involves pretreatment, enzymatic hydrolysis (saccharification), and fermentation.

The processing of cellulosic material according to the present invention can be accomplished using processes conventional in the art. Moreover, the methods of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and cofermentation (SSCF); hybrid hydrolysis and fermentation (HHF); separate hydrolysis and co-fermentation (SHCF); hybrid hydrolysis and fermentation (HHCF); and direct microbial conversion (DMC). SHF uses separate process steps to first enzymatically hydrolyze cellulosic material to fermentable sugars, e.g., glucose, cellobiose, cellotriose, and pentose sugars, and then ferment the fermentable sugars to ethanol. In SSF, the enzymatic hydrolysis of cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the cofermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the methods of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include: fluidized bed, upflow blanket, immobilized, and extruder type reactors for hydrolysis and/or fermentation.

Pretreatment. In practicing the methods of the present invention, any pretreatment process known in the art can be used to disrupt plant cell wall components of cellulosic material (Chandra et al., 2007, Substrate pretreatment: The key to effective enzymatic hydrolysis of lignocellulosics? *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, pre-soaking, wetting, washing, or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, cellulosic material is heated to disrupt the plant cell wall components, including lignin, hemicellulose, and cellulose to make the cellulose and other fractions, e.g., hemicellulose, accessible to enzymes. Cellulosic material is passed to or through a reaction vessel where steam is injected to increase the temperature to the required temperature and pressure and is retained therein for the desired reaction time. Steam pretreatment is preferably done at 140-230° C., more preferably 160-200° C., and most preferably 170-190° C., where the optimal temperature range depends on any addition of a chemical catalyst. Residence time for the steam pretreatment is preferably 1-15 minutes, more preferably 3-12 minutes, and most preferably 4-10 minutes, where the optimal residence time depends on temperature range and any addition of a chemical catalyst. Steam pretreatment allows for relatively high solids loadings, so that cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

A catalyst such as $H_2SO_4$ or $SO_2$ (typically 0.3 to 3% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762).

Chemical Pretreatment: The term "chemical treatment" refers to any chemical pretreatment that promotes the separation and/or release of cellulose, hemicellulose, and/or lignin. Examples of suitable chemical pretreatment processes include, for example, dilute acid pretreatment, lime pretreatment, wet oxidation, ammonia fiber/freeze explosion (AFEX), ammonia percolation (APR), and organosolv pretreatments.

In dilute acid pretreatment, cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, lime pretreatment, wet oxidation, ammonia percolation (APR), and ammonia fiber/freeze explosion (AFEX).

Lime pretreatment is performed with calcium carbonate, sodium hydroxide, or ammonia at low temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/11899, WO 2006/11900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed at preferably 1-40% dry matter, more preferably 2-30% dry matter, and most preferably 5-20% dry matter, and often the initial pH is increased by the addition of alkali such as sodium carbonate.

A modification of the wet oxidation pretreatment method, known as wet explosion (combination of wet oxidation and steam explosion), can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating cellulosic material with liquid or gaseous ammonia at moderate temperatures such as 90-100° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). AFEX pretreatment results in the depolymerization of cellulose and partial hydrolysis of hemicellulose. Lignin-carbohydrate complexes are cleaved.

Organosolv pretreatment delignifies cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose is removed.

Other examples of suitable pretreatment methods are described by Schell et al., 2003, *Appl. Biochem. and Biotechnol. Vol.* 105-108, p. 69-85, and Mosier et al., 2005, *Bioresource Technology* 96: 673-686, and U.S. Published Application 2002/0164730.

In one aspect, the chemical pretreatment is preferably carried out as an acid treatment, and more preferably as a continuous dilute and/or mild acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, more preferably 1-4, and most preferably 1-3. In one aspect, the acid concentration is in the range from preferably 0.01 to 20 wt % acid, more preferably 0.05 to 10 wt % acid, even more preferably 0.1 to 5 wt % acid, and most preferably 0.2 to 2.0 wt % acid. The acid is contacted with cellulosic material and held at a temperature in the range of preferably 160-220° C., and more preferably 165-195° C., for periods ranging from seconds to minutes to, e.g., 1 second to 60 minutes.

In another aspect, pretreatment is carried out as an ammonia fiber explosion step (AFEX pretreatment step).

In another aspect, pretreatment takes place in an aqueous slurry. In preferred aspects, cellulosic material is present during pretreatment in amounts preferably between 10-80 wt %, more preferably between 20-70 wt %, and most preferably between 30-60 wt %, such as around 50 wt %. The pretreated cellulosic material can be unwashed or washed using any method known in the art, e.g., washed with water.

Mechanical Pretreatment: The term "mechanical pretreatment" refers to various types of grinding or milling (e.g., dry milling, wet milling, or vibratory ball milling).

Physical Pretreatment: The term "physical pretreatment" refers to any pretreatment that promotes the separation and/or release of cellulose, hemicellulose, and/or lignin from cellulosic material. For example, physical pretreatment can involve irradiation (e.g., microwave irradiation), steaming/steam explosion, hydrothermolysis, and combinations thereof.

Physical pretreatment can involve high pressure and/or high temperature (steam explosion). In one aspect, high pressure means pressure in the range of preferably about 300 to about 600 psi, more preferably about 350 to about 550 psi, and most preferably about 400 to about 500 psi, such as around 450 psi. In another aspect, high temperature means temperatures in the range of about 100 to about 300° C., preferably about 140 to about 235° C. In a preferred aspect, mechanical pretreatment is performed in a batch-process, steam gun hydrolyzer system that uses high pressure and high temperature as defined above, e.g., a Sunds Hydrolyzer available from Sunds Defibrator AB, Sweden.

Combined Physical and Chemical Pretreatment: Cellulosic material can be pretreated both physically and chemically. For instance, the pretreatment step can involve dilute or mild acid treatment and high temperature and/or pressure treatment. The physical and chemical pretreatments can be carried out sequentially or simultaneously, as desired. A mechanical pretreatment can also be included.

Accordingly, in a preferred aspect, cellulosic material is subjected to mechanical, chemical, or physical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from cellulosic material. Biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., *ACS Symposium Series* 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification. In the hydrolysis step, also known as saccharification, the pretreated cellulosic material is hydrolyzed to break down cellulose and alternatively also hemicellulose to fermentable sugars, such as glucose, cellobiose, xylose, xylulose, arabinose, mannose, galactose, and/or soluble oligosaccharides. The hydrolysis is performed enzymatically by an enzyme composition in the presence of a polypeptide having peroxidase activity of the present invention. The composition can further comprise one or more (several) hemicellulolytic enzymes. The enzymes of the compositions can also be added sequentially.

Enzymatic hydrolysis is preferably carried out in a suitable aqueous environment under conditions that can be readily determined by one skilled in the art. In a preferred aspect, hydrolysis is performed under conditions suitable for the activity of the enzyme(s), i.e., optimal for the enzyme(s). The hydrolysis can be carried out as a fed batch or continuous process where the pretreated cellulosic material (substrate) is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 96 hours, more preferably about 16 to about 72 hours, and most preferably about 24 to about 48 hours. The temperature is in the range of preferably about 25° C. to about 70° C., more preferably about 30° C. to about 65° C., and more preferably about 40° C. to 60° C., in particular about 50° C. The pH is in the range of preferably about 3 to about 8, more preferably about 3.5 to about 7, and most preferably about 4 to about 6, in particular about pH 5. The dry solids content is in the range of preferably about 5 to about 50 wt %, more preferably about 10 to about 40 wt %, and most preferably about 20 to about 30 wt %.

The optimum amounts of the enzymes and polypeptides having cellulolytic enhancing activity depend on several factors including, but not limited to, the mixture of component cellulolytic enzymes, the cellulosic substrate, the concentration of cellulosic substrate, the pretreatment(s) of the cellulosic substrate, temperature, time, pH, and inclusion of fermenting organism (e.g., yeast for Simultaneous Saccharification and Fermentation).

In a preferred aspect, an effective amount of cellulolytic enzyme(s) to cellulosic material is about 0.5 to about 50 mg, preferably at about 0.5 to about 40 mg, more preferably at about 0.5 to about 25 mg, more preferably at about 0.75 to about 20 mg, more preferably at about 0.75 to about 15 mg, even more preferably at about 0.5 to about 10 mg, and most preferably at about 2.5 to about 10 mg per g of cellulosic material.

In another preferred aspect, an effective amount of a polypeptide having peroxidase activity to cellulosic material is about 0.001 to about 50 mg, preferably at about 0.01 to about 40 mg, more preferably at about 0.02 to about 25 mg, more preferably at about 0.03 to about 20 mg, more preferably at about 0.04 to about 15 mg, even more preferably at about 0.04 to about 10 mg, and most preferably at about 0.05 to about 5 mg per g of cellulosic material.

In another preferred aspect, an effective amount of polypeptide(s) having cellulolytic enhancing activity to cellulosic material is about 0.01 to about 50.0 mg, preferably about 0.01 to about 40 mg, more preferably about 0.01 to about 30 mg, more preferably about 0.01 to about 20 mg, more preferably about 0.01 to about 10 mg, more preferably about 0.01 to about 5 mg, more preferably at about 0.025 to about 1.5 mg, more preferably at about 0.05 to about 1.25 mg, more preferably at about 0.075 to about 1.25 mg, more preferably at about 0.1 to about 1.25 mg, even more preferably at about 0.15 to about 1.25 mg, and most preferably at about 0.25 to about 1.0 mg per g of cellulosic material.

In another preferred aspect, an effective amount of a polypeptide having peroxidase activity to a hydrogen peroxide-generating enzyme is about 0.005 to about 1.0 g, preferably at about 0.01 to about 1.0 g, more preferably at about 0.15 to about 0.75 g, more preferably at about 0.15 to about 0.5 g, more preferably at about 0.1 to about 0.5 g, even more preferably at about 0.1 to about 0.5 g, and most preferably at about 0.05 to about 0.2 g per g of hydrogen peroxide-generating enzyme.

In another preferred aspect, an effective amount of polypeptide(s) having cellulolytic enhancing activity to cellulolytic protein(s) is about 0.005 to about 1.0 g, preferably at about 0.01 to about 1.0 g, more preferably at about 0.15 to about 0.75 g, more preferably at about 0.15 to about 0.5 g, more preferably at about 0.1 to about 0.5 g, even more preferably at about 0.1 to about 0.5 g, and most preferably at about 0.05 to about 0.2 g per g of cellulolytic protein(s).

Fermentation. The fermentable sugars obtained from the pretreated and hydrolyzed cellulosic material can be fermented by one or more (several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be $C_6$ and/or $C_5$ fermenting organisms, or a combination thereof. Both $C_6$ and $C_5$ fermenting organisms are well known in the art. Suitable fermenting microorganisms are able to ferment, i.e., convert, sugars, such as glucose, xylose, xylulose, arabinose, maltose, mannose, galactose, or oligosaccharides, directly or indirectly into the desired fermentation product.

Examples of bacterial and fungal fermenting organisms producing ethanol are described by Lin et al., 2006, *Appl. Microbiol. Biotechnol.* 69: 627-642.

Examples of fermenting microorganisms that can ferment $C_6$ sugars include bacterial and fungal organisms, such as yeast. Preferred yeast includes strains of the *Saccharomyces* spp., preferably *Saccharomyces cerevisiae*.

Examples of fermenting organisms that can ferment $C_5$ sugars include bacterial and fungal organisms, such as yeast. Preferred $C_5$ fermenting yeast include strains of *Pichia*, preferably *Pichia stipitis*, such as *Pichia stipitis* CBS 5773; strains of *Candida*, preferably *Candida boidinii*, *Candida brassicae*, *Candida sheatae*, *Candida diddensii*, *Candida pseudotropicalis*, or *Candida utilis*.

Other fermenting organisms include strains of *Zymomonas*, such as *Zymomonas mobilis*; *Hansenula*, such as *Hansenula anomala*; *Kluyveromyces*, such as *K. fragilis*; *Schizosaccharomyces*, such as *S. pombe*; and *E. coli*, especially *E. coli* strains that have been genetically modified to improve the yield of ethanol.

In a preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*. In another preferred aspect, the yeast is a *Kluyveromyces*. In another more preferred aspect, the yeast is *Kluyveromyces marxianus*. In another more preferred aspect, the yeast is *Kluyveromyces fragilis*. In another preferred aspect, the yeast is a *Candida*. In another more preferred aspect, the yeast is *Candida boidinii*. In another more preferred aspect, the yeast is *Candida brassicae*. In another more preferred aspect, the yeast is *Candida diddensii*. In another more preferred aspect, the yeast is *Candida pseudotropicalis*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Bretannomyces*. In another more preferred aspect, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, D.C., 179-212).

Bacteria that can efficiently ferment hexose and pentose to ethanol include, for example, *Zymomonas mobilis* and *Clostridium thermocellum* (Philippidis, 1996, supra).

In a preferred aspect, the bacterium is a *Zymomonas*. In a more preferred aspect, the bacterium is *Zymomonas mobilis*. In another preferred aspect, the bacterium is a *Clostridium*. In another more preferred aspect, the bacterium is *Clostridium thermocellum*.

Commercially available yeast suitable for ethanol production includes, e.g., ETHANOL RED™ yeast (available from Fermentis/Lesaffre, USA), FALI™ (available from Fleischmann's Yeast, USA), SUPERSTART™ and THERMO-SACC™ fresh yeast (available from Ethanol Technology, WI, USA), BIOFERM™ AFT and XR (available from NABC—North American Bioproducts Corporation, GA, USA), GERT STRAND™ (available from Gert Strand AB, Sweden), and FERMIOL™ (available from DSM Specialties).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (cofermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis*, *Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Saccharomyces cerevisiae*. In another preferred aspect, the genetically modified fermenting microorganism is *Zymomonas mobilis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces* sp.

It is well known in the art that the organisms described above can also be used to produce other substances, as described herein.

The fermenting microorganism is typically added to the degraded lignocellulose or hydrolysate and the fermentation is performed for about 8 to about 96 hours, such as about 24 to about 60 hours. The temperature is typically between about 26° C. to about 60° C., in particular about 32° C. or 50° C., and at about pH 3 to about pH 8, such as around pH 4-5, 6, or 7.

In a preferred aspect, the yeast and/or another microorganism is applied to the degraded cellulosic material and the fermentation is performed for about 12 to about 96 hours, such as typically 24-60 hours. In a preferred aspect, the temperature is preferably between about 20° C. to about 60° C., more preferably about 25° C. to about 50° C., and most preferably about 32° C. to about 50° C., in particular about 32° C. or 50° C., and the pH is generally from about pH 3 to about pH 7, preferably around pH 4-7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K.

Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the methods of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products: A fermentation product can be any substance derived from the fermentation. The fermentation product can be, without limitation, an alcohol (e.g., arabinitol, butanol, ethanol, glycerol, methanol, 1,3-propanediol, sorbitol, and xylitol); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); a ketone (e.g., acetone); an amino acid (e.g., aspartic acid, glutamic acid, glycine, lysine, serine, and threonine); and a gas (e.g., methane, hydrogen ($H_2$), carbon dioxide ($CO_2$), and carbon monoxide (CO)). The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is arabinitol. In another more preferred aspect, the alcohol is butanol. In another more preferred aspect, the alcohol is ethanol. In another more preferred aspect, the alcohol is glycerol. In another more preferred aspect, the alcohol is methanol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

Recovery. The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Polypeptides Having Cellulolytic Enhancing Activity and Polynucleotides Thereof In the methods of the present invention, any polypeptide having cellulolytic enhancing activity can be used.

In a first aspect, the polypeptide having cellulolytic enhancing activity comprises the following motifs:

[ILMV]-P-X(4,5)-G-X-Y-[ILMV]-X-R-X-[EQ]-X(4)-[HNQ] and [FW]-[TF]-K-[AIV], wherein X is any amino acid, X(4,5) is any amino acid at 4 or 5 contiguous positions, and X(4) is any amino acid at 4 contiguous positions.

The polypeptide comprising the above-noted motifs may further comprise:

H-X(1,2)-G-P-X(3)-[YW]-[AILMV],

[EQ]-X-Y-X(2)-C-X-[EHQN]-[FILV]-X-[ILV], or P H-X (1,2)-G-P-X(3)-[YW]-[AILMV] and [EQ]-X-Y-X(2)-C-X-[EHQN]-[FILV]-X-[ILV], wherein X is any amino acid, X(1,2) is any amino acid at 1 position or 2 contiguous positions, X(3) is any amino acid at 3 contiguous positions, and X(2) is any amino acid at 2 contiguous positions. In the above motifs, the accepted IUPAC single letter amino acid abbreviation is employed.

In a preferred aspect, the polypeptide having cellulolytic enhancing activity further comprises H-X(1,2)-G-P-X(3)-[YW]-[AILMV]. In another preferred aspect, the isolated polypeptide having cellulolytic enhancing activity further comprises [EQ]-X-Y-X(2)-C-X-[EHQN]-[FILV]-X-[ILV]. In another preferred aspect, the polypeptide having cellulolytic enhancing activity further comprises H-X(1,2)-G-P-X(3)-[YW]-[AILMV] and [EQ]-X-Y-X(2)-C-X-[EHQN]-[FILV]-X-[ILV].

In a second aspect, the polypeptide having cellulolytic enhancing activity comprises the following motif:

[ILMV]-P-x(4,5)-G-x-Y-[ILMV]-x-R-x-[EQ]-x(3)-A-[HNQ], wherein x is any amino acid, x(4,5) is any amino acid at 4 or 5 contiguous positions, and x(3) is any amino acid at 3 contiguous positions. In the above motif, the accepted IUPAC single letter amino acid abbreviation is employed.

In a third aspect, the polypeptide having cellulolytic enhancing activity comprises an amino acid sequence that has a degree of identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% (hereinafter "homologous polypeptides"). In a preferred aspect, the mature polypeptide sequence is amino acids 20 to 326 of SEQ ID NO: 2, amino acids 18 to 239 of SEQ ID NO: 4, amino acids 20 to 258 of SEQ ID NO: 6, amino acids 19 to 226 of SEQ ID NO: 8, amino acids 20 to 304 of SEQ ID NO: 10, amino acids 16 to 317 of SEQ ID NO: 12, amino acids 23 to 250 of SEQ ID NO: 14, or amino acids 20 to 249 of SEQ ID NO: 16.

A polypeptide having cellulolytic enhancing activity preferably comprises the amino acid sequence of SEQ ID NO: 2 or an allelic variant thereof; or a fragment thereof that has cellulolytic enhancing activity. In a preferred aspect, the polypeptide comprises the amino acid sequence of SEQ ID NO: 2. In another preferred aspect, the polypeptide comprises the mature polypeptide of SEQ ID NO: 2. In another preferred aspect, the polypeptide comprises amino acids 20 to 326 of SEQ ID NO: 2, or an allelic variant thereof; or a fragment thereof that has cellulolytic enhancing activity. In another preferred aspect, the polypeptide comprises amino acids 20 to 326 of SEQ ID NO: 2. In another preferred aspect, the polypeptide consists of the amino acid sequence of SEQ ID NO: 2 or an allelic variant thereof; or a fragment thereof that has cellulolytic enhancing activity. In another preferred aspect, the polypeptide consists of the amino acid sequence of SEQ ID NO: 2. In another preferred aspect, the polypeptide consists of the mature polypeptide of SEQ ID NO: 2. In another preferred aspect, the polypeptide consists of amino acids 20 to 326 of SEQ ID NO: 2 or an allelic variant thereof; or a fragment thereof that has cellulolytic enhancing activity. In another preferred aspect, the polypeptide consists of amino acids 20 to 326 of SEQ ID NO: 2.

A polypeptide having cellulolytic enhancing activity preferably comprises the amino acid sequence of SEQ ID NO: 4 or an allelic variant thereof; or a fragment thereof that has cellulolytic enhancing activity. In a preferred aspect, the polypeptide comprises the amino acid sequence of SEQ ID NO: 4. In another preferred aspect, the polypeptide comprises the mature polypeptide of SEQ ID NO: 4. In another preferred aspect, the polypeptide comprises amino acids 18 to 239 of SEQ ID NO: 4, or an allelic variant thereof; or a fragment thereof that has cellulolytic enhancing activity. In another preferred aspect, the polypeptide comprises amino acids 18 to 239 of SEQ ID NO: 4. In another preferred aspect, the polypeptide consists of the amino acid sequence of SEQ ID NO: 4 or an allelic variant thereof; or a fragment thereof that has cellulolytic enhancing activity. In another preferred aspect, the polypeptide consists of the amino acid sequence of SEQ ID NO: 4. In another preferred aspect, the polypeptide consists of the mature polypeptide of SEQ ID NO: 4. In another preferred aspect, the polypeptide consists of amino acids 18 to 239 of SEQ ID NO: 4 or an allelic variant thereof; or a fragment thereof that has cellulolytic enhancing activity. In another preferred aspect, the polypeptide consists of amino acids 18 to 239 of SEQ ID NO: 4.

A polypeptide having cellulolytic enhancing activity preferably comprises the amino acid sequence of SEQ ID NO: 6 or an allelic variant thereof; or a fragment thereof that has cellulolytic enhancing activity. In a preferred aspect, the polypeptide comprises the amino acid sequence of SEQ ID NO: 6. In another preferred aspect, the polypeptide comprises the mature polypeptide of SEQ ID NO: 6. In another preferred aspect, the polypeptide comprises amino acids 20 to 258 of SEQ ID NO: 6, or an allelic variant thereof; or a fragment thereof that has cellulolytic enhancing activity. In another preferred aspect, the polypeptide comprises amino acids 20 to 258 of SEQ ID NO: 6. In another preferred aspect, the polypeptide consists of the amino acid sequence of SEQ ID NO: 6 or an allelic variant thereof; or a fragment thereof that has cellulolytic enhancing activity. In another preferred aspect, the polypeptide consists of the amino acid sequence of SEQ ID NO: 6. In another preferred aspect, the polypeptide consists of the mature polypeptide of SEQ ID NO: 6. In another preferred aspect, the polypeptide consists of amino acids 20 to 258 of SEQ ID NO: 6 or an allelic variant thereof; or a fragment thereof that has cellulolytic enhancing activity. In another preferred aspect, the polypeptide consists of amino acids 20 to 258 of SEQ ID NO: 6.

A polypeptide having cellulolytic enhancing activity preferably comprises the amino acid sequence of SEQ ID NO: 8 or an allelic variant thereof; or a fragment thereof that has cellulolytic enhancing activity. In a preferred aspect, the polypeptide comprises the amino acid sequence of SEQ ID NO: 8. In another preferred aspect, the polypeptide comprises the mature polypeptide of SEQ ID NO: 8. In another preferred aspect, the polypeptide comprises amino acids 19 to 226 of SEQ ID NO: 8, or an allelic variant thereof; or a fragment thereof that has cellulolytic enhancing activity. In another preferred aspect, the polypeptide comprises amino acids 19 to 226 of SEQ ID NO: 8. In another preferred aspect, the polypeptide consists of the amino acid sequence of SEQ ID NO: 8 or an allelic variant thereof; or a fragment thereof that has cellulolytic enhancing activity. In another preferred aspect, the polypeptide consists of the amino acid sequence of SEQ ID NO: 8. In another preferred aspect, the polypeptide consists of the mature polypeptide of SEQ ID NO: 8. In another preferred aspect, the polypeptide consists of amino acids 19 to 226 of SEQ ID NO: 8 or an allelic variant thereof; or a fragment thereof that has cellulolytic enhancing activity. In another preferred aspect, the polypeptide consists of amino acids 19 to 226 of SEQ ID NO: 8.

A polypeptide having cellulolytic enhancing activity preferably comprises the amino acid sequence of SEQ ID NO: 10 or an allelic variant thereof; or a fragment thereof that has cellulolytic enhancing activity. In a preferred aspect, the polypeptide comprises the amino acid sequence of SEQ ID NO: 10. In another preferred aspect, the polypeptide comprises the mature polypeptide of SEQ ID NO: 10. In another preferred aspect, the polypeptide comprises amino acids 20 to 304 of SEQ ID NO: 10, or an allelic variant thereof; or a fragment thereof that has cellulolytic enhancing activity. In another preferred aspect, the polypeptide comprises amino acids 20 to 304 of SEQ ID NO: 10. In another preferred aspect, the polypeptide consists of the amino acid sequence of SEQ ID NO: 10 or an allelic variant thereof; or a fragment thereof that has cellulolytic enhancing activity. In another preferred aspect, the polypeptide consists of the amino acid sequence of SEQ ID NO: 10. In another preferred aspect, the polypeptide consists of the mature polypeptide of SEQ ID NO: 10. In another preferred aspect, the polypeptide consists of amino acids 20 to 304 of SEQ ID NO: 10 or an allelic variant thereof; or a fragment thereof that has cellulolytic enhancing activity. In another preferred aspect, the polypeptide consists of amino acids 20 to 304 of SEQ ID NO: 10.

A polypeptide having cellulolytic enhancing activity preferably comprises the amino acid sequence of SEQ ID NO: 12 or an allelic variant thereof; or a fragment thereof having cellulolytic enhancing activity. In a preferred aspect, the polypeptide comprises the amino acid sequence of SEQ ID NO: 12. In another preferred aspect, the polypeptide comprises the mature polypeptide of SEQ ID NO: 12. In another preferred aspect, the polypeptide comprises amino acids 16 to 317 of SEQ ID NO: 12, or an allelic variant thereof; or a fragment thereof having cellulolytic enhancing activity. In another preferred aspect, the polypeptide comprises amino acids 16 to 317 of SEQ ID NO: 12. In another preferred aspect, the polypeptide consists of the amino acid sequence of SEQ ID NO: 12 or an allelic variant thereof; or a fragment thereof having cellulolytic enhancing activity. In another preferred aspect, the polypeptide consists of the amino acid sequence of SEQ ID NO: 12. In another preferred aspect, the polypeptide consists of the mature polypeptide of SEQ ID NO: 12. In another preferred aspect, the polypeptide consists of amino acids 16 to 317 of SEQ ID NO: 12 or an allelic variant thereof; or a fragment thereof having cellulolytic enhancing activity. In another preferred aspect, the polypeptide consists of amino acids 16 to 317 of SEQ ID NO: 12.

A polypeptide having cellulolytic enhancing activity preferably comprises the amino acid sequence of SEQ ID NO: 14 or an allelic variant thereof; or a fragment thereof that has cellulolytic enhancing activity. In a preferred aspect, the polypeptide comprises the amino acid sequence of SEQ ID NO: 14. In another preferred aspect, the polypeptide comprises the mature polypeptide of SEQ ID NO: 14. In another preferred aspect, the polypeptide comprises amino acids 23 to 250 of SEQ ID NO: 14, or an allelic variant thereof; or a fragment thereof that has cellulolytic enhancing activity. In another preferred aspect, the polypeptide comprises amino acids 23 to 250 of SEQ ID NO: 14. In another preferred aspect, the polypeptide consists of the amino acid sequence of SEQ ID NO: 14 or an allelic variant thereof; or a fragment thereof that has cellulolytic enhancing activity. In another preferred aspect, the polypeptide consists of the amino acid sequence of SEQ ID NO: 14. In another preferred aspect, the polypeptide consists of the mature polypeptide of SEQ ID NO: 14. In another preferred aspect, the polypeptide consists of amino acids 23 to 250 of SEQ ID NO: 14 or an allelic variant thereof; or a fragment thereof that has cellulolytic enhancing activity. In another preferred aspect, the polypeptide consists of amino acids 23 to 250 of SEQ ID NO: 14.

A polypeptide having cellulolytic enhancing activity preferably comprises the amino acid sequence of SEQ ID NO: 16 or an allelic variant thereof; or a fragment thereof that has cellulolytic enhancing activity. In a preferred aspect, the polypeptide comprises the amino acid sequence of SEQ ID NO: 16. In another preferred aspect, the polypeptide comprises the mature polypeptide of SEQ ID NO: 16. In another preferred aspect, the polypeptide comprises amino acids 20 to 249 of SEQ ID NO: 16, or an allelic variant thereof; or a fragment thereof that has cellulolytic enhancing activity. In another preferred aspect, the polypeptide comprises amino acids 20 to 249 of SEQ ID NO: 16. In another preferred aspect, the polypeptide consists of the amino acid sequence of SEQ ID NO: 16 or an allelic variant thereof; or a fragment thereof that has cellulolytic enhancing activity. In another preferred aspect, the polypeptide consists of the amino acid sequence of SEQ ID NO: 16. In another preferred aspect, the polypeptide consists of the mature polypeptide of SEQ ID NO: 16. In another preferred aspect, the polypeptide consists of amino acids 20 to 249 of SEQ ID NO: 16 or an allelic variant thereof; or a fragment thereof that has cellulolytic enhancing activity. In another preferred aspect, the polypeptide consists of amino acids 20 to 249 of SEQ ID NO: 16.

Preferably, a fragment of the mature polypeptide of SEQ ID NO: 2 contains at least 277 amino acid residues, more preferably at least 287 amino acid residues, and most preferably at least 297 amino acid residues. Preferably, a fragment of the mature polypeptide of SEQ ID NO: 4 contains at least 185 amino acid residues, more preferably at least 195 amino acid residues, and most preferably at least 205 amino acid residues. Preferably, a fragment of the mature polypeptide of SEQ ID NO: 6 contains at least 200 amino acid residues, more preferably at least 212 amino acid residues, and most preferably at least 224 amino acid residues. Preferably, a fragment of the mature polypeptide of SEQ ID NO: 8 contains at least 175 amino acid residues, more preferably at least 185 amino acid residues, and most preferably at least 195 amino acid residues. Preferably, a fragment of the mature polypeptide of SEQ ID NO: 10 contains at least 240 amino acid residues, more preferably at least 255 amino acid residues, and most preferably at least 270 amino acid residues. Preferably, a fragment of the mature polypeptide of SEQ ID NO: 12 contains at least 255 amino acid residues, more preferably at least 270 amino acid residues, and most preferably at least 285 amino acid residues. Preferably, a fragment of the mature polypeptide of SEQ ID NO: 14 contains at least 175 amino acid residues, more preferably at least 190 amino acid residues, and most preferably at least 205 amino acid residues. Preferably, a fragment of the mature polypeptide of SEQ ID NO: 16 contains at least 200 amino acid residues, more preferably at least 210 amino acid residues, and most preferably at least 220 amino acid residues.

Preferably, a subsequence of the mature polypeptide coding sequence of SEQ ID NO: 1 contains at least 831 nucleotides, more preferably at least 861 nucleotides, and most preferably at least 891 nucleotides. Preferably, a subsequence of the mature polypeptide coding sequence of SEQ ID NO: 3 contains at least 555 nucleotides, more preferably at least 585 nucleotides, and most preferably at least 615 nucleotides. Preferably, a subsequence of the mature polypeptide coding sequence of SEQ ID NO: 5 contains at least 600 nucleotides, more preferably at least 636 nucleotides, and most preferably at least 672 nucleotides. Preferably, a subsequence of the mature polypeptide coding sequence of SEQ ID NO: 7 contains at least 525 nucleotides, more preferably at least 555 nucleotides, and most preferably at least 585 nucleotides. Preferably, a subsequence of the mature polypeptide coding sequence of SEQ ID NO: 9 contains at least 720 nucleotides, more preferably at least 765 nucleotides, and most preferably at least 810 nucleotides. Preferably, a subsequence of the mature polypeptide coding sequence of SEQ ID NO: 11 contains at least 765 nucleotides, more preferably at least 810 nucleotides, and most preferably at least 855 nucleotides Preferably, a subsequence of the mature polypeptide coding sequence of nucleotides 67 to 796 of SEQ ID NO: 13 contains at least 525 nucleotides, more preferably at least 570 nucleotides, and most preferably at least 615 nucleotides. Preferably, a subsequence of the mature polypeptide coding sequence of SEQ ID NO: 15 contains at least 600 nucleotides, more preferably at least 630 nucleotides, and most preferably at least 660 nucleotides.

In a fourth aspect, the polypeptide having cellulolytic enhancing activity is encoded by a polynucleotide that hybridizes under at least very low stringency conditions, preferably at least low stringency conditions, more preferably at least medium stringency conditions, more preferably at least medium-high stringency conditions, even more preferably at least high stringency conditions, and most preferably at least very high stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15, (ii) the cDNA sequence contained in the mature polypeptide coding sequence of SEQ ID NO: 1, SEQ ID NO: 3, SEQ ID NO: 5, or SEQ ID NO: 13, or the genomic DNA sequence comprising the mature polypeptide coding sequence of SEQ ID NO: 7, SEQ ID NO: 9, SEQ ID NO: 11, or SEQ ID NO: 15, (iii) a subsequence of (i) or (ii), or (iv) a full-length complementary strand of (i), (ii), or (iii) (J. Sambrook, E. F. Fritsch, and T. Maniatus, 1989, supra). A subsequence of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15 contains at least 100 contiguous nucleotides or preferably at least 200 contiguous nucleotides. Moreover, the subsequence may encode a polypeptide fragment that has cellulolytic enhancing activity. In a preferred aspect, the mature polypeptide coding sequence is nucleotides 388 to 1332 of SEQ ID NO: 1, nucleotides 98 to 821 of SEQ ID NO: 3, nucleotides 126 to 978 of SEQ ID NO: 5, nucleotides 55 to 678 of SEQ ID NO: 7, nucleotides 58 to 912 of SEQ ID NO: 9, nucleotides 46 to 951 of SEQ ID NO: 11, nucleotides 67 to 796 of SEQ ID NO: 13, or nucleotides 77 to 766 of SEQ ID NO: 15.

The nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15, or a subsequence thereof; as well as the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16, or a fragment thereof, may be used to design a nucleic acid probe to identify and clone DNA encoding polypeptides having cellulolytic enhancing activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are preferably at least 600 nucleotides, more preferably at least 700 nucleotides, even more preferably at least 800 nucleotides, or most preferably at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may, therefore, be screened for DNA that hybridizes with the probes described above and encodes a polypeptide having cellulolytic enhancing activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, or a subsequence thereof, the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15 the cDNA sequence contained in the mature polypeptide coding sequence of SEQ ID NO: 1, SEQ ID NO: 3, SEQ ID NO: 5, or SEQ ID NO: 13, or the genomic DNA sequence comprising the mature polypeptide coding sequence of SEQ ID NO: 7, SEQ ID NO: 9, SEQ ID NO: 11, or SEQ ID NO: 15, its full-length complementary strand, or a subsequence thereof, under very low to very high stringency conditions, as described supra.

In a preferred aspect, the nucleic acid probe is the mature polypeptide coding sequence of SEQ ID NO: 1. In another preferred aspect, the nucleic acid probe is nucleotides 388 to 1332 of SEQ ID NO: 1. In another preferred aspect, the nucleic acid probe is a polynucleotide sequence that encodes the polypeptide of SEQ ID NO: 2, or a subsequence thereof. In another preferred aspect, the nucleic acid probe is SEQ ID NO: 1. In another preferred aspect, the nucleic acid probe is the polynucleotide sequence contained in plasmid pEJG120 which is contained in *E. coli* NRRL B-30699, wherein the polynucleotide sequence thereof encodes a polypeptide having cellulolytic enhancing activity. In another preferred aspect, the nucleic acid probe is the mature polypeptide coding sequence contained in plasmid pEJG120 which is contained in *E. coli* NRRL B-30699.

In another preferred aspect, the nucleic acid probe is the mature polypeptide coding sequence of SEQ ID NO: 3. In another preferred aspect, the nucleic acid probe is nucleotides 98 to 821 of SEQ ID NO: 3. In another preferred aspect, the nucleic acid probe is a polynucleotide sequence that encodes the polypeptide of SEQ ID NO: 4, or a subsequence thereof. In another preferred aspect, the nucleic acid probe is SEQ ID NO: 3. In another preferred aspect, the nucleic acid probe is the polynucleotide sequence contained in plasmid pTter61C which is contained in *E. coli* NRRL B-30813, wherein the polynucleotide sequence thereof encodes a polypeptide having cellulolytic enhancing activity. In another preferred aspect, the nucleic acid probe is the mature polypeptide coding sequence contained in plasmid pTter61C which is contained in *E. coli* NRRL B-30813.

In another preferred aspect, the nucleic acid probe is the mature polypeptide coding sequence of SEQ ID NO: 5. In another preferred aspect, the nucleic acid probe is nucleotides 126 to 978 of SEQ ID NO: 5. In another preferred aspect, the nucleic acid probe is a polynucleotide sequence that encodes the polypeptide of SEQ ID NO: 6, or a subsequence thereof. In another preferred aspect, the nucleic acid probe is SEQ ID NO: 5. In another preferred aspect, the nucleic acid probe is the polynucleotide sequence contained in plasmid pTter61D which is contained in *E. coli* NRRL B-30812, wherein the polynucleotide sequence thereof encodes a polypeptide having cellulolytic enhancing activity. In another preferred aspect, the nucleic acid probe is the mature polypeptide coding sequence contained in plasmid pTter61D which is contained in *E. coli* NRRL B-30812.

In another preferred aspect, the nucleic acid probe is the mature polypeptide coding sequence of SEQ ID NO: 7. In another preferred aspect, the nucleic acid probe is nucleotides 55 to 678 of SEQ ID NO: 7. In another preferred aspect, the nucleic acid probe is a polynucleotide sequence that encodes the polypeptide of SEQ ID NO: 8, or a subsequence thereof. In another preferred aspect, the nucleic acid probe is SEQ ID NO: 7. In another preferred aspect, the nucleic acid probe is the polynucleotide sequence contained in plasmid pTter61E which is contained in *E. coli* NRRL B-30814, wherein the polynucleotide sequence thereof encodes a polypeptide having cellulolytic enhancing activity. In another preferred aspect, the nucleic acid probe is the mature polypeptide coding sequence contained in plasmid pTter61E which is contained in *E. coli* NRRL B-30814.

In another preferred aspect, the nucleic acid probe is the mature polypeptide coding sequence of SEQ ID NO: 9. In another preferred aspect, the nucleic acid probe is nucleotides 58 to 912 of SEQ ID NO: 9 In another preferred aspect, the nucleic acid probe is a polynucleotide sequence that encodes the polypeptide of SEQ ID NO: 10, or a subsequence thereof. In another preferred aspect, the nucleic acid probe is SEQ ID NO: 9. In another preferred aspect, the nucleic acid probe is the polynucleotide sequence contained in plasmid pTter61G which is contained in *E. coli* NRRL B-30811, wherein the polynucleotide sequence thereof encodes a polypeptide having cellulolytic enhancing activity. In another preferred aspect, the nucleic acid probe is the mature polypeptide coding sequence contained in plasmid pTter61G which is contained in *E. coli* NRRL B-30811.

In another preferred aspect, the nucleic acid probe is the mature polypeptide coding sequence of SEQ ID NO: 11. In another preferred aspect, the nucleic acid probe is nucleotides 46 to 951 of SEQ ID NO: 11. In another preferred aspect, the nucleic acid probe is a polynucleotide sequence that encodes the polypeptide of SEQ ID NO: 12, or a subsequence thereof. In another preferred aspect, the nucleic acid probe is SEQ ID NO: 11. In another preferred aspect, the nucleic acid probe is the polynucleotide sequence contained in plasmid pTter61F which is contained in *E. coli* NRRL B-50044, wherein the polynucleotide sequence thereof encodes a polypeptide having cellulolytic enhancing activity. In another preferred aspect, the nucleic acid probe is the mature polypeptide coding region contained in plasmid pTter61F which is contained in *E. coli* NRRL B-50044.

In another preferred aspect, the nucleic acid probe is the mature polypeptide coding sequence of SEQ ID NO: 13. In another preferred aspect, the nucleic acid probe is nucleotides 67 to 796 of SEQ ID NO: 13. In another preferred aspect, the nucleic acid probe is a polynucleotide sequence that encodes the polypeptide of SEQ ID NO: 14, or a subsequence thereof. In another preferred aspect, the nucleic acid probe is SEQ ID NO: 13. In another preferred aspect, the nucleic acid probe is the polynucleotide sequence contained in plasmid pDZA2-7 which is contained in *E. coli* NRRL B-30704, wherein the polynucleotide sequence thereof encodes a polypeptide having cellulolytic enhancing activity. In another preferred aspect, the nucleic acid probe is the mature polypeptide coding sequence contained in plasmid pDZA2-7 which is contained in *E. coli* NRRL B-30704.

In another preferred aspect, the nucleic acid probe is the mature polypeptide coding sequence of SEQ ID NO: 15. In another preferred aspect, the nucleic acid probe is nucleotides 77 to 766 of SEQ ID NO: 15. In another preferred aspect, the nucleic acid probe is a polynucleotide sequence that encodes the polypeptide of SEQ ID NO: 16, or a subsequence thereof. In another preferred aspect, the nucleic acid probe is SEQ ID NO: 15. In another preferred aspect, the nucleic acid probe is the polynucleotide sequence contained in plasmid pTr333 which is contained in *E. coli* NRRL B-30878, wherein the polynucleotide sequence thereof encodes a polypeptide having cellulolytic enhancing activity. In another preferred aspect, the nucleic acid probe is the mature polypeptide coding sequence contained in plasmid pTr333 which is contained in *E. coli* NRRL B-30878.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes of about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes of about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a fifth aspect, the polypeptide having cellulolytic enhancing activity is encoded by a polynucleotide comprising or consisting of a nucleotide sequence that has a degree of identity to the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%.

In a preferred aspect, the mature polypeptide coding sequence is nucleotides 388 to 1332 of SEQ ID NO: 1, nucleotides 98 to 821 of SEQ ID NO: 3, nucleotides 126 to 978 of SEQ ID NO: 5, nucleotides 55 to 678 of SEQ ID NO: 7, nucleotides 58 to 912 of SEQ ID NO: 9, nucleotides 46 to 951 of SEQ ID NO: 11, nucleotides 67 to 796 of SEQ ID NO: 13, or nucleotides 77 to 766 of SEQ ID NO: 15.

In a sixth aspect, the polypeptide having cellulolytic enhancing activity is an artificial variant comprising a substitution, deletion, and/or insertion of one or more (or several) amino acids of the mature polypeptide of SEQ ID NO: 2, SEQ ID NO: 4, SEQ ID NO: 6, SEQ ID NO: 8, SEQ ID NO: 10, SEQ ID NO: 12, or SEQ ID NO: 14, or SEQ ID NO: 16; or a homologous sequence thereof. Methods for preparing such an artificial variant is described supra.

The total number of amino acid substitutions, deletions and/or insertions of the mature polypeptide of SEQ ID NO: 2, SEQ ID NO: 4, SEQ ID NO: 6, SEQ ID NO: 8, SEQ ID NO: 10, SEQ ID NO: 12, or SEQ ID NO: 14, or SEQ ID NO: 16, is 10, preferably 9, more preferably 8, more preferably 7, more preferably at most 6, more preferably 5, more preferably 4, even more preferably 3, most preferably 2, and even most preferably 1.

A polypeptide having cellulolytic enhancing activity may be obtained from microorganisms of any genus. In a preferred aspect, the polypeptide obtained from a given source is secreted extracellularly.

A polypeptide having cellulolytic enhancing activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus,* or *Oceanobacillus* polypeptide having cellulolytic enhancing activity, or a Gram negative bacterial polypeptide such as an *E. coli, Pseudomonas, Salmonella, Campylobacter, Helicobacter, Flavobacterium, Fusobacterium, Ilyobacter, Neisseria,* or *Ureaplasma* polypeptide having cellulolytic enhancing activity.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having cellulolytic enhancing activity.

In another preferred aspect, the polypeptide is a *Streptococcus equisimilis, Streptococcus pyogenes, Streptococcus uberis,* or *Streptococcus equi* subsp. *Zooepidemicus* polypeptide having cellulolytic enhancing activity.

In another preferred aspect, the polypeptide is a *Streptomyces achromogenes, Streptomyces avermitilis, Streptomyces coelicolor, Streptomyces griseus,* or *Streptomyces lividans* polypeptide having cellulolytic enhancing activity.

The polypeptide having cellulolytic enhancing activity may also be a fungal polypeptide, and more preferably a yeast polypeptide such as a *Candida, Kluyveromyces, Pichia, Saccharomyces, Schizosaccharomyces,* or *Yarrowia* polypeptide having cellulolytic enhancing activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having cellulolytic enhancing activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having cellulolytic enhancing activity.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminun, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride,* or *Trichophaea saccata* polypeptide having cellulolytic enhancing activity.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, polypeptides having cellulolytic enhancing activity may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide encoding a polypeptide has been detected with the probe(s), the polynucleotide can be isolated or cloned by utilizing techniques that are well known to those of ordinary skill in the art (see, e.g., Sambrook et al., 1989, supra)

Polynucleotides comprising nucleotide sequences that encode polypeptide having cellulolytic enhancing activity can be isolated and utilized to express the polypeptide having cellulolytic enhancing activity for evaluation in the methods of the present invention, as described herein.

The polynucleotides comprise nucleotide sequences that have a degree of identity to the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

The polynucleotide may also be a polynucleotide encoding a polypeptide having cellulolytic enhancing activity that hybridizes under at least very low stringency conditions, preferably at least low stringency conditions, more preferably at least medium stringency conditions, more preferably at least medium-high stringency conditions, even more preferably at least high stringency conditions, and most preferably at least very high stringency conditions with (i) t the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15, (ii) the cDNA sequence contained in the mature polypeptide coding sequence of SEQ ID NO: 1, SEQ ID NO: 3, SEQ ID NO: 5, or SEQ ID NO: 13, or the genomic DNA sequence comprising the mature polypeptide coding sequence of SEQ ID NO: 7, SEQ ID NO: 9, SEQ ID NO: 11, or SEQ ID NO: 15, or (iii) a full-length complementary strand of (i) or (ii); or allelic variants and subsequences thereof (Sambrook et al., 1989, supra), as defined herein. In a preferred aspect, the mature polypeptide coding sequence is nucleotides 388 to 1332 of SEQ ID NO: 1, nucleotides 98 to 821 of SEQ ID NO: 3, nucleotides 126 to 978 of SEQ ID NO: 5, nucleotides 55 to 678 of SEQ ID NO: 7, nucleotides 58 to 912 of SEQ ID NO: 9, nucleotides 46 to 951 of SEQ ID NO: 11, nucleotides 67 to 796 of SEQ ID NO: 13, or nucleotides 77 to 766 of SEQ ID NO: 15.

As described earlier, the techniques used to isolate or clone a polynucleotide encoding a polypeptide are known in the art and include isolation from genomic DNA, preparation from cDNA, or a combination thereof.

Peroxide-Generating Enzymes

In the methods of the present invention, the peroxide-generating enzyme can be any peroxide-generating enzyme. The peroxide-generating enzyme, e.g., hydrogen peroxide-generating enzyme, may be present as an enzyme activity in the enzyme composition, a component in one or more (several) proteins added to the composition, and/or an enzyme component present in the cellulosic material. In one aspect, the peroxide is hydrogen peroxide.

Examples of peroxide-generating enzymes include the following:

E.C. 1.1.3.x—donor:oxygen oxidoreductase, glucose oxidase (E.C. 1.1.3.4), hexose oxidase (E.C. 1.1.3.5), aryl-alcohol oxidase (E.C. 1.1.3.7), D-arabinono-1,4-lactone oxidase (E.C. 1.1.3.37), vanillyl-alcohol oxidase (E.C. 1.1.3.38), xylitol oxidase (E.C. 1.1.3.41)

E.C. 1.1.99.8—alcohol dehydrogenase

E.C. 1.1.99.18—cellobiose dehydrogenase

E.C. 1.2.3.x—aldehyde oxidase (E.C. 1.2.3.1), aryl-aldehyde oxidase (E.C. 1.2.3.9)

E.C. 1.3.3.x—dihydroorotate oxidase (E.C. 1.3.3.1), pyrroloquinoline-quinone synthase (E.C. 1.3.3.11)

E.C. 1.4.3.x—L-amino acid oxidase (E.C. 1.4.3.2), L-glutamate oxidase (E.C. 1.4.3.11)

E.C. 1.5.3.x—polyamine oxidase (1.5.3.11)

E.C. 1.6.3.1—NADPH oxidase

E.C. 1.7.3.x—urate oxidase (E.C. 1.7.3.3), hydroxylamine oxidase (E.C. 1.7.3.4)

E.C. 1.8.3.x—thiol oxidase (E.C. 1.8.3.2), glutathione oxidase (E.C. 1.8.3.3)

E.C. 1.9.3.1—cytochrome c oxidase

E.C. 1.13.11.12 lipoxygenase

E.C. 1.13.11.31 arachidonate 12-lipoxygenase

E.C. 1.13.11.33 arachidonate 15-lipoxygenase

E.C. 1.13.11.34 arachidonate 5-lipoxygenase

E.C. 1.13.11.40 arachidonate 8-lipoxygenase

E.C. 1.13.11.45 linoleate 11-lipoxygenase

E.C. 1.15.1.1—superoxide dismutase

E.C. 1.17.3.x—xanthine oxidase (E.C. 1.17.3.2)

The peroxide-generating enzyme may be obtained from microorganisms of any genus. In one aspect, the polypeptide obtained from a given source is secreted extracellularly.

The peroxide-generating enzyme may be a bacterial peroxide-generating enzyme. For example, the peroxide-generating enzyme may be a gram positive bacterial peroxide-generating enzyme such as a *Bacillus, Streptococcus, Streptomyces, Staphylococcus, Enterococcus, Lactobacillus, Lactococcus, Clostridium, Geobacillus*, or *Oceanobacillus* peroxide-generating enzyme, or a Gram negative bacterial peroxide-generating enzyme such as an *E. coli, Pseudomonas, Salmonella, Campylobacter, Helicobacter, Flavobacterium, Fusobacterium, Ilyobacter, Neisseria*, or *Ureaplasma* peroxide-generating enzyme.

In one aspect, the peroxide-generating enzyme is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* peroxide-generating enzyme.

In another aspect, the peroxide-generating enzyme is a *Streptococcus equisimilis, Streptococcus pyogenes, Streptococcus uberis*, or *Streptococcus equi* subsp. *Zooepidemicus* peroxide-generating enzyme.

In another aspect, the peroxide-generating enzyme is a *Streptomyces achromogenes, Streptomyces avermitilis, Streptomyces coelicolor, Streptomyces griseus*, or *Streptomyces lividans* peroxide-generating enzyme.

The peroxide-generating enzyme may also be a fungal peroxide-generating enzyme, and more preferably a yeast peroxide-generating enzyme such as a *Candida, Kluyveromyces, Pichia, Saccharomyces, Schizosaccharomyces*, or *Yarrowia* peroxide-generating enzyme; or more preferably a filamentous fungal peroxide-generating enzyme such as an *Acremonium, Agaricus, Alternaria, Aspergillus, Aureobasidium, Botryospaeria, Ceriporiopsis, Chaetomidium, Chry-* sosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella, or Xylaria peroxide-generating enzyme.

In another aspect, the peroxide-generating enzyme is a Saccharomyces carlsbergensis, Saccharomyces cerevisiae, Saccharomyces diastaticus, Saccharomyces douglasii, Saccharomyces kluyveri, Saccharomyces norbensis, or Saccharomyces oviformis peroxide-generating enzyme.

In another aspect, the peroxide-generating enzyme is an Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, or Trichoderma viride peroxide-generating enzyme.

Examples of peroxide-generating enzymes and their sources include Cohn, 1958, The enzymatic formation of oxalacetic acid by nonpyridine nucleotide malic dehydrogenase of *Micrococcus lysodeikticus*, *J. Biol. Chem.* 233: 299-304; Yamashita et al., 2000, Isolation, characterization and molecular cloning of a thermostable xylitol oxidase from *Streptomyces* sp. IKD472, *J. Biosci. Bioeng.* 89: 350-360 (Accession No. Q9KX73); Seo et al., 2000, The *Arabidopsis* aldehyde oxidase 3 (AAO3) gene product catalyzes the final step in abscisic acid biosynthesis in leaves, *Proc. Natl. Acad. Sci. USA* 97: 12908-12913 (Accession No. Q7G191); Aurich et al., 1972, Purification and properties of L-amino acid oxidase from *Neurospora crassa*, *Acta Biol. Med. Ger.* 28: 209-220 (Accession No. P23623); Hoober and Thorpe, 2002, Flavin-dependent sulfhydryl oxidases in protein disulfide bond formation, *Methods Enzymol.* 348: 30-34; Baum and Scandalios, 1981, Isolation and characterization of the cytosolic and mitochondrial superoxide dismutases of maize, *Arch. Biochem. Biophys.* 206: 249-64 (Accession No. P09233); Holdom et al., 1996, The Cu,Zn superoxide dismutases of *Aspergillus flavus*, *Aspergillus niger*, *Aspergillus nidulans*, and *Aspergillus terreus*: purification and biochemical comparison with the *Aspergillus fumigatus* Cu,Zn superoxide dismutase, *Infect. Immun.* 64: 3326-3332 (Accession No. Q3MSU9); Lamarre et al., 2001, *Candida albicans* expresses an unusual cytoplasmic manganese-containing superoxide dismutase (SOD3 gene product) upon the entry and during the stationary phase, *J. Biol. Chem.* 276: 43784-43791 (Accession No. 013401); Dufernez et al., 2006, The presence of four iron-containing superoxide dismutase isozymes in trypanosomatidae: characterization, subcellular localization, and phylogenetic origin in *Trypanosoma brucei*, *Free Radic. Biol. Med.* 40(2):193-5 (Accession Nos. AY894557, AY894558, AY894559 and AY894560); Hjalmarsson et al., 1987, Isolation and sequence of complementary DNA encoding human extracellular superoxide dismutase *Proc. Natl. Acad. Sci. USA* 84:6340-6344 (Accession No. J02947); Yamada et al., 1999 Sequence and analysis of chromosome 2 of the plant *Arabidopsis Thaliana*, *Nature* 402: 761-768 (Accession No. Q9ZPY2); Kriechbaum et al., 1989, Cloning and DNA sequence analysis of the glucose oxidase gene from *Aspergillus niger* NRRL-3, *FEBS Lett.* 255 (1): 63-66 (Accession No. P13006); Kiess et al., 1998) Glucose oxidase from *Penicillium amagasakiense*. Primary structure and comparison with other glucose-methanol-choline (GMC) oxidoreductases *Eur. J. Biochem.* 252 (1): 90-99 (Accession No. P81156); Nierman et al., 2005, Genomic sequence of the pathogenic and allergenic filamentous fungus *Aspergillus fumigatus Nature* 438: 1151-1156 (Accession No. Q4WZA6); Toyama et al., 2005, Molecular cloning and structural analysis of quinohemoprotein alcohol dehydrogenase ADH-IIG from *Pseudomonas putida* HK5 *J. Mol. Biol.* 352 (1): 91-104 (Accession No. Q4W6G0).

Examples of cellobiose dehydrogenase and their sources include Xu et al., 2001, *Humicola insolens* cellobiose dehydrogenase: cloning, redox chemistry, and "logic gate"-like dual functionality, *Enz. Microb. Technol.* 28: 744-753 (Accession No. Q9P8H5); Nozaki et al., 1999, Cloning and expression of cellobiose dehydrogenase from *Irpex lacteus*. Submitted (AUG-2004) to the EMBL/GenBank/DDBJ databases (Accession No. Q6AW20); Moukha et al., 1999, Cloning and analysis of *Pycnoporus cinnabarinus* cellobiose dehydrogenase, Gene 234: 23-33 (Accession No. O74253); Li et al., 1996, Cloning of a cDNA encoding cellobiose dehydrogenase, a hemoflavoenzyme from *Phanerochaete chrysosporium*, *Appl. Environ. Microbiol.* 62: 1329-1335 (Accession No. Q01738); Kajisa et al., 2004, Characterization and molecular cloning of cellobiose dehydrogenase from the brown-rot fungus *Coniophora puteana*, *Biosci. Bioeng.* 98: 57-63 (Accession No. Q6BDD5); Zamocky et al., Phylogenetic analysis of cellobiose dehydrogenases. Submitted (NOV-2002) to the EMBL/GenBank/DDBJ databases (Accession No. Q7Z975); Yoshida et al., 2002, Molecular cloning and characterization of a cDNA encoding cellobiose dehydrogenase from the wood-rotting fungus *Grifola frondosa*, *FEMS Microbiol. Lett.* 217: 225-230 (Accession No. Q8J2T4); Stapleton et al., 2004, Molecular cloning of the cellobiose dehydrogenase gene from *Trametes versicolor* and expression in *Pichia pastoris*, *Enzyme Microb. Technol.* 34: 55-63 (Accession No. Q875J3); Dumonceaux et al., 1998, Cloning and sequencing of a gene encoding cellobiose dehydrogenase from *Trametes versicolor*, Gene 210: 211-219 (Accession No. O42729); Nierman et al., 2005, Genomic sequence of the pathogenic and allergenic filamentous fungus *Aspergillus fumigatus*, *Nature* 438: 1151-1156 (Accession No. Q4WIN9); Raices et al., 1995, Cloning and characterization of a cDNA encoding a cellobiose dehydrogenase from the white rot fungus *Phanerochaete chrysosporium*, *FEBS Lett.* 369: 233-238 (Accession No. Q12661); Zamocky et al., 2008, Cloning, sequence analysis and heterologous expression in *Pichia pastoris* of a gene encoding a thermostable cellobiose dehydrogenase from *Myriococcum thermophilum*, *Protein Expr. Purif.* 59: 258-265 (Accession No. A9XK88); Fedorova et al., Genomic islands in the pathogenic filamentous fungus *Aspergillus fumigatus*, PloS (Accession No. A1CFV0); Subramaniam et al., Biochemical and molecular biological characterization of cellobiose dehydrogenase from *Sporotrichum thermophilum*, Submitted (JUN-1998) to the EMBL/GenBank/DDBJ databases (Accession No. O74240); Fedorova et al., Genomic islands in the pathogenic filamentous fungus *Aspergillus fumigatus*, PloS (Accession No. A1CYG2); Fedorova et al., Genomic islands in the pathogenic filamentous fungus *Aspergillus fumigatus*, PloS (Accession No. B0XVQ8); Fedorova et al., Genomic islands in the pathogenic filamentous fungus *Aspergillus fumigatus*, PloS (Accession No. A1C890); Fedorova et al., Genomic islands in the pathogenic filamentous fungus *Aspergillus fumigatus*, PloS (Accession No. A1DIY3); Zamocky et al., 2008, Cloning, sequence analysis and heterologous expression in *Pichia pastoris* of a gene encoding a thermostable cellobiose dehydrogenase from *Myriococcum thermophilum*, *Protein Expr. Purif.* 59: 258-265 (Accession No. A9XK87); Birren et al., The Broad Institute Genome Sequencing Platform "Genome Sequence of *Pyrenophora tritici-repentis*, Submitted (MAR-2007) to the EMBL/GenBank/DDBJ databases (Accession No. B2WHI7); Birren et al., The Broad Institute Genome Sequencing Platform "Genome Sequence of *Pyrenophora tritici-repentis*, Submitted (MAR-2007) to the EMBL/GenBank/DDBJ databases (Accession No. B2WJX3); Fedorova et al., Genomic islands in the pathogenic filamentous fungus *Aspergillus fumigatus*, PloS (Accession No. Q4WC40); and Pel et al., 2007, Genome sequencing and analysis of the versatile cell factory *Aspergillus niger* CBS 513.88, *Nat. Biotechnol.* 25: 221-231 (Accession No. A2QD75).

In one aspect, the cellobiose dehydrogenase is a *Humicola insolens* cellobiose dehydrogenase. In another aspect, the cellobiose dehydrogenase is a *Humicola insolens* DSM 1800 cellobiose dehydrogenase, e.g., the polypeptide comprising SEQ ID NO: 18 encoded by SEQ ID NO: 17, or a fragment thereof having cellobiose dehydrogenase activity (see U.S. Pat. No. 6,280,976).

In another aspect, the cellobiose dehydrogenase is a *Myceliophthora thermophila* cellobiose dehydrogenase. In another aspect, the cellobiose dehydrogenase is a *Myceliophthora thermophila* CBS 117.65 cellobiose dehydrogenase.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Non-Enzymatic Peroxide-Generating Systems

In the present invention, the peroxide generation system can be any peroxide-generating chemical reaction or system of reactions. The peroxide-generating system may be present as a reaction between components in the enzyme composition and/or one or more (several) of the components of the biomass and/or one or more (several) chemical components added to the composition. In one aspect, the peroxide is hydrogen peroxide.

Examples of peroxide generating systems include, but are not limited to, UV-irradiation of Rose Bengal (Wright et al., 2000, Singlet Oxygen-Mediated Protein Oxidation: Evidence for the Formation of Reactive Peroxides, Redox Report, 5:159-161); the Reidl-Pfleiderer process of autooxidation of 2-ethyl-9,10-dihydroxyanthracene+$O_2$ to 2-ethylanthraquinone+$H_2O_2$; Eul et al., 2001, Hydrogen peroxide, in *Kirk-Othmer Encyclopedia of Chemical Technology Wiley*, New York; reaction of singlet state molecular oxygen $^1O_2$ with ascorbate (Kramarenko et al., 2006, Ascorbate Reacts with Singlet Oxygen to Produce Hydrogen Peroxide, *Photochem. Photobiol.* 82(6):1634-1637); the oxidation of unsaturated lipid (after radical initiation) to lipid peroxide (Benzie, 1996, Lipid peroxidation: A review of causes, consequences, measurement and dietary influences, *International Journal of Food Sciences and Nutrition* 47(3): 233-261); and the oxidation of organic alcohols by molecular oxygen in the presence of various metal and metal complex catalysts (Bortolo et al., 2000, Production of Hydrogen Peroxide from Oxygen and Alcohols, Catalyzed by Palladium Complexes, *J. Mol. Cat. A. Chem.*, 153:25-29).

Polypeptides Having Peroxidase Activity

In the methods of the present invention, the polypeptide having peroxidase activity can be any polypeptide having peroxidase activity. The polypeptide having peroxidase activity may be present as an enzyme activity in the enzyme composition and/or as one or more (several) protein components added to the composition. In a preferred aspect, the polypeptide having peroxidase activity is foreign to one or more (several) components of the enzyme composition.

Examples of peroxidase or peroxide-decomposing enzymes include, but are not limited to, the following:

E.C. 1.11.1.1 NADH peroxidase
E.C. 1.11.1.2 NADPH peroxidase
E.C. 1.11.1.3 fatty acid peroxidase
E.C. 1.11.1.5 di-heme cytochrome c peroxidase
E.C. 1.11.1.5 cytochrome c peroxidase
E.C. 1.11.1.6 catalase
E.C. 1.11.1.6 manganese catalase
E.C. 1.11.1.7 invertebrate peroxinectin
E.C. 1.11.1.7 eosinophil peroxidase
E.C. 1.11.1.7 lactoperoxidase
E.C. 1.11.1.7 myeloperoxidase
E.C. 1.11.1.8 thyroid peroxidase
E.C. 1.11.1.9 glutathione peroxidase
E.C. 1.11.1.10 chloride peroxidase
E.C. 1.11.1.11 ascorbate peroxidase
E.C. 1.11.1.12 other glutathione peroxidase
E.C. 1.11.1.13 manganese peroxidase
E.C. 1.11.1.14 lignin peroxidase
E.C. 1.11.1.15 cysteine peroxiredoxin
E.C. 1.11.1.16 versatile peroxidase
E.C. 1.11.1.B2 chloride peroxidase
E.C. 1.11.1.B4 haloperoxidase
E.C. 1.11.1.84 no-heme vanadium haloperoxidase
E.C. 1.11.1.B6 iodide peroxidase
E.C. 1.11.1.87 bromide peroxidase
E.C. 1.11.1.B8 iodide peroxidase In one aspect, the peroxidase is a NADH peroxidase. In another aspect, the peroxidase is a NADPH peroxidase. In another aspect, the peroxidase is a fatty acid peroxidase. In another aspect, the peroxidase is a di-heme cytochrome c peroxidase. In another aspect, the peroxidase is a cytochrome c peroxidase. In another aspect, the peroxidase is a catalase. In another aspect, the peroxidase is a manganese catalase. In another aspect, the peroxidase is an invertebrate peroxinectin. In another aspect, the peroxidase is an eosinophil peroxidase.

In another aspect, the peroxidase is a lactoperoxidase. In another aspect, the peroxidase is a myeloperoxidase. In another aspect, the peroxidase is a thyroid peroxidase. In another aspect, the peroxidase is a glutathione peroxidase. In another aspect, the peroxidase is a chloride peroxidase. In another aspect, the peroxidase is an ascorbate peroxidase. In another aspect, the peroxidase is a glutathione peroxidase. In another aspect, the peroxidase is a manganese peroxidase. In another aspect, the peroxidase is a lignin peroxidase. In another aspect, the peroxidase is a cysteine peroxiredoxin. In another aspect, the peroxidase is a versatile peroxidase. In another aspect, the peroxidase is a chloride peroxidase. In another aspect, the peroxidase is a haloperoxidase. In another aspect, the peroxidase is a no-heme vanadium haloperoxidase. In another aspect, the peroxidase is an iodide peroxidase. In another aspect, the peroxidase is a bromide peroxidase. In another aspect, the peroxidase is a iodide peroxidase.

Examples of polypeptides having peroxidase activity include, but are not limited to, *Coprinus cinereus* peroxidase (Baunsgaard et al., 1993, Amino acid sequence of *Coprinus macrorhizus* peroxidase and cDNA sequence encoding *Coprinus cinereus* peroxidase. A new family of fungal peroxidases, *Eur. J. Biochem.* 213 (1): 605-611 (Accession number P28314); horseradish peroxidase (Fujiyama et al., 1988, Structure of the horseradish peroxidase isozyme C genes, *Eur. J. Biochem.* 173 (3): 681-687 (Accession number P15232); peroxiredoxin (Singh and Shichi, 1998, A novel glutathione peroxidase in bovine eye. Sequence analysis, mRNA level, and translation, *J. Biol. Chem.* 273 (40): 26171-26178 (Accession number O77834); lactoperoxidase (Dull et al., 1990, Molecular cloning of cDNAs encoding bovine and human lactoperoxidase, *DNA Cell Biol.* 9 (7): 499-509 (Accession number P80025); Eosinophil peroxidase (Fornhem et al., 1996, Isolation and characterization of porcine cationic eosinophilgranule proteins, *Int. Arch. Allergy Immunol.* 110 (2): 132-142 (Accession number P80550); versatile peroxidase (Ruiz-Duenas et al., 1999, Molecular characterization of a novel peroxidase isolated from the ligninolytic fungus *Pleurotus eryngii*, *Mol. Microbiol.* 31 (1): 223-235 (Accession number O94753); turnip peroxidase (Mazza and Welinder, 1980, Covalent structure of turnip peroxidase 7. Cyanogen bromide fragments, complete structure and comparison to horseradish peroxidase C, *Eur. J. Biochem.* 108 (2): 481-489 (Accession number P00434); myeloperoxidase (Morishita et al., 1987, Chromosomal gene structure of human myeloperoxidase and regulation of its expression by granulocyte colony-stimulating factor, *J. Biol. Chem.* 262 (31): 15208-15213 (Accession number P05164); peroxidasin and peroxidasin homologs (Horikoshi et al., 1999, Isolation of differentially expressed cDNAs from p53-dependent apoptotic cells: activation of the human homologue of the *Drosophila* peroxidasin gene, *Biochem. Biophys. Res. Commun.* 261 (3): 864-869 (Accession number Q92626); lignin peroxidase (Tien and Tu, 1987, Cloning and sequencing of a cDNA for a ligninase from *Phanerochaete chrysosporium*, *Nature* 326 (6112): 520-523 (Accession number P06181); Manganese peroxidase (Orth et al., 1994, Characterization of a cDNA encoding a manganese peroxidase from *Phanerochaete chrysosporium*: genomic organization of lignin and manganese peroxidase-encoding genes, *Gene* 148 (1): 161-165 (Accession number P78733); alpha-dioxygenase, dual oxidase, peroxidasin, invertebrate peroxinectin, short peroxidockerin, lactoperoxidase, myeloperoxidase, non-mammalian vertebrate peroxidase, catalase, catalase-lipoxygenase fusion, diheme cytochrome c peroxidase, methylamine utilization protein, DyP-type peroxidase, haloperoxidase, ascorbate peroxidase, catalase peroxidase, hybrid ascorbate-cytochrome c peroxidase, lignin peroxidase, manganese peroxidase, versatile peroxidase, other class II peroxidase, class III peroxidase, alkylhydroperoxidase D, other alkylhydroperoxidases, no-heme, no metal haloperoxidase, no-heme vanadium haloperoxidase, manganese catalase, NADH peroxidase, glutathione peroxidase, cysteine peroxiredoxin, thioredoxin-dependent thiol peroxidase, and AhpE-like peroxiredoxin (Passard et al., 2007, *Phytochemistry* 68:1605-1611.

The polypeptide having peroxidase activity may be obtained from microorganisms of any genus. In one aspect, the polypeptide obtained from a given source is secreted extracellularly.

The polypeptide having peroxidase activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus*, or *Oceanobacillus* polypeptide having peroxidase activity, or a Gram negative bacterial polypeptide such as an *E. coli, Pseudomonas, Salmonella, Campylobacter, Helicobacter, Flavobacterium, Fusobacterium, Ilyobacter, Neisseria*, or *Ureaplasma* polypeptide having peroxidase activity.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having peroxidase activity.

In another aspect, the polypeptide is a *Streptococcus equisimilis, Streptococcus pyogenes, Streptococcus uberis,* or *Streptococcus equi* subsp. *Zooepidemicus* polypeptide having peroxidase activity.

In another aspect, the polypeptide is a *Streptomyces achromogenes, Streptomyces avermitilis, Streptomyces coelicolor, Streptomyces griseus,* or *Streptomyces lividans* polypeptide having peroxidase activity.

The polypeptide having peroxidase activity may also be a fungal polypeptide, and more preferably a yeast polypeptide such as a *Candida, Kluyveromyces, Pichia, Saccharomyces, Schizosaccharomyces,* or *Yarrowia* polypeptide having peroxidase activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having peroxidase activity.

In another aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having peroxidase activity.

In another aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium*

*lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei,* or *Trichoderma viride* polypeptide having peroxidase activity.

In another aspect, the peroxidase is horseradish peroxidase. In another aspect, the peroxidase is *Coprinus cinereus* peroxidase.

Techniques used to isolate or clone a polynucleotide encoding a polypeptide having peroxidase activity are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and nucleotide sequence-based amplification (NASBA) may be used.

Enzyme Compositions

In the methods of the present invention, the enzyme composition may comprise any protein involved in the processing of a cellulose-containing material to glucose and/or cellobiose, or hemicellulose to xylose, mannose, galactose, and/or arabinose.

The enzyme composition preferably comprises enzymes having cellulolytic activity and/or xylan degrading activity. In one aspect, the enzyme composition comprises one or more (several) cellulolytic enzymes. In another aspect, the enzyme composition comprises one or more (several) xylan degrading enzymes. In another aspect, the enzyme composition comprises one or more (several) cellulolytic enzymes and one or more (several) xylan degrading enzymes.

The one or more (several) cellulolytic enzymes are preferably selected from the group consisting of an endoglucanase, a cellobiohydrolase, and a beta-glucosidase. The one or more (several) xylan degrading enzymes are preferably selected from the group consisting of a xylanase, an acetyxylan esterase, a feruloyl esterase, an arabinofuranosidase, a xylosidase, and a glucuronidase.

In another aspect, the enzyme composition may further or even further comprise one or more (several) additional enzyme activities to improve the degradation of the cellulose-containing material. Preferred additional enzymes are hemicellulases (e.g., alpha-D-glucuronidases, alpha-L-arabinofuranosidases, endo-mannanases, beta-mannosidases, alpha-galactosidases, endo-alpha-L-arabinanases, beta-galactosidases), carbohydrate-esterases (e.g., acetyl-xylan esterases, acetyl-mannan esterases, ferulic acid esterases, coumaric acid esterases, glucuronoyl esterases), pectinases, proteases, ligninolytic enzymes (e.g., laccases, manganese peroxidases, lignin peroxidases, $H_2O_2$-producing enzymes, oxidoreductases), expansins, swollenins, or mixtures thereof. In the methods of the present invention, the additional enzyme(s) can be added prior to or during fermentation, e.g., during saccharification or during or after propagation of the fermenting microorganism(s).

One or more (several) components of the enzyme composition may be wild-type proteins, recombinant proteins, or a combination of wild-type proteins and recombinant proteins. For example, one or more (several) components may be native proteins of a cell, which is used as a host cell to express recombinantly one or more (several) other components of the enzyme composition. One or more (several) components of the enzyme composition may be produced as monocomponents, which are then combined to form the enzyme composition. The enzyme composition may be a combination of multicomponent and monocomponent protein preparations.

The enzymes used in the methods of the present invention may be in any form suitable for use in the processes described herein, such as, for example, a crude fermentation broth with or without cells removed, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

A polypeptide having cellulolytic enzyme activity or xylan degrading activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus,* or *Oceanobacillus* polypeptide having cellulolytic enzyme activity or xylan degrading activity, or a Gram negative bacterial polypeptide such as an *E. coli, Pseudomonas, Salmonella, Campylobacter, Helicobacter, Flavobacterium, Fusobacterium, Ilyobacter, Neisseria,* or *Ureaplasma* polypeptide having cellulolytic enzyme activity or xylan degrading activity.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having cellulolytic enzyme activity or xylan degrading activity.

In another preferred aspect, the polypeptide is a *Streptococcus equisimilis, Streptococcus pyogenes, Streptococcus uberis,* or *Streptococcus equi* subsp. *Zooepidemicus* polypeptide having cellulolytic enzyme activity or xylan degrading activity.

In another preferred aspect, the polypeptide is a *Streptomyces achromogenes, Streptomyces avermitilis, Streptomyces coelicolor, Streptomyces griseus,* or *Streptomyces lividans* polypeptide having cellulolytic enzyme activity or xylan degrading activity.

The polypeptide having cellulolytic enzyme activity or xylan degrading activity may also be a fungal polypeptide, and more preferably a yeast polypeptide such as a *Candida, Kluyveromyces, Pichia, Saccharomyces, Schizosaccharomy-* ces, or *Yarrowia* polypeptide having cellulolytic enzyme activity or xylan degrading activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide having cellulolytic enzyme activity or xylan degrading activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having cellulolytic enzyme activity or xylan degrading activity.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride*, or *Trichophaea saccata* polypeptide having cellulolytic enzyme activity or xylan degrading activity.

Chemically modified or protein engineered mutants of polypeptides having cellulolytic enzyme activity or xylan degrading activity may also be used.

One or more (several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

Examples of commercial cellulolytic protein preparations suitable for use in the present invention include, for example, CELLIC™ Ctec (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.). The cellulase enzymes are added in amounts effective from about 0.001 to about 5.0 wt % of solids, more preferably from about 0.025 to about 4.0 wt % of solids, and most preferably from about 0.005 to about 2.0 wt % of solids. The cellulase enzymes are added in amounts effective from about 0.001 to about 5.0 wt % of solids, more preferably from about 0.025 to about 4.0 wt % of solids, and most preferably from about 0.005 to about 2.0 wt % of solids.

Examples of bacterial endoglucanases that can be used in the methods of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the methods of the present invention, include, but are not limited to, a *Trichoderma reesei* endoglucanase I (Penttila et al., 1986, *Gene* 45: 253-263; GENBANK™ accession no. M15665); *Trichoderma reesei* endoglucanase II (Saloheimo, et al., 1988, Gene 63:11-22; GENBANK™ accession no. M19373); *Trichoderma reesei* endoglucanase III (Okada et al., 1988, *Appl. Environ. Microbiol.* 64: 555-563; GENBANK™ accession no. AB003694); *Aspergillus aculeatus* endoglucanase (Ooi et al., 1990, *Nucleic Acids Research* 18: 5884); *Aspergillus kawachii* endoglucanase (Sakamoto et al., 1995, *Current Genetics* 27: 435-439); *Erwinia carotovara* endoglucanase (Saarilahti et al., 1990, *Gene* 90: 9-14); *Fusarium oxysporum* endoglucanase (GENBANK™ accession no. L29381); *Humicola grisea* var. *thermoidea* endoglucanase (GENBANK™ accession no. AB003107); *Melanocarpus albomyces* endoglucanase (GENBANK™ accession no. MAL515703); *Neurospora crassa* endoglucanase (GENBANK™ accession no. XM_324477); *Humicola insolens* endoglucanase V (SEQ ID NO: 20); *Myceliophthora thermophila* CBS 117.65 endoglucanase (SEQ ID NO: 22); basidiomycete CBS 495.95 endoglucanase (SEQ ID NO: 24); basidiomycete CBS 494.95 endoglucanase (SEQ ID NO: 26); *Thielavia terrestris* NRRL 8126 CEL6B endoglucanase (SEQ ID NO: 28); *Thielavia terrestris* NRRL 8126 CEL6C endoglucanase (SEQ ID NO: 30); *Thielavia terrestris* NRRL 8126 CEL7C endoglucanase (SEQ ID NO: 32); *Thielavia terrestris* NRRL 8126 CEL7E endoglucanase (SEQ ID NO: 34); *Thielavia terrestris* NRRL 8126 CEL7F endoglucanase (SEQ ID NO: 36); *Cladorrhinum foecundissimum* ATCC 62373 CEL7A endoglucanase (SEQ ID NO: 38); and *Trichoderma reesei* strain No. VTT-D-80133 endoglucanase (SEQ ID NO: 40; GENBANK™ accession no. M15665). The endoglucanases of SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, and SEQ ID NO: 40 described above are encoded by the mature polypeptide coding sequence of SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, respectively.

Examples of cellobiohydrolases useful in the methods of the present invention include, but are not limited to, *Tricho-*

*derma reesei* cellobiohydrolase I (SEQ ID NO: 42); *Trichoderma reesei* cellobiohydrolase II (SEQ ID NO: 44); *Humicola insolens* cellobiohydrolase I (SEQ ID NO: 46), *Myceliophthora thermophila* cellobiohydrolase II (SEQ ID NO: 48 and SEQ ID NO: 50), *Thielavia terrestris* cellobiohydrolase II (CEL6A) (SEQ ID NO: 52), *Chaetomium thermophilum* cellobiohydrolase I (SEQ ID NO: 54), and *Chaetomium thermophilum* cellobiohydrolase II (SEQ ID NO: 56). The cellobiohydrolases of SEQ ID NO: 40, SEQ ID NO: 42, SEQ ID NO: 44, SEQ ID NO: 46, SEQ ID NO: 48, SEQ ID NO: 50, SEQ ID NO: 52, and SEQ ID NO: 54 described above are encoded by the mature polypeptide coding sequence of SEQ ID NO: 41, SEQ ID NO: 43, SEQ ID NO: 45, SEQ ID NO: 47, SEQ ID NO: 49, SEQ ID NO: 51, SEQ ID NO: 53, and SEQ ID NO: 55, respectively.

Examples of beta-glucosidases useful in the methods of the present invention include, but are not limited to, *Aspergillus oryzae* beta-glucosidase (SEQ ID NO: 58); *Aspergillus fumigatus* beta-glucosidase (SEQ ID NO: 60); *Penicillium brasilianum* IBT 20888 beta-glucosidase (SEQ ID NO: 62); *Aspergillus niger* beta-glucosidase (SEQ ID NO: 64); and *Aspergillus aculeatus* beta-glucosidase (SEQ ID NO: 66). The beta-glucosidases of SEQ ID NO: 58, SEQ ID NO: 60, SEQ ID NO: 62, SEQ ID NO: 64, and SEQ ID NO: 66 described above are encoded by the mature polypeptide coding sequence of SEQ ID NO: 57, SEQ ID NO: 59, SEQ ID NO: 61, SEQ ID NO: 63, and SEQ ID NO: 65, respectively.

The *Aspergillus oryzae* polypeptide having beta-glucosidase activity can be obtained according to WO 2002/095014. The *Aspergillus fumigatus* polypeptide having beta-glucosidase activity can be obtained according to WO 2005/047499. The *Penicillium brasilianum* polypeptide having beta-glucosidase activity can be obtained according to WO 2007/019442. The *Aspergillus niger* polypeptide having beta-glucosidase activity can be obtained according to Dan et al., 2000, *J. Biol. Chem.* 275: 4973-4980. The *Aspergillus aculeatus* polypeptide having beta-glucosidase activity can be obtained according to Kawaguchi et al., 1996, *Gene* 173: 287-288.

The beta-glucosidase may be a fusion protein. In one aspect, the beta-glucosidase is the *Aspergillus oryzae* beta-glucosidase variant BG fusion protein of SEQ ID NO: 68 or the *Aspergillus oryzae* beta-glucosidase fusion protein of SEQ ID NO: 70. In another aspect, the *Aspergillus oryzae* beta-glucosidase variant BG fusion protein is encoded by the polynucleotide of SEQ ID NO: 67 or the *Aspergillus oryzae* beta-glucosidase fusion protein is encoded by the polynucleotide of SEQ ID NO: 69.

Other endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in EP 495,257, EP 531,315, EP 531,372, WO 89/09259, WO 94/07998, WO 95/24471, WO 96/11262, WO 96/29397, WO 96/034108, WO 97/14804, WO 98/08940, WO 98/012307, WO 98/13465, WO 98/015619, WO 98/015633, WO 98/028411, WO 99/06574, WO 99/10481, WO 99/025846, WO 99/025847, WO 99/031255, WO 2000/009707, WO 2002/050245, WO 2002/0076792, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. Nos. 4,435,307, 5,457,046, 5,648,263, 5,686,593, 5,691,178, 5,763,254, and 5,776,757.

Examples of commercial xylan degrading enzyme preparations suitable for use in the present invention include, for example, SHEARZYME™ (Novozymes A/S), CELLIC™ Htec (Novozymes A/S), VISCOZYME® (Novozymes A/S), ULTRAFLO® (Novozymes A/S), PULPZYME® HC (Novozymes A/S), MULTIFECT® Xylanase (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the methods of the present invention include, but are not limited to, *Aspergillus aculeatus* xylanase (GeneSeqP:AAR63790; WO 94/21785), *Aspergillus fumigatus* xylanases (WO 2006/078256), and *Thielavia terrestris* NRRL 8126 xylanases (WO 2009/079210).

Examples of beta-xylosidases useful in the methods of the present invention include, but are not limited to, *Trichoderma reesei* beta-xylosidase (UniProtKB/TrEMBL accession number Q92458), *Talaromyces emersonii* (SwissProt accession number Q8×212), and *Neurospora crassa* (SwissProt accession number Q7SOW4).

Examples of acetylxylan esterases useful in the methods of the present invention include, but are not limited to, *Hypocrea jecorina* acetylxylan esterase (WO 2005/001036), *Neurospora crassa* acetylxylan esterase (UniProt accession number q7s259), *Thielavia terrestris* NRRL 8126 acetylxylan esterase (WO 2009/042846), *Chaetomium globosum* acetylxylan esterase (Uniprot accession number Q2GWX4), *Chaetomium gracile* acetylxylan esterase (GeneSeqP accession number AAB82124), *Phaeosphaeria nodorum* acetylxylan esterase (Uniprot accession number Q0UHJ1), and *Humicola insolens* DSM 1800 acetylxylan esterase (WO 2009/073709).

Examples of ferulic acid esterases useful in the methods of the present invention include, but are not limited to, *Humicola insolens* DSM 1800 feruloyl esterase (WO 2009/076122), *Neurospora crassa* feruloyl esterase (UniProt accession number Q9HGR3), and *Neosartorya fischeri* feruloyl esterase (UniProt Accession number A1D9T4).

Examples of arabinofuranosidases useful in the methods of the present invention include, but are not limited to, *Humicola insolens* DSM 1800 arabinofuranosidase (WO 2009/073383) and *Aspergillus niger* arabinofuranosidase (GeneSeqP accession number AAR94170).

Examples of alpha-glucuronidases useful in the methods of the present invention include, but are not limited to, *Aspergillus clavatus* alpha-glucuronidase (UniProt accession number alcc12), *Trichoderma reesei* alpha-glucuronidase (Uniprot accession number Q99024), *Talaromyces emersonii* alpha-glucuronidase (UniProt accession number Q8×211), *Aspergillus niger* alpha-glucuronidase (Uniprot accession number Q96WX9), *Aspergillus terreus* alpha-glucuronidase (SwissProt accession number Q0CJP9), and *Aspergillus fumigatus* alpha-glucuronidase (SwissProt accession number Q4WW45).

The enzymes and proteins used in the methods of the present invention may be produced by fermentation of the above-noted microbial strains on a nutrient medium containing suitable carbon and nitrogen sources and inorganic salts, using procedures known in the art (see, e.g., Bennett, J. W.

and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Nucleic Acid Constructs

Nucleic acid constructs comprising an isolated polynucleotide encoding a polypeptide of interest, e.g., one or more (several) cellulolytic enzymes, a polypeptide having peroxidase activity, or a polypeptide having cellulolytic enhancing activity, operably linked to one or more (several) control sequences may be constructed that direct the expression of the coding sequence in a suitable host cell under conditions compatible with the control sequences.

The isolated polynucleotide may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (VIIIa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter including a gene encoding a neutral alpha-amylase in *Aspergilli* in which the untranslated leader has been replaced by an untranslated leader from a gene encoding triose phosphate isomerase in *Aspergilli*; non-limiting examples include modified promoters including the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae 3-phosphoglycerate kinase, Saccharomyces cerevisiae alpha-factor, and Saccharomyces cerevisiae alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, Molecular Cellular Biology 15: 5983-5990.

The control sequence may also be a signal peptide coding sequence that encodes a signal peptide linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the native signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for bacterial host cells are the signal peptide coding sequences obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide.

The propeptide coding sequence may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

Recombinant expression vectors comprising a polynucleotide encoding a polypeptide of interest, e.g., one or more (several) cellulolytic enzymes, a polypeptide having peroxidase activity, or a polypeptide having cellulolytic enhancing activity, a promoter, and transcriptional and translational stop signals may be constructed for expression of the polypeptide in a suitable host cell. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors are well known to one skilled in the art (see, e.g., Sambrook et al., 1989, supra).

Host Cells

The nucleic acid constructs or expression vectors comprising an isolated polynucleotide encoding a polypeptide of interest, e.g., one or more (several) cellulolytic enzymes, a polypeptide having peroxidase activity, or a polypeptide having cellulolytic enhancing activity, may be introduced into recombinant host cells for the recombinant production of the polypeptides. A vector comprising a polynucleotide is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide, e.g., a prokaryote or a eukaryote.

The prokaryotic host cell may be any Gram positive bacterium or a Gram negative bacterium. Gram positive bacteria include, but not limited to, *Bacillus*, *Streptococcus*, *Streptomyces*, *Staphylococcus*, *Enterococcus*, *Lactobacillus*, *Lactococcus*, *Clostridium*, *Geobacillus*, and *Oceanobacillus*. Gram negative bacteria include, but not limited to, *E. coli*, *Pseudomonas*, *Salmonella*, *Campylobacter*, *Helicobacter*, *Flavobacterium*, *Fusobacterium*, *Ilyobacter*, *Neisseria*, and *Ureaplasma*.

The bacterial host cell may be any *Bacillus* cell. *Bacillus* cells include, but are not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

In a preferred aspect, the bacterial host cell is a *Bacillus amyloliquefaciens*, *Bacillus lentus*, *Bacillus licheniformis*, *Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells include, but are not limited to, *Streptococcus equisimilis*, *Streptococcus pyogenes*, *Streptococcus uberis*, and *Streptococcus equi* subsp. *Zooepidemicus* cells.

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells include, but are not limited to, *Streptomyces achromogenes*, *Streptomyces avermitilis*, *Streptomyces coelicolor*, *Streptomyces griseus*, and *Streptomyces lividans* cells.

In a preferred aspect, the bacterial host cell is a *Streptomyces* achromogenes cell. In another preferred aspect, the bacterial host cell is a *Streptomyces* avermitilis cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (Praha) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-207), by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred aspect, the yeast host cell is a *Candida*, *Hansenula*, *Kluyveromyces*, *Pichia*, *Saccharomyces*, *Schizosaccharomyces*, or *Yarrowia* cell.

In a most preferred aspect, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

In a most preferred aspect, the filamentous fungal host cell is an *Aspergillus awamori*, *Aspergillus fumigatus*, *Aspergillus foetidus*, *Aspergillus japonicus*, *Aspergillus nidulans*, *Aspergillus niger* or *Aspergillus oryzae* cell. In another most preferred aspect, the filamentous fungal host cell is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, or *Fusarium venenatum* cell. In another most preferred aspect, the filamentous fungal host cell is a *Bjerkandera adusta*, *Ceriporiopsis aneirina*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium keratinophilum*, *Chrysosporium lucknowense*, *Chrysosporium tropicum*, *Chrysosporium merdarium*, *Chrysosporium inops*, *Chrysosporium pannicola*, *Chrysosporium queenslandicum*, *Chrysosporium zonatum*, *Coprinus cinereus*, *Coriolus hirsutus*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78:

147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

A polypeptide of interest, e.g., one or more (several) cellulolytic enzymes, a polypeptide having peroxidase activity, or a polypeptide having cellulolytic enhancing activity, can be produced by (a) cultivating a cell, which in its wild-type form produces the polypeptide, under conditions conducive for production of the polypeptide; and (b) recovering the polypeptide.

The polypeptide of interest can also be produced by (a) cultivating a recombinant host cell, as described herein, under conditions conducive for production of the polypeptide; and (b) recovering the polypeptide.

In the production methods, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

The present invention is further described by the following examples that should not be construed as limiting the scope of the invention.

EXAMPLES

Example 1

Growth of *Myceliophthora thermophila* CBS 117.65

Two plugs from a PDA plate of *Myceliophthora thermophila* CBS 117.65 were inoculated into a 500 ml shake flask containing 100 ml of shake flask medium to obtain culture broth for the purification of a cellobiose dehydrogenase. PDA plates were composed of 39 g of potato dextrose agar and deionized water to 1 liter. The shake flask medium was composed of 15 g of glucose, 4 g of $K_2HPO_4$, 1 g of NaCl, 0.2 g of $MgSO_4.7H_2O$, 2 g of MES free acid, 1 g of Bacto Peptone, 5 g of yeast extract, 2.5 g of citric acid, 0.2 g of $CaCl_2.2H_2O$, 5 g of $NH_4NO_3$, 1 ml of trace elements solution, and deionized water to 1 liter. The trace elements solution was composed of 1.2 g of $FeSO_4.7H_2O$, 10 g of $ZnSO_4.7H_2O$, 0.7 g of $MnSO_4.H_2O$, 0.4 g of $CuSO_4.5H_2O$, 0.4 g of $Na_2B_4O_7.10H_2O$, 0.8 g of $Na_2MoO_2.2H_2O$, and deionized water to 1 liter. The shake flask was incubated at 45° C. on an orbital shaker at 200 rpm for 48 hours. Fifty ml of the shake flask broth was used to inoculate a 2 liter fermentation vessel.

A total of 1.8 liters of the fermentation batch medium was added to a two liter glass jacketed fermentor (Applikon Biotechnology, Schiedam, Netherlands). Fermentation feed medium was dosed at a rate of 4 g/l/hour for a period of 72 hours. Fermentation batch medium was composed of 5 g of yeast extract, 176 g of powdered cellulose, 2 g of glucose, 1 g of NaCl, 1 g of Bacto Peptone, 4 g of $K_2HPO_4$, 0.2 g of $CaCl_2.2H_2O$, 0.2 g of $MgSO_4.7H_2O$, 2.5 g of citric acid, 5 g of $NH_4NO_3$, 1.8 ml of anti-foam, 1 ml of trace elements solution, and deionized water to 1 liter. The fermentation vessel was maintained at a temperature of 45° C. and pH was controlled using an Applikon 1030 control system (Applikon Biotechnology, Schiedam, Netherlands) to a set-point of 5.6+/−0.1. Air was added to the vessel at a rate of 1 vvm and the broth was agitated by Rushton impeller rotating at 1100 to 1300 rpm. At the end of the fermentation, whole broth was harvested from the vessel and centrifuged at 3000×g to remove the biomass.

Example 2

Purification of *Myceliophthora thermophila* CBS 117.65 Cellobiose Dehydrogenase The *Myceliophthora thermophila* CBS 117.65 harvested broth described in Example 1 was centrifuged in 500 ml bottles at 13,000×g for 20 minutes at 4° C. and then sterile filtered using a 0.22 μm polyethersulfone membrane (Millipore, Bedford, Mass., USA). The filtered broth was concentrated and buffer exchanged with 20 mM Tris-HCl pH 8.5 using a tangential flow concentrator (Pall Filtron, Northborough, Mass., USA) equipped with a 10 kDa polyethersulfone membrane (Pall Filtron, Northborough, Mass., USA). To decrease the amount of pigment, the concentrate was applied to a 60 ml Q-SEPHAROSE BIG BEAD™ column (GE Healthcare, Piscataway, N.J., USA) equilibrated with 20 mM Tris-HCl pH 8.5, and eluted stepwise with equilibration buffer containing 600 mM NaCl. Flow-through and eluate fractions were analyzed by SDS-PAGE using 8-16% CRITERION™ SDS-PAGE gels (Bio-Rad Laboratories, Inc., Hercules, Calif., USA) and stained with GELCODE™ Blue protein stain (Thermo Fisher Scientific, Waltham, Mass., USA). The eluate fraction contained cellobiose dehydrogenase (CBDH) as judged by the presence of a band corresponding to the apparent molecular weight of approximately 100 kDa by SDS-PAGE (Schou et al., 1998, *Biochem. J.* 330: 565-571).

The eluate fraction was concentrated using an AMICON™ ultrafiltration device (Millipore, Bedford, Mass., USA) equipped with a 10 kDa polyethersulfone membrane, and buffer-exchanged into 20 mM Tris-HCl pH 8.5 using a HIPREP® 26/10 desalting column (GE Heathcare, Piscataway, N.J., USA). The desalted material was loaded onto a MONO Q® column (HR 16/10, GE Healthcare, Piscataway, N.J., USA) equilibrated with 20 mM Tris-HCl pH 8.5. Bound proteins were eluted with a linear NaCl gradient from 0 to 500 mM (18 column volumes) in 20 mM Tris-HCl pH 8.5. Fractions were analyzed by SDS-PAGE as described above and the cellobiose dehydrogenase eluted at approximately 350-400 mM NaCl.

Fractions containing cellobiose dehydrogenase were pooled (60 ml) and mixed with an equal volume of 20 mM Tris-HCl pH 7.5 containing 3.4 M ammonium sulfate to yield a final concentration of 1.7 M ammonium sulfate. The sample was filtered (0.2 µM syringe filter, polyethersulfone membrane, Whatman, Maidstone, United Kingdom) to remove particulate matter prior to loading onto a Phenyl Superose column (HR 16/10, GE Healthcare, Piscataway, N.J., USA) equilibrated with 1.7 M ammonium sulfate in 20 mM Tris-HCl pH 7.5. Bound proteins were eluted with a decreasing 1.7→0 M ammonium sulfate gradient (12 column volumes) in 20 mM Tris-HCl pH 7.5. Fractions were analyzed by SDS-PAGE as described above and the cellobiose dehydrogenase eluted at approximately 800 mM ammonium sulfate. The cellobiose dehydrogenase fraction was >90% pure as judged by SDS-PAGE. CBDH activity was confirmed by a 2,6-dichlorophenolindophenol (DCIP) reduction assay in the presence of cellobiose, as described by Schou et al., 1998, supra.

Fractions containing cellobiose dehydrogenase were pooled, concentrated, and buffer exchanged into 20 mM Tris-HCl pH 7.5 by centrifugal concentration in a SORVALL® RT7 centrifuge (Thermo Fisher Scientific, Waltham, Mass., USA) using VIVASPIN™ 20 centrifugal concentrators. (10 kDa polyethersulfone membrane; Sartorius, Göttingen, Germany) at 1877×g. Protein concentration was determined using a Microplate BCA™ Protein Assay Kit (Thermo Fischer Scientific, Waltham, Mass., USA) in which bovine serum albumin was used as a protein standard.

Example 3

Pretreatment of Corn Stover

Corn stover was pretreated at the U.S. Department of Energy National Renewable Energy Laboratory (NREL) using dilute sulfuric acid. The following conditions were used for the pretreatment: 1.4 wt % sulfuric acid at 165° C. and 107 psi for 8 minutes. According to NREL, the water-insoluble solids in the pretreated corn stover (PCS) contained 56.5% cellulose, 4.6% hemicellulose and 28.4% lignin. Cellulose and hemicellulose were determined by a two-stage sulfuric acid hydrolysis with subsequent analysis of sugars by high performance liquid chromatography using NREL Standard Analytical Procedure #002. Lignin was determined gravimetrically after hydrolyzing the cellulose and hemicellulose fractions with sulfuric acid using NREL Standard Analytical Procedure #003. The PCS was washed with a large volume of DDI water on a glass filter.

Example 4

The Effect of Peroxidase on Hydrolysis of Pretreated Corn Stover (PCS) in the Presence and Absence of Cellobiose Dehydrogenase The effect of horseradish peroxidase (HRP) on hydrolysis of PCS was evaluated in the presence and absence of *Myceliophthora thermophila* CBS 117.65 cellobiose dehydrogenase (CDH).

The hydrolysis of PCS was performed using 2.2 ml deep-well plates (Axygen, Union City, Calif., USA) in a total reaction volume of 1.0 ml. The hydrolysis was performed with 50 mg of unwashed PCS per ml of 50 mM sodium acetate pH 5.0 buffer containing 1 mM manganese sulfate and a *Trichoderma reesei* cellulase composition (CELLUCLAST® supplemented with *Aspergillus oryzae* beta-glucosidase available from Novozymes A/S, Bagsvaerd, Denmark; the cellulase composition is designated herein in the Examples as "*Trichoderma reesei* cellulase composition") at 4 mg per g of PCS. Cellobiose dehydrogenase was added at concentrations between 0 and 10% (w/w) of total protein. The plate was then sealed using an ALPS-300™ plate heat sealer (Abgene, Epsom, United Kingdom), mixed thoroughly, and incubated at 50° C. for 72 hours with shaking at 150 rpm. All experiments were performed in triplicate.

At various time points between 24 and 72 hours of incubation, 100 µl aliquots were removed and the extent of hydrolysis was assayed by HPLC using the protocol described below. Cellobiose dehydrogenase-dependent cellulase inhibition was established, and then horseradish peroxidase was added to eliminate any peroxide produced. Horseradish peroxidase (Invitrogen, Carlsbad, Calif., USA) was added at final concentrations indicated in FIG. 1 from a stock solution of 1 unit per µl. One unit of horseradish peroxidase is defined as that quantity of enzyme necessary to form 1.0 mg of purpurogallin from pyrogallol in 20 seconds at pH 6.0 at 20° C. High concentrations of horseradish peroxidase were added to ensure sufficient peroxidase activity was present. No Amplex Red or other electron acceptor was added.

For HPLC analysis, samples were filtered with a 0.45 µm MULTISCREEN® 96-well filter plate (Millipore, Bedford, Mass., USA) and filtrates analyzed for sugar content as described below. When not used immediately, filtered aliquots were frozen at −20° C. The sugar concentrations of samples diluted in 0.005 M $H_2SO_4$ were measured using a 4.6×250 mm AMINEX® HPX-87H column (Bio-Rad Laboratories, Inc., Hercules, Calif., USA) by elution with 0.5% w/w benzoic acid-5 mM $H_2SO_4$ at a flow rate of 0.6 ml per minute at 65° C. for 11 minutes, and quantitation by integration of glucose and cellobiose signals from refractive index detection (CHEMSTATION®, AGILENT® 1100 HPLC, Agilent Technologies, Santa Clara, Calif., USA) calibrated by pure sugar samples. The resultant equivalents were used to calculate the percentage of cellulose conversion for each reaction. The extent of each hydrolysis was determined as the fraction of total cellulose converted to cellobiose+glucose, and were not corrected for soluble sugars present in PCS liquor.

All HPLC data processing was performed using Kaleidagraph software (Synergy software, Reading, Pa., USA). Measured sugar concentrations were adjusted for the appropriate dilution factor. Glucose and cellobiose were chromatographically separated and integrated and their respective concentrations determined independently. However, to calculate total conversion the glucose and cellobiose values were combined. Fractional hydrolysis was determined as the overall mass conversion to [glucose+cellobiose]/[total cellulose]. Triplicate data points were averaged and standard deviation was calculated.

The results (FIG. 1) demonstrated that increasing concentrations of *M. thermophila* cellobiose dehydrogenase led to reduced hydrolysis. Under these specific hydrolysis conditions, the addition of 10% cellobiose dehydrogenase resulted in approximately 5% loss of hydrolysis. At 4% cellobiose dehydrogenase, where the *Trichoderma reesei* cellulase composition was modestly inhibited, the extent of hydrolysis was completely restored at the lowest concentration of 1 unit of horseradish peroxidase per ml.

Example 5

The Effect of Horseradish Peroxidase on Hydrolysis of Pretreated Corn Stover (PCS)

The effect of horseradish peroxidase (HRP) on PCS hydrolysis by the *Trichoderma reesei* cellulase composition was determined in the absence of *Myceliophthora thermophila* CBS 117.65 cellobiose dehydrogenase.

The hydrolysis of PCS was conducted using 2.2 ml deep-well plates in a total reaction volume of 1.0 ml. The hydrolysis was performed with 50 mg of washed PCS per ml of 50 mM sodium acetate pH 5.0 buffer containing 1 mM manganese sulfate and the *Trichoderma reesei* cellulase composition at 4 mg per g of PCS. Horseradish peroxidase was added at 0-4 units per ml. The plate was then sealed using an ALPS-300™ plate heat sealer, mixed thoroughly, and incubated at 50° C. for 72 hours with shaking at 150 rpm. All experiments were performed in triplicate.

HPLC analysis of the extent of hydrolysis was performed according to the procedure described in Example 4.

Figure 2:
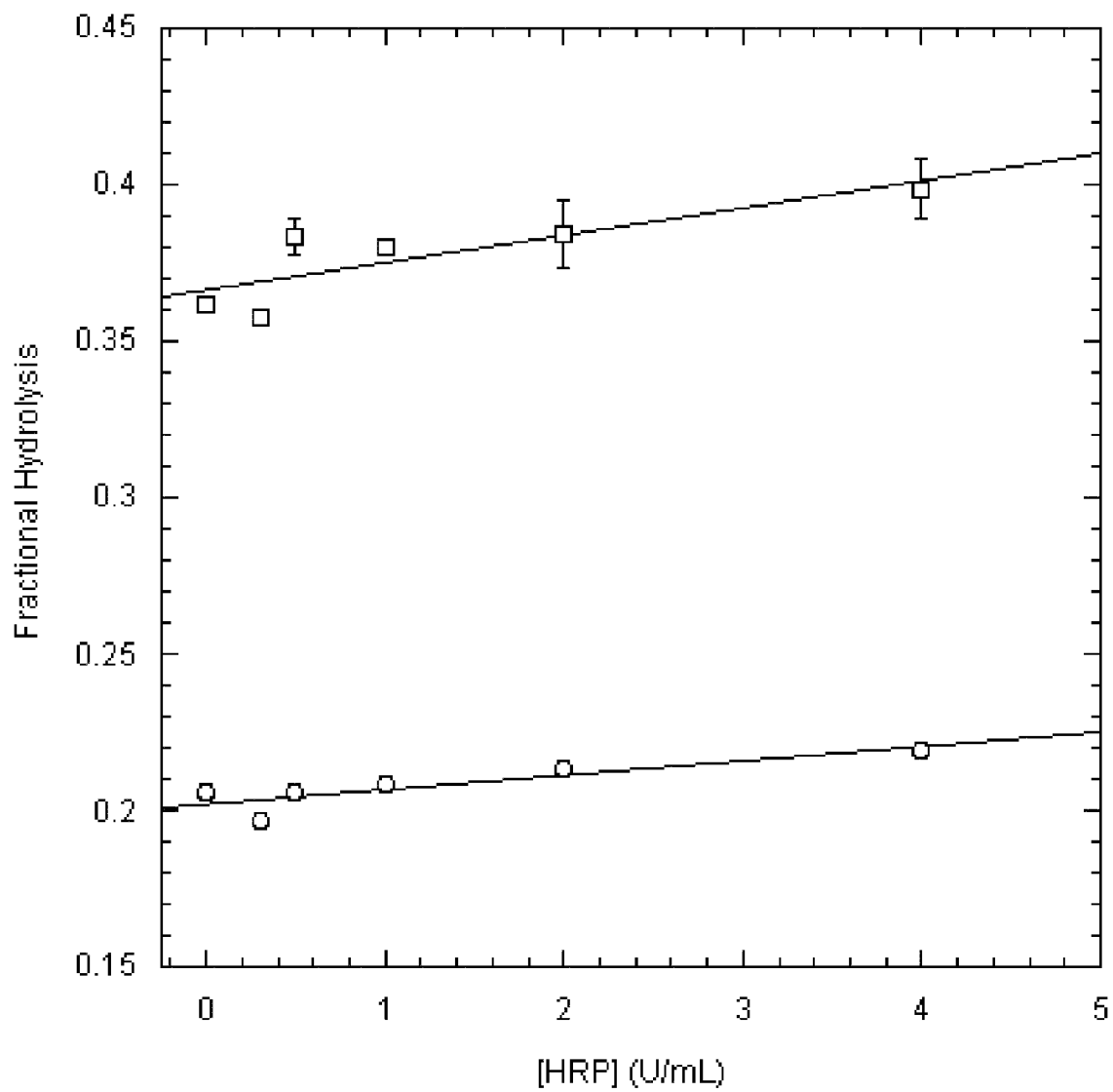
FIG. 2 shows horseradish peroxidase enhancement of PCS hydrolysis. Circles: 1 day of hydrolysis; squares: 3 days of hydrolysis.

The results (FIG. 2) demonstrated that the extent of hydrolysis increased linearly with horseradish peroxidase activity over the range of peroxidase activity tested, and the dependence of the extent of hydrolysis on horseradish peroxidase activity was approximately 2-fold higher at 3 days of incubation. Addition of horseradish peroxidase at 4 units per ml increased hydrolysis approximately 10% over reactions performed without horseradish peroxidase, both at day 1 and day 3 of hydrolysis.

Example 6

Preparation of *Coprinus cinereus* Peroxidase

*Coprinus cinereus* peroxidase was purified as described by WO 1992/016634, and Xu et al., 2003, "Fusion proteins containing *Coprinus cinereus* peroxidase and the cellulose-binding domain of *Humicola insolens* family 45 endoglucanase" in Application of Enzymes to Lignocellulosics (Mansfield, S. D. and Saddler, J. N. eds.) pp. 382-402, American Chemical Society, Washington, D.C. The purification scheme comprised ultrafiltration and anion-exchange chromatography. Cell-free broth of a *Coprinus cinereus* peroxidase (pH 7.7, 11 mS conductivity) was filtered with Whatman #2 paper and ultrafiltered with a polyethersulfone membrane (30 kD molecular weight cutoff). The washed and concentrated broth (pH 7.7, 1 mS) was then loaded onto a Q-SEPHAROSE BIG BEAD™ column pre-equilibrated with 5 mM $CaCl_2$-10 mM Tris-HCl pH 7.6 (Buffer A). The active fraction eluted by 5% Buffer B (Buffer A plus 2 M NaCl) was washed (with 5 mM $CaCl_2$) to 1 mS, then applied to a MONO-Q™ column (GE Healthcare, Piscataway, N.J., USA) equilibrated with Buffer A. Buffer B was used again for the elution. Fractions were analyzed for peroxidase activity and by SDS-PAGE. Specific peroxidase activity was assayed at 30° C. with 0.1 M sodium phosphate pH 7, 0.9 mM $H_2O_2$, and 1.7 mM 2,2'-azinobis(3-ethylbenzothiazoline-6-sulfonic acid) (ABTS), by monitoring the absorption increase at 418 nm. A stock concentration of 630 µM peroxidase was used.

Example 7

The Effect of Various Peroxidases on Hydrolysis of Pretreated Corn Stover (PCS)

The effect of various peroxidases on PCS hydrolysis by the *Trichoderma reesei* cellulase composition was determined. The peroxidases included manganese peroxidase (Sigma Chemical Co., St. Louis, Mo., USA), bovine milk lactoperoxidase (Sigma Chemical Co., St. Louis, Mo., USA), lignin peroxidase (Sigma Chemical Co., St. Louis, Mo., USA), and *Coprinus cinereus* peroxidase (Example 6). One unit of manganese peroxidase is defined as the amount of enzyme necessary to oxidize 1 µmole of $Mn^{2+}$ per minute to $Mn^{3+}$ at pH 4.5 and 25° C. One unit of lactoperoxidase is defined as that quantity of enzyme necessary to form 1.0 mg of purpurogallin from pyrogallol in 20 seconds at pH 6.0 and 20° C. One unit of lignin peroxidase is defined as the amount of enzyme necessary to oxidize 1 µmole 3.4-dimethoxybenzyl alcohol per minute at pH 3.0 and 30° C. One unit of *Coprinus cinereus* peroxidase is defined as the quantity of enzyme necessary to consume 1 µmole of $H_2O_2$ per minute.

Figure 3:
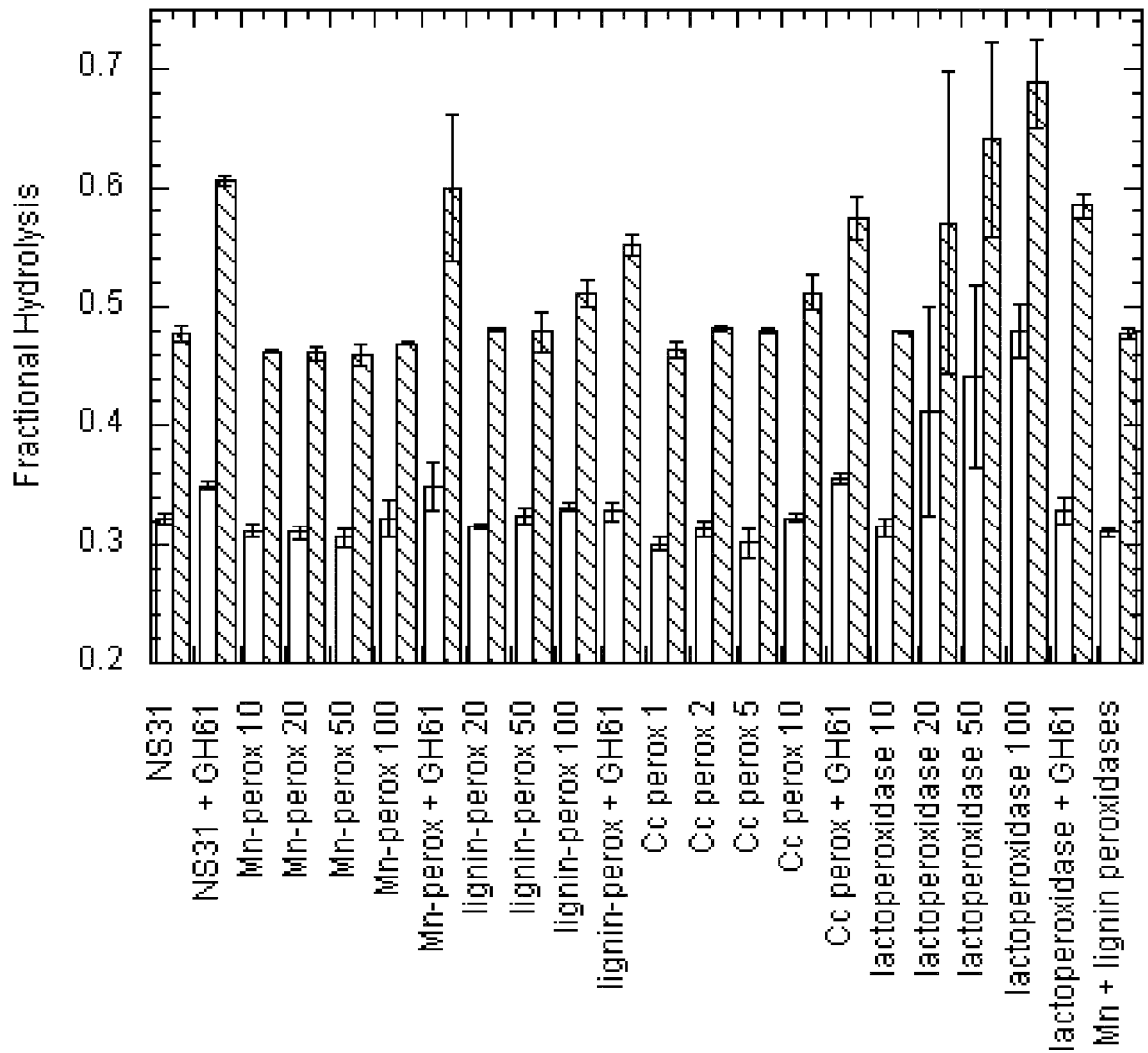
FIG. 3 shows the effect of various peroxidases on PCS hydrolysis. Solid bars: 1 day of hydrolysis; hatched bars: 3 days of hydrolysis. Numbers indicate the volumes of the stock peroxidases added, as indicated in the text. Mn-perox: manganese peroxidase; lignin-perox: lignin-peroxidase; and cellulase: *Trichoderma reesei* cellulase composition.

The hydrolysis of PCS was conducted using 2.2 ml deep-well plates in a total reaction volume of 1.0 ml. The hydrolysis was performed with 50 mg of washed PCS per ml of 50 mM sodium acetate pH 5.0 containing 1 mM manganese sulfate and the *Trichoderma reesei* cellulase composition at 4 mg per g of PCS. Manganese peroxidase, lactoperoxidase, lignin peroxidase, and *Coprinus cinereus* peroxidase were added at volumes of 0-100 µl, to give the final concentrations indicated in FIG. 3, from the following stock solutions: Mn peroxidase: 0.005 unit per µl, 50 µg per µl; lignin peroxidase: 0.04 unit per µl, 20 µg per µl; lactoperoxidase: 0.2 unit per µl, 5 µg per µl; and *Coprinus cinereus* peroxidase: 630 µM. The plate was then sealed using an ALPS-300™ plate heat sealer, mixed thoroughly, and incubated at 50° C. for 72 hours with shaking at 150 rpm. All experiments were performed in triplicate.

HPLC analysis of the extent of hydrolysis was performed according to the procedure described in Example 5.

The results (FIG. 3) demonstrated that each of the peroxidases, with the exception of manganese peroxidase, enhanced PCS hydrolysis in a concentration-dependent manner. The effect did not saturate under the concentrations utilized.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

```
<160> NUMBER OF SEQ ID NOS: 70

<210> SEQ ID NO 1
```

```
<211> LENGTH: 1846
<212> TYPE: DNA
<213> ORGANISM: Thielavia terrestris

<400> SEQUENCE: 1
aattgaagga gggagtggcg gagtggccac caagtcaggc ggctgtcaac taaccaagga      60
tgggaacagt tcggctcgcc ttgcccgagg gcagcgttcc ctgatgggga cgaaccatgg     120
gactggggtc agctgctgta taaaagttca aatcgatgat ctctcagatg cgctgctgg     180
ggtgttctgc gcttttccat cctcgcaacc tggtatccca ctagtccagc gttcggcacc     240
atgaagtcgt tcaccattgc cgccttggca gccctatggg cccaggaggc cgccgcccac     300
gcgaccttcc aggacctctg gattgatgga gtcgactacg gctcgcaatg tgtccgcctc     360
ccggcgtcca actcccccgt caccaatgtt cgtccgacg atatccgatg caatgtcggc     420
acctcgaggc ccaccgtcaa gtcccggtc aaggccggct ccacggtcac gatcgagatg     480
caccaggttc gcacgcctct ctgcgtaggc cccccagcta ctatatggca ctaacacgac     540
ctccagcaac ctggcgaccg tcttgcgcc aacgaggcta tcggcggcga ccactacggc     600
cccgtaatgg tgtacatgtc caaggtcgat gacgcggtga cagccgacgg ttcatcgggc     660
tggttcaagg tgttccagga cagctgggcc aagaacccgt cgggttcgac gggcgacgac     720
gactactggg gcaccaagga cctcaactcg tgctgcggca agatgaacgt caagatcccc     780
gaagacatcg agccgggcga ctacctgctc cgcgccgagg ttatcgcgct gcacgtggcc     840
gccagctcgg gcggcgcgca gttctacatg tcctgctacc agctgaccgt gacgggctcc     900
ggcagcgcca ccccctcgac cgtgaatttc ccgggcgcct actcggccag cgacccgggc     960
atcctgatca acatccacgc gcccatgtcg acctacgtcg tccccgggccc gaccgtgtac    1020
gcgggcggct cgaccaagtc ggctggcagc tcctgctccg gctgcgaggc gacctgcacg    1080
gttggttccg gccccagcgc gacactgacg cagcccacct ccaccgcgac cgcgacctcc    1140
gcccctggcg gcggcggctc cggctgcacg gcggccaagt accagcagtg cggcggcacc    1200
ggctacactg ggtgcaccac ctgcgctgta agttccctcg tgatatgcag cggaacaccg    1260
tctggactgt tttgctaact cgcgtcgtag tccgggtcta cctgcagcgc cgtctcgcct    1320
ccgtactact cgcagtgcct ctaagccggg agcgcttgct cagcgggctg ctgtgaagga    1380
gctccatgtc cccatgccgc catggccgga gtacccgggct gagcgcccaa ttcttgtata    1440
tagttgagtt ttcccaatca tgaatacata tgcatctgca tggactgttg cgtcgtcagt    1500
ctacatcctt tgctccactg aactgtgaga ccccatgtca tccggaccat tcgatcggtg    1560
ctcgctctac catctcggtt gatgggtctg ggcttgagag tcactggcac gtcctcggcg    1620
gtaatgaaat gtggaggaaa gtgtgagctg tctgacgcac tcggcgctga tgagacgttg    1680
agcgcggccc acactggtgt tctgtaagcc agcacacaaa agaatactcc aggatggccc    1740
atagcggcaa atatacagta tcagggatgc aaaaagtgca aaagtaaggg gctcaatcgg    1800
ggatcgaacc cgagacctcg cacatgactt atttcaagtc agggt                    1846

<210> SEQ ID NO 2
<211> LENGTH: 326
<212> TYPE: PRT
<213> ORGANISM: Thielavia terrestris

<400> SEQUENCE: 2

Met Lys Ser Phe Thr Ile Ala Ala Leu Ala Ala Leu Trp Ala Gln Glu
1               5                   10                  15
```

Ala Ala Ala His Ala Thr Phe Gln Asp Leu Trp Ile Asp Gly Val Asp
            20                  25                  30

Tyr Gly Ser Gln Cys Val Arg Leu Pro Ala Ser Asn Ser Pro Val Thr
        35                  40                  45

Asn Val Ala Ser Asp Asp Ile Arg Cys Asn Val Gly Thr Ser Arg Pro
    50                  55                  60

Thr Val Lys Cys Pro Val Lys Ala Gly Ser Thr Val Thr Ile Glu Met
65                  70                  75                  80

His Gln Gln Pro Gly Asp Arg Ser Cys Ala Asn Glu Ala Ile Gly Gly
                85                  90                  95

Asp His Tyr Gly Pro Val Met Val Tyr Met Ser Lys Val Asp Asp Ala
            100                 105                 110

Val Thr Ala Asp Gly Ser Ser Gly Trp Phe Lys Val Phe Gln Asp Ser
        115                 120                 125

Trp Ala Lys Asn Pro Ser Gly Ser Thr Gly Asp Asp Tyr Trp Gly
    130                 135                 140

Thr Lys Asp Leu Asn Ser Cys Cys Gly Lys Met Asn Val Lys Ile Pro
145                 150                 155                 160

Glu Asp Ile Glu Pro Gly Asp Tyr Leu Leu Arg Ala Glu Val Ile Ala
                165                 170                 175

Leu His Val Ala Ala Ser Ser Gly Gly Ala Gln Phe Tyr Met Ser Cys
            180                 185                 190

Tyr Gln Leu Thr Val Thr Gly Ser Gly Ser Ala Thr Pro Ser Thr Val
        195                 200                 205

Asn Phe Pro Gly Ala Tyr Ser Ala Ser Asp Pro Gly Ile Leu Ile Asn
    210                 215                 220

Ile His Ala Pro Met Ser Thr Tyr Val Val Pro Gly Pro Thr Val Tyr
225                 230                 235                 240

Ala Gly Gly Ser Thr Lys Ser Ala Gly Ser Ser Cys Ser Gly Cys Glu
                245                 250                 255

Ala Thr Cys Thr Val Gly Ser Gly Pro Ser Ala Thr Leu Thr Gln Pro
            260                 265                 270

Thr Ser Thr Ala Thr Ala Thr Ser Ala Pro Gly Gly Gly Ser Gly
        275                 280                 285

Cys Thr Ala Ala Lys Tyr Gln Gln Cys Gly Gly Thr Gly Tyr Thr Gly
    290                 295                 300

Cys Thr Thr Cys Ala Ser Gly Ser Thr Cys Ser Ala Val Ser Pro Pro
305                 310                 315                 320

Tyr Tyr Ser Gln Cys Leu
                325

<210> SEQ ID NO 3
<211> LENGTH: 880
<212> TYPE: DNA
<213> ORGANISM: Thielavia terrestris

<400> SEQUENCE: 3
accccgggat cactgcccct aggaaccagc acacctcggt ccaatcatgc ggttcgacgc    60
cctctccgcc ctcgctcttg cgccgcttgt ggctggccac ggcgccgtga ccagctacat   120
catcggcggc aaaacctatc ccggctacga gggcttctcg cctgcctcga gcccgccgac   180
gatccagtac cagtggcccg actacaaccc gaccctgagc gtgaccgacc cgaagatgcg   240
ctgcaacggc ggcacctcgg cagagctcag cgcgcccgtc caggccggcg agaacgtgac   300
ggccgtctgg aagcagtgga cccaccagca aggccccgtc atggtctgga tgttcaagtg   360

```
ccccggcgac ttctcgtcgt gccacggcga cggcaagggc tggttcaaga tcgaccagct    420
gggcctgtgg ggcaacaacc tcaactcgaa caactgggc accgcgatcg tctacaagac     480
cctccagtgg agcaacccga tccccaagaa cctcgcgccg ggcaactacc tcatccgcca    540
cgagctgctc gccctgcacc aggccaacac gccgcagttc tacgccgagt gcgcccagct    600
ggtcgtctcc ggcagcggct ccgccctgcc ccgtccgac  tacctctaca gcatccccgt    660
ctacgcgccc cagaacgacc ccggcatcac cgtgagtggg cttccgttcc gcggcgagct    720
ctgtggaaat cttgctgacg atgggctagg ttgacatcta caacggcggg cttacctcct    780
acaccccgcc cggcggcccc gtctggtctg gcttcgagtt ttaggcgcat tgagtcgggg    840
gctacgaggg gaaggcatct gttcgcatga gcgtgggtac                          880
```

<210> SEQ ID NO 4
<211> LENGTH: 239
<212> TYPE: PRT
<213> ORGANISM: Thielavia terrestris

<400> SEQUENCE: 4

```
Met Arg Phe Asp Ala Leu Ser Ala Leu Ala Leu Ala Pro Leu Val Ala
1               5                   10                  15

Gly His Gly Ala Val Thr Ser Tyr Ile Ile Gly Gly Lys Thr Tyr Pro
            20                  25                  30

Gly Tyr Glu Gly Phe Ser Pro Ala Ser Ser Pro Thr Ile Gln Tyr
        35                  40                  45

Gln Trp Pro Asp Tyr Asn Pro Thr Leu Ser Val Thr Asp Pro Lys Met
50                  55                  60

Arg Cys Asn Gly Gly Thr Ser Ala Glu Leu Ser Ala Pro Val Gln Ala
65                  70                  75                  80

Gly Glu Asn Val Thr Ala Val Trp Lys Gln Trp Thr His Gln Gln Gly
                85                  90                  95

Pro Val Met Val Trp Met Phe Lys Cys Pro Gly Asp Phe Ser Ser Ser
            100                 105                 110

His Gly Asp Gly Lys Gly Trp Phe Lys Ile Asp Gln Leu Gly Leu Trp
        115                 120                 125

Gly Asn Asn Leu Asn Ser Asn Asn Trp Gly Thr Ala Ile Val Tyr Lys
130                 135                 140

Thr Leu Gln Trp Ser Asn Pro Ile Pro Lys Asn Leu Ala Pro Gly Asn
145                 150                 155                 160

Tyr Leu Ile Arg His Glu Leu Leu Ala Leu His Gln Ala Asn Thr Pro
                165                 170                 175

Gln Phe Tyr Ala Glu Cys Ala Gln Leu Val Val Ser Gly Ser Gly Ser
            180                 185                 190

Ala Leu Pro Pro Ser Asp Tyr Leu Tyr Ser Ile Pro Val Tyr Ala Pro
        195                 200                 205

Gln Asn Asp Pro Gly Ile Thr Val Asp Ile Tyr Asn Gly Gly Leu Thr
210                 215                 220

Ser Tyr Thr Pro Pro Gly Gly Pro Val Trp Ser Gly Phe Glu Phe
225                 230                 235
```

<210> SEQ ID NO 5
<211> LENGTH: 1000
<212> TYPE: DNA
<213> ORGANISM: Thielavia terrestris

<400> SEQUENCE: 5

```
ctcctgttcc tgggccaccg cttgttgcct gcactattgg tagagttggt ctattgctag      60
agttggccat gcttctcaca tcagtcctcg gctcggctgc cctgcttgct agcggcgctg     120
cggcacacgg cgccgtgacc agctacatca tcgccggcaa gaattacccg gggtgggtag     180
ctgattattg agggcgcatt caaggttcat accggtgtgc atggctgaca accggctggc     240
agataccaag gcttttctcc tgcgaactcg ccgaacgtca tccaatggca atggcatgac     300
tacaaccccg tcttgtcgtg cagcgactcg aagcttcgct gcaacggcgg cacgtcggcc     360
accctgaacg ccacggccgc accgggcgac accatcaccg ccatctgggc gcagtggacg     420
cacagccagg gccccatcct ggtgtggatg tacaagtgcc cgggctcctt cagctcctgt     480
gacggctccg gcgctggctg gttcaagatc gacgaggccg gcttccacgg cgacggcgtc     540
aaggtcttcc tcgacaccga gaacccgtcc ggctgggaca tcgccaagct cgtcggcggc     600
aacaagcagt ggagcagcaa ggtccccgag ggcctcgccc ccggcaacta cctcgtccgc     660
cacgagttga tcgccctgca ccaggccaac aacccgcagt tctacccgga gtgcgcccag     720
gtcgtcatca ccggctccgg caccgcgcag ccggatgcct catacaaggc ggctatcccc     780
ggctactgca accagaatga cccgaacatc aaggtgagat ccaggcgtaa tgcagtctac     840
tgctggaaag aaagtggtcc aagctaaacc gcgctccagg tgcccatcaa cgaccactcc     900
atccctcaga cctacaagat tcccggcccc ccgtcttca agggcaccgc cagcaagaag     960
gcccgggact tcaccgcctg aagttgttga atcgatggag                          1000

<210> SEQ ID NO 6
<211> LENGTH: 258
<212> TYPE: PRT
<213> ORGANISM: Thielavia terrestris

<400> SEQUENCE: 6

Met Leu Leu Thr Ser Val Leu Gly Ser Ala Ala Leu Leu Ala Ser Gly
1               5                   10                  15

Ala Ala Ala His Gly Ala Val Thr Ser Tyr Ile Ile Ala Gly Lys Asn
                20                  25                  30

Tyr Pro Gly Tyr Gln Gly Phe Ser Pro Ala Asn Ser Pro Asn Val Ile
            35                  40                  45

Gln Trp Gln Trp His Asp Tyr Asn Pro Val Leu Ser Cys Ser Asp Ser
        50                  55                  60

Lys Leu Arg Cys Asn Gly Gly Thr Ser Ala Thr Leu Asn Ala Thr Ala
65                  70                  75                  80

Ala Pro Gly Asp Thr Ile Thr Ala Ile Trp Ala Gln Trp Thr His Ser
                85                  90                  95

Gln Gly Pro Ile Leu Val Trp Met Tyr Lys Cys Pro Gly Ser Phe Ser
            100                 105                 110

Ser Cys Asp Gly Ser Gly Ala Gly Trp Phe Lys Ile Asp Glu Ala Gly
        115                 120                 125

Phe His Gly Asp Gly Val Lys Val Phe Leu Asp Thr Glu Asn Pro Ser
    130                 135                 140

Gly Trp Asp Ile Ala Lys Leu Val Gly Gly Asn Lys Gln Trp Ser Ser
145                 150                 155                 160

Lys Val Pro Glu Gly Leu Ala Pro Gly Asn Tyr Leu Val Arg His Glu
                165                 170                 175

Leu Ile Ala Leu His Gln Ala Asn Asn Pro Gln Phe Tyr Pro Glu Cys
            180                 185                 190
```

```
Ala Gln Val Val Ile Thr Gly Ser Gly Thr Ala Gln Pro Asp Ala Ser
            195                 200                 205

Tyr Lys Ala Ala Ile Pro Gly Tyr Cys Asn Gln Asn Asp Pro Asn Ile
210                 215                 220

Lys Val Pro Ile Asn Asp His Ser Ile Pro Gln Thr Tyr Lys Ile Pro
225                 230                 235                 240

Gly Pro Pro Val Phe Lys Gly Thr Ala Ser Lys Lys Ala Arg Asp Phe
                245                 250                 255

Thr Ala

<210> SEQ ID NO 7
<211> LENGTH: 681
<212> TYPE: DNA
<213> ORGANISM: Thielavia terrestris

<400> SEQUENCE: 7
atgctcgcaa acggtgccat cgtcttcctg gccgccgccc tcggcgtcag tggccactac      60
acctggccac gggttaacga cggcgccgac tggcaacagg tccgtaaggc ggacaactgg     120
caggacaacg gctacgtcgg ggatgtcacg tcgccacaga tccgctgttt ccaggcgacc     180
ccgtccccgg cccatccgt cctcaacacc acggccggct cgaccgtgac ctactgggcc      240
aaccccgacg tctaccaccc cgggcctgtg cagttttaca tggcccgcgt gcccgatggc     300
gaggacatca actcgtggaa cggcgacggc gccgtgtggt tcaaggtgta cgaggaccat     360
cctacctttg gcgctcagct cacatggccc agcacgggca agagctcgtt cgcggttccc     420 atcccccgt gcatcaagtc cggctactac ctcctccggg cggagcaaat cggcctgcac      480
gtcgcccaga gcgtaggcgg agcgcagttc tacatctcat gcgcccagct cagcgtcacc     540
ggcggcggca gcaccgagcc gccgaacaag gtggccttcc ccggcgctta cagtgcgacg     600
gacccgggca ttctgatcaa catctactac cctgttccca cgtcctacca gaaccccggc     660
ccggccgtct tcagctgctg a                                               681

<210> SEQ ID NO 8
<211> LENGTH: 226
<212> TYPE: PRT
<213> ORGANISM: Thielavia terrestris

<400> SEQUENCE: 8

Met Leu Ala Asn Gly Ala Ile Val Phe Leu Ala Ala Ala Leu Gly Val
1               5                   10                  15

Ser Gly His Tyr Thr Trp Pro Arg Val Asn Asp Gly Ala Asp Trp Gln
            20                  25                  30

Gln Val Arg Lys Ala Asp Asn Trp Gln Asp Asn Gly Tyr Val Gly Asp
        35                  40                  45

Val Thr Ser Pro Gln Ile Arg Cys Phe Gln Ala Thr Pro Ser Pro Ala
    50                  55                  60

Pro Ser Val Leu Asn Thr Thr Ala Gly Ser Thr Val Thr Tyr Trp Ala
65                  70                  75                  80

Asn Pro Asp Val Tyr His Pro Gly Pro Val Gln Phe Tyr Met Ala Arg
                85                  90                  95

Val Pro Asp Gly Glu Asp Ile Asn Ser Trp Asn Gly Asp Gly Ala Val
            100                 105                 110

Trp Phe Lys Val Tyr Glu Asp His Pro Thr Phe Gly Ala Gln Leu Thr
        115                 120                 125

Trp Pro Ser Thr Gly Lys Ser Ser Phe Ala Val Pro Ile Pro Pro Cys
```

Ile Lys Ser Gly Tyr Tyr Leu Leu Arg Ala Glu Gln Ile Gly Leu His
145                 150                 155                 160

Val Ala Gln Ser Val Gly Gly Ala Gln Phe Tyr Ile Ser Cys Ala Gln
                165                 170                 175

Leu Ser Val Thr Gly Gly Ser Thr Glu Pro Pro Asn Lys Val Ala
            180                 185                 190

Phe Pro Gly Ala Tyr Ser Ala Thr Asp Pro Gly Ile Leu Ile Asn Ile
        195                 200                 205

Tyr Tyr Pro Val Pro Thr Ser Tyr Gln Asn Pro Gly Pro Ala Val Phe
    210                 215                 220

Ser Cys
225

<210> SEQ ID NO 9
<211> LENGTH: 960
<212> TYPE: DNA
<213> ORGANISM: Thielavia terrestris

<400> SEQUENCE: 9
atgaagggac ttttcagtgc cgccgccctc tccctggccg tcggccaggc ttcggcccat      60
tacatcttcc agcaactctc catcaacggg aaccagtttc cggtgtacca atatattcgc     120
aagaacacca attataacag tcccgttacc gatctcacgt ccgacgatct tcggtgcaat     180
gtcggcgccc agggtgctgg gacagacacc gtcacggtga aggccggcga ccagttcacc     240
ttcacccttg acacccctgt ttaccaccag gggcccatct ccatctacat gtccaaggcc     300
ccgggcgcgg cgtcagacta cgatggcagc ggcggctggt tcaagatcaa ggactgggc      360 ccgacttttca cgccgacgg cacggccacc tgggacatgg ccggctcata cacctacaac     420
atcccgacct gcattcccga cggcgactat ctgctccgca tccagtcgct ggccatccac     480 aaccctggc cggcgggcat cccgcagttc tacatctcct cgcccagat caccgtgacc      540 ggcggcggca acggcaaccc tggcccgacg ccctcatcc ccggcgcctt caaggacacc      600
gacccgggct acacggtgaa catctacacg aacttccaca actacacggt tcccggcccg     660
gaggtcttca gctgcaacgg cggcggctcg aacccgcccc gccggtgag tagcagcacg     720 cccgcgacca cgacgctggt cacgtcgacg cgcaccacgt cctccacgtc ctccgcctcg     780
acgccggcct cgaccggcgg ctgcaccgtc gccaagtggg gccagtgcgg cggcaacggg     840
tacaccggct gcacgacctg cgcggccggg tccacctgca gcaagcagaa cgactactac     900
tcgcagtgct tgtaagggag gccgcaaagc atgaggtgtt tgaagaggag gagaggggtc     960

<210> SEQ ID NO 10
<211> LENGTH: 304
<212> TYPE: PRT
<213> ORGANISM: Thielavia terrestris

<400> SEQUENCE: 10

Met Lys Gly Leu Phe Ser Ala Ala Ala Leu Ser Leu Ala Val Gly Gln
1               5                   10                  15

Ala Ser Ala His Tyr Ile Phe Gln Gln Leu Ser Ile Asn Gly Asn Gln
                20                  25                  30

Phe Pro Val Tyr Gln Tyr Ile Arg Lys Asn Thr Asn Tyr Asn Ser Pro
            35                  40                  45

Val Thr Asp Leu Thr Ser Asp Asp Leu Arg Cys Asn Val Gly Ala Gln
        50                  55                  60

```
Gly Ala Gly Thr Asp Thr Val Thr Val Lys Ala Gly Asp Gln Phe Thr
 65                  70                  75                  80

Phe Thr Leu Asp Thr Pro Val Tyr His Gln Gly Pro Ile Ser Ile Tyr
             85                  90                  95

Met Ser Lys Ala Pro Gly Ala Ser Asp Tyr Asp Gly Ser Gly Gly
        100                 105                 110

Trp Phe Lys Ile Lys Asp Trp Gly Pro Thr Phe Asn Ala Asp Gly Thr
        115                 120                 125

Ala Thr Trp Asp Met Ala Gly Ser Tyr Thr Tyr Asn Ile Pro Thr Cys
130                 135                 140

Ile Pro Asp Gly Asp Tyr Leu Leu Arg Ile Gln Ser Leu Ala Ile His
145                 150                 155                 160

Asn Pro Trp Pro Ala Gly Ile Pro Gln Phe Tyr Ile Ser Cys Ala Gln
                165                 170                 175

Ile Thr Val Thr Gly Gly Gly Asn Gly Asn Pro Gly Pro Thr Ala Leu
            180                 185                 190

Ile Pro Gly Ala Phe Lys Asp Thr Asp Pro Gly Tyr Thr Val Asn Ile
        195                 200                 205

Tyr Thr Asn Phe His Asn Tyr Thr Val Pro Gly Pro Glu Val Phe Ser
210                 215                 220

Cys Asn Gly Gly Ser Asn Pro Pro Pro Val Ser Ser Ser Thr
225                 230                 235                 240

Pro Ala Thr Thr Thr Leu Val Thr Ser Thr Arg Thr Thr Ser Ser Thr
                245                 250                 255

Ser Ser Ala Ser Thr Pro Ala Ser Thr Gly Gly Cys Thr Val Ala Lys
            260                 265                 270

Trp Gly Gln Cys Gly Gly Asn Gly Tyr Thr Gly Cys Thr Thr Cys Ala
        275                 280                 285

Ala Gly Ser Thr Cys Ser Lys Gln Asn Asp Tyr Tyr Ser Gln Cys Leu
        290                 295                 300

<210> SEQ ID NO 11
<211> LENGTH: 954
<212> TYPE: DNA
<213> ORGANISM: Thielavia terrestris

<400> SEQUENCE: 11
atgaagggcc tcagcctcct cgccgctgcg tcggcagcga ctgctcatac catcttcgtg      60
cagctcgagt caggggggaac gacctatccg gtatcctacg gcatccggga ccctagctac     120
gacggtccca tcaccgacgt cacctccgac tcactggctt gcaatggtcc cccgaacccc     180
acgacgccgt ccccgtacat catcaacgtc accgccggca ccacggtcgc ggcgatctgg     240
aggcacaccc tcacatccgg ccccgacgat gtcatggacg ccagccacaa ggggccgacc     300
ctggcctacc tcaagaaggt cgatgatgcc ttgaccgaca cgggtatcgg cggcggctgg     360
ttcaagatcc aggaggccgg ttacgacaat ggcaattggg ctaccagcac ggtgatcacc     420
aacggtggct ccaatatat tgacatcccc gcctgcattc ccaacggcca gtatctgctc     480
cgcgccgaga tgatcgcgct ccacgccgcc agcacgcagg tggtgcccca gctctacatg     540
gagtgcgcgc agatcaacgt ggtgggcggc tccggcagcg ccagcccgca gacgtacagc     600
atcccgggca tctaccaggc aaccgacccg ggcctgctga tcaacatcta ctccatgacg     660
ccgtccagcc agtacaccat tccgggtccg ccctgttca cctgcagcgg cagcggcaac     720
aacggcggcg gcagcaaccc gtcgggcggg cagaccacga cggcgaagcc cacgacgacg     780
```

-continued

```
acggcggcga cgaccacctc ctccgccgct cctaccagca gccagggggg cagcagcggt    840
tgcaccgttc cccagtggca gcagtgcggt ggcatctcgt tcaccggctg caccacctgc    900
gcggcgggct acacctgcaa gtatctgaac gactattact cgcaatgcca gtaa          954
```

<210> SEQ ID NO 12
<211> LENGTH: 317
<212> TYPE: PRT
<213> ORGANISM: Thielavia terrestris

<400> SEQUENCE: 12

```
Met Lys Gly Leu Ser Leu Leu Ala Ala Ser Ala Ala Thr Ala His
1               5                   10                  15

Thr Ile Phe Val Gln Leu Glu Ser Gly Gly Thr Thr Tyr Pro Val Ser
            20                  25                  30

Tyr Gly Ile Arg Asp Pro Ser Tyr Asp Gly Pro Ile Thr Asp Val Thr
        35                  40                  45

Ser Asp Ser Leu Ala Cys Asn Gly Pro Pro Asn Pro Thr Thr Pro Ser
    50                  55                  60

Pro Tyr Ile Ile Asn Val Thr Ala Gly Thr Thr Val Ala Ala Ile Trp
65                  70                  75                  80

Arg His Thr Leu Thr Ser Gly Pro Asp Asp Val Met Asp Ala Ser His
                85                  90                  95

Lys Gly Pro Thr Leu Ala Tyr Leu Lys Lys Val Asp Asp Ala Leu Thr
            100                 105                 110

Asp Thr Gly Ile Gly Gly Gly Trp Phe Lys Ile Gln Glu Ala Gly Tyr
        115                 120                 125

Asp Asn Gly Asn Trp Ala Thr Ser Thr Val Ile Thr Asn Gly Gly Phe
    130                 135                 140

Gln Tyr Ile Asp Ile Pro Ala Cys Ile Pro Asn Gly Gln Tyr Leu Leu
145                 150                 155                 160

Arg Ala Glu Met Ile Ala Leu His Ala Ala Ser Thr Gln Gly Gly Ala
                165                 170                 175

Gln Leu Tyr Met Glu Cys Ala Gln Ile Asn Val Val Gly Gly Ser Gly
            180                 185                 190

Ser Ala Ser Pro Gln Thr Tyr Ser Ile Pro Gly Ile Tyr Gln Ala Thr
        195                 200                 205

Asp Pro Gly Leu Leu Ile Asn Ile Tyr Ser Met Thr Pro Ser Ser Gln
    210                 215                 220

Tyr Thr Ile Pro Gly Pro Pro Leu Phe Thr Cys Ser Gly Ser Gly Asn
225                 230                 235                 240

Asn Gly Gly Gly Ser Asn Pro Ser Gly Gly Gln Thr Thr Ala Lys
                245                 250                 255

Pro Thr Thr Thr Thr Ala Ala Thr Thr Thr Ser Ser Ala Ala Pro Thr
            260                 265                 270

Ser Ser Gln Gly Gly Ser Ser Gly Cys Thr Val Pro Gln Trp Gln Gln
        275                 280                 285

Cys Gly Gly Ile Ser Phe Thr Gly Cys Thr Thr Cys Ala Ala Gly Tyr
    290                 295                 300

Thr Cys Lys Tyr Leu Asn Asp Tyr Tyr Ser Gln Cys Gln
305                 310                 315
```

<210> SEQ ID NO 13
<211> LENGTH: 799
<212> TYPE: DNA

<213> ORGANISM: Thermoascus aurantiacus

<400> SEQUENCE: 13

```
atgtccttttt ccaagataat tgctactgcc ggcgttcttg cctctgcttc tctagtggct    60
ggccatggct tcgttcagaa catcgtgatt gatggtaaaa agtatgtcat tgcaagacgc   120
acataagcgg caacagctga caatcgacag ttatggcggg tatctagtga accagtatcc   180
atacatgtcc aatcctccag aggtcatcgc ctggtctact acggcaactg atcttggatt   240
tgtggacggt actggatacc aaaccccaga tatcatctgc cataggggcg ccaagcctgg   300
agccctgact gctccagtct tccaggagg aactgttgag cttcaatgga ctccatggcc   360
tgattctcac catggcccag ttatcaacta ccttgctccg tgcaatggtg attgttccac   420
tgtggataag acccaattag aattcttcaa aattgccgag agcggtctca tcaatgatga   480
caatcctcct gggatctggg cttcagacaa tctgatagca gccaacaaca gctggactgt   540
caccattcca accacaattg cacctggaaa ctatgttctg aggcatgaga ttattgctct   600
tcactcagct cagaaccagg atggtgccca gaactatccc cagtgcatca atctgcaggt   660
cactggaggt ggttctgata cccctgctgg aactcttgga acggcactct accacgatac   720
cgatcctgga attctgatca acatctatca gaaactttcc agctatatca tccctggtcc   780
tcctctgtat actggttaa                                                799
```

<210> SEQ ID NO 14
<211> LENGTH: 250
<212> TYPE: PRT
<213> ORGANISM: Thermoascus aurantiacus

<400> SEQUENCE: 14

```
Met Ser Phe Ser Lys Ile Ile Ala Thr Ala Gly Val Leu Ala Ser Ala
1               5                   10                  15

Ser Leu Val Ala Gly His Gly Phe Val Gln Asn Ile Val Ile Asp Gly
            20                  25                  30

Lys Lys Tyr Tyr Gly Gly Tyr Leu Val Asn Gln Tyr Pro Tyr Met Ser
        35                  40                  45

Asn Pro Pro Glu Val Ile Ala Trp Ser Thr Thr Ala Thr Asp Leu Gly
    50                  55                  60

Phe Val Asp Gly Thr Gly Tyr Gln Thr Pro Asp Ile Ile Cys His Arg
65                  70                  75                  80

Gly Ala Lys Pro Gly Ala Leu Thr Ala Pro Val Ser Pro Gly Thr
                85                  90                  95

Val Glu Leu Gln Trp Thr Pro Trp Pro Asp Ser His His Gly Pro Val
            100                 105                 110

Ile Asn Tyr Leu Ala Pro Cys Asn Gly Asp Cys Ser Thr Val Asp Lys
        115                 120                 125

Thr Gln Leu Glu Phe Phe Lys Ile Ala Glu Ser Gly Leu Ile Asn Asp
    130                 135                 140

Asp Asn Pro Pro Gly Ile Trp Ala Ser Asp Asn Leu Ile Ala Ala Asn
145                 150                 155                 160

Asn Ser Trp Thr Val Thr Ile Pro Thr Thr Ile Ala Pro Gly Asn Tyr
                165                 170                 175

Val Leu Arg His Glu Ile Ile Ala Leu His Ser Ala Gln Asn Gln Asp
            180                 185                 190

Gly Ala Gln Asn Tyr Pro Gln Cys Ile Asn Leu Gln Val Thr Gly Gly
        195                 200                 205
```

Gly Ser Asp Asn Pro Ala Gly Thr Leu Gly Thr Ala Leu Tyr His Asp
          210                 215                 220

Thr Asp Pro Gly Ile Leu Ile Asn Ile Tyr Gln Lys Leu Ser Ser Tyr
225                 230                 235                 240

Ile Ile Pro Gly Pro Pro Leu Tyr Thr Gly
                245                 250

<210> SEQ ID NO 15
<211> LENGTH: 1172
<212> TYPE: DNA
<213> ORGANISM: Trichoderma reesei

<400> SEQUENCE: 15

```
ggatctaagc cccatcgata tgaagtcctg cgccattctt gcagcccttg gctgtcttgc      60
cgggagcgtt ctcggccatg gacaagtcca aaacttcacg atcaatggac aatacaatca    120
gggtttcatt ctcgattact actatcagaa gcagaatact ggtcacttcc caacgttgc     180
tggctggtac gccgaggacc tagacctggg cttcatctcc cctgaccaat acaccacgcc    240
cgacattgtc tgtcacaaga acgcggcccc aggtgccatt tctgccactg cagcggccgg    300
cagcaacatc gtcttccaat ggggccctgg cgtctggcct caccccctacg gtcccatcgt   360
tacctacgtg gctgagtgca gcggatcgtg cacgaccgtg aacaagaaca acctgcgctg    420
ggtcaagatt caggaggccg gcatcaacta aacacccaa gtctgggcgc agcaggatct     480
gatcaaccag ggcaacaagt ggactgtgaa gatcccgtcg agcctcaggc ccggaaacta    540
tgtcttccgc catgaacttc ttgctgccca tggtgcctct agtgcgaacg gcatgcagaa    600
ctatcctcag tgcgtgaaca tcgccgtcac aggctcgggc acgaaagcgc tccctgccgg    660
aactcctgca actcagctct acaagccacc tgaccctggc atcttgttca acccttacac    720
aacaatcacg agctacacca tccctggccc agccctgtgg caaggctaga tccagggtta    780
cggtgttggc gttcgtgaag tcggagctgt tgacaaggat atctgatgat gaacggagag    840
gactgatggg cgtgactgag tgtatatatt tttgatgacc aaattgtata cgaaatccga    900
acgcatggtg atcattgttt atccctgtag tatattgtct ccaggctgct aagagcccac    960
cgggtgtatt acggcaacaa agtcaggaat ttgggtggca atgaacgcag gtctccatga   1020
atgtatatgt gaagaggcat cggctggcat gggcattacc agatataggc cctgtgaaac   1080
atatagtact tgaacgtgct actggaacgg atcataagca agtcatcaac atgtgaaaaa   1140
acactacatg taaaaaaaaa aaaaaaaaaa aa                                 1172
```

<210> SEQ ID NO 16
<211> LENGTH: 249
<212> TYPE: PRT
<213> ORGANISM: Trichoderma reesei

<400> SEQUENCE: 16

Met Lys Ser Cys Ala Ile Leu Ala Ala Leu Gly Cys Leu Ala Gly Ser
1               5                   10                  15

Val Leu Gly His Gly Gln Val Gln Asn Phe Thr Ile Asn Gly Gln Tyr
                20                  25                  30

Asn Gln Gly Phe Ile Leu Asp Tyr Tyr Gln Lys Gln Asn Thr Gly
            35                  40                  45

His Phe Pro Asn Val Ala Gly Trp Tyr Ala Glu Asp Leu Asp Leu Gly
        50                  55                  60

Phe Ile Ser Pro Asp Gln Tyr Thr Thr Pro Asp Ile Val Cys His Lys
65                  70                  75                  80

```
Asn Ala Ala Pro Gly Ala Ile Ser Ala Thr Ala Ala Gly Ser Asn
                85                  90                  95

Ile Val Phe Gln Trp Gly Pro Gly Val Trp Pro His Pro Tyr Gly Pro
            100                 105                 110

Ile Val Thr Tyr Val Val Glu Cys Ser Gly Ser Cys Thr Thr Val Asn
            115                 120                 125

Lys Asn Asn Leu Arg Trp Val Lys Ile Gln Glu Ala Gly Ile Asn Tyr
            130                 135                 140

Asn Thr Gln Val Trp Ala Gln Gln Asp Leu Ile Asn Gln Gly Asn Lys
145                 150                 155                 160

Trp Thr Val Lys Ile Pro Ser Ser Leu Arg Pro Gly Asn Tyr Val Phe
                165                 170                 175

Arg His Glu Leu Leu Ala Ala His Gly Ala Ser Ser Ala Asn Gly Met
            180                 185                 190

Gln Asn Tyr Pro Gln Cys Val Asn Ile Ala Val Thr Gly Ser Gly Thr
            195                 200                 205

Lys Ala Leu Pro Ala Gly Thr Pro Ala Thr Gln Leu Tyr Lys Pro Thr
210                 215                 220

Asp Pro Gly Ile Leu Phe Asn Pro Tyr Thr Thr Ile Thr Ser Tyr Thr
225                 230                 235                 240

Ile Pro Gly Pro Ala Leu Trp Gln Gly
                245
```

<210> SEQ ID NO 17
<211> LENGTH: 2576
<212> TYPE: DNA
<213> ORGANISM: Humicola insolens

<400> SEQUENCE: 17

```
agctacagct tccttgggcc cgtctgaacc aaccttctgg gaccaagtgg tgagatctgg      60
cggcacaacc atgaagttcc tcggccgtat tggggcgacc gcccttgcgg cgtcgctgta    120
tctcacatca ggcgccgcgc aagccactgg tgatgcgtac accgactcgg aaacaggcat    180
taagttccag acctggtccc cggatccgca gttcactttt ggccttgccc tgccgccgga    240
tgccctggag aaggatgcca ctgagtacat tggtcttctc cgctgcacca gggccgaccc    300
atccgaccct ggctactgcg tctctctca tggccaggtc ggcagatga cgcagtcgct    360
gcttctcgtg gcctgggcct acgagaacca ggtctacacg tcgttccgct acgccaccgg    420
ctacaccctc ccgggtctgt acaccggcaa cgctaagctg acccagctct ccgtcaacat    480
caccgacacc agcttcgagc tcatctaccg ctgcgagaac tgcttctcgt gggagcacga    540
aggcagcacc ggatctagct cgacctccca gggctatctc gtcctcggtc gtgcttccgc    600
ccgccgcggc gtcgtcggcc cgacttgccc ggacacggcc acctttggtt ccacgacaa    660
tggcttcggt cagtggggtg ttggtctcga gaatgccgtt tcggagcagt attctgagtg    720
ggcttcgctg ccgggtctga ctgttgagac cacctgcgaa ggatccggcc tggtgaggc    780
gcagtgcgtg cctgcccctg aggagactta tgactatatt gttgttggtg ctggcgccgg    840
cggtattcct gtcgccgaca agctgagcga ggccggccac aaggttctgc tcatcgagaa    900
gggtccccg tcgacgggcc gctggcaggg taccatgaag cccgagtggc ttgaaggcac    960
tgacctcact cggttcgatg tgcccggcct ttgcaaccag atctgggttg actcggctgg   1020
cattgcctgc actgatactg atcagatggc tggctgcgtc ttgggcggtg cacggccgt   1080
taatgctggc ctgtggtgga agcccattga cctcgactgg gatgagaact ccctgaggg   1140
```

-continued

```
ctggcactcg caggatctcg ccgcggcgac cgagcgcgtc tttgagcgca tccccggcac    1200
ctggcacccg tccatggatg gcaagctgta ccgtgacgaa ggctacaagg ttctctccag    1260
cggtctggct gagtctggct ggaaggaggt tgtggccaac gaggttccca acgagaagaa    1320
ccgcactttc gcccacaccc acttcatgtt cgctggcgga gagcgtaacg ggcctcttgc    1380
cacttacctg gtctctgccg atgcccgcga gaacttctcg ctctggacca cactgctgt    1440 tcgccgcgct gtccgcactg gtggcaaggt cacaggtgtc gagctcgagt gcttgactga    1500
tggcggctac agcggcattg ttaagctcaa tgagggcggt ggcgtcatct tctcggccgg    1560
tgcctttggt tcggccaagc tgctcttccg cagcggtatc ggccctgagg atcagctccg    1620
cgttgttgcc tcctctaagg acggagagga cttcatcgac gagaaggact ggattaagct    1680
ccccgtcggc tacaacctga ttgaccacct taacactgac ctcatcctca ctcaccccga    1740
tgtcgtcttc tacgacttct atgaggcctg gaccaccccg atcgaggccg acaagcagct    1800
gtaccttgag cagcgctctg gcatccttgc ccaggctgct cctaacattg ccccatgat    1860 gtgggagcag gtcacccct cggacggcat acccgccaa ttccagtgga cggctcgcgt    1920
cgagggcgac agccgcttca ccaactcttc tcatgccatg actctcagcc agtacctcgg    1980
ccgtggtgtc gtgtcgcgcg tcgcgccac catcacccag ggtctcgtca ccaccgtggc    2040
tgagcacccg tacctccaca cgccggcga caaggaggcc gtcattcagg gcatcaagaa    2100
cctcattgag tctcttaacg tgattcccaa catcacttgg gtcctgccgc tcctggtag    2160 cactgtcgag gaatacgtcg attcgctcct cgtctccgcc tcggctcgtc gctcgaacca    2220
ctggatgggc acggccaagc tgggtactga tgatggccgc tacggcggta cttcggtcgt    2280
cgacctcgac accaaggtct acggcaccga taacctgttc gtggtggatg cttccatctt    2340
ccctggcatg tcgaccggca acccgtccgc tatgatcgtg attgccgctg agcaggctgc    2400
ggagcgcatt cttaagctga ggaagtaaga aggggagaga ggatggaggg atgacattga    2460
ggaaaatagg gttatgagtt gatgagttat gggcgaatgt gtcagccagt gtacttgact    2520
tattacctga gttaaacaac acgacgtgct tgatgtgtta aaaaaaaaa aacttt       2576
```

<210> SEQ ID NO 18
<211> LENGTH: 785
<212> TYPE: PRT
<213> ORGANISM: Humicola insolens

<400> SEQUENCE: 18

```
Met Lys Phe Leu Gly Arg Ile Gly Ala Thr Ala Leu Ala Ala Ser Leu
1               5                   10                  15

Tyr Leu Thr Ser Gly Ala Ala Gln Ala Thr Gly Asp Ala Tyr Thr Asp
            20                  25                  30

Ser Glu Thr Gly Ile Lys Phe Gln Thr Trp Ser Pro Asp Pro Gln Phe
        35                  40                  45

Thr Phe Gly Leu Ala Leu Pro Pro Asp Ala Leu Glu Lys Asp Ala Thr
    50                  55                  60

Glu Tyr Ile Gly Leu Leu Arg Cys Thr Arg Ala Asp Pro Ser Asp Pro
65                  70                  75                  80

Gly Tyr Cys Gly Leu Ser His Gly Gln Val Gly Met Thr Gln Ser
                85                  90                  95

Leu Leu Leu Val Ala Trp Ala Tyr Glu Asn Gln Val Tyr Thr Ser Phe
            100                 105                 110

Arg Tyr Ala Thr Gly Tyr Thr Leu Pro Gly Leu Tyr Thr Gly Asn Ala
```

```
              115                 120                 125
Lys Leu Thr Gln Leu Ser Val Asn Ile Thr Asp Thr Ser Phe Glu Leu
    130                 135                 140

Ile Tyr Arg Cys Glu Asn Cys Phe Ser Trp Glu His Glu Gly Ser Thr
145                 150                 155                 160

Gly Ser Ser Ser Thr Ser Gln Gly Tyr Leu Val Leu Gly Arg Ala Ser
                165                 170                 175

Ala Arg Arg Gly Val Val Gly Pro Thr Cys Pro Asp Thr Ala Thr Phe
                180                 185                 190

Gly Phe His Asp Asn Gly Phe Gly Gln Trp Gly Val Gly Leu Glu Asn
                195                 200                 205

Ala Val Ser Glu Gln Tyr Ser Glu Trp Ala Ser Leu Pro Gly Leu Thr
    210                 215                 220

Val Glu Thr Thr Cys Glu Gly Ser Gly Pro Gly Glu Ala Gln Cys Val
225                 230                 235                 240

Pro Ala Pro Glu Glu Thr Tyr Asp Tyr Ile Val Val Gly Ala Gly Ala
                245                 250                 255

Gly Gly Ile Pro Val Ala Asp Lys Leu Ser Glu Ala Gly His Lys Val
                260                 265                 270

Leu Leu Ile Glu Lys Gly Pro Pro Ser Thr Gly Arg Trp Gln Gly Thr
    275                 280                 285

Met Lys Pro Glu Trp Leu Glu Gly Thr Asp Leu Thr Arg Phe Asp Val
    290                 295                 300

Pro Gly Leu Cys Asn Gln Ile Trp Val Asp Ser Ala Gly Ile Ala Cys
305                 310                 315                 320

Thr Asp Thr Asp Gln Met Ala Gly Cys Val Leu Gly Gly Thr Thr Ala
                325                 330                 335

Val Asn Ala Gly Leu Trp Trp Lys Pro Ile Asp Leu Asp Trp Asp Glu
                340                 345                 350

Asn Phe Pro Glu Gly Trp His Ser Gln Asp Leu Ala Ala Ala Thr Glu
                355                 360                 365

Arg Val Phe Glu Arg Ile Pro Gly Thr Trp His Pro Ser Met Asp Gly
    370                 375                 380

Lys Leu Tyr Arg Asp Glu Gly Tyr Lys Val Leu Ser Ser Gly Leu Ala
385                 390                 395                 400

Glu Ser Gly Trp Lys Glu Val Ala Asn Glu Val Pro Asn Glu Lys
                405                 410                 415

Asn Arg Thr Phe Ala His Thr His Phe Met Phe Ala Gly Gly Glu Arg
                420                 425                 430

Asn Gly Pro Leu Ala Thr Tyr Leu Val Ser Ala Asp Ala Arg Glu Asn
                435                 440                 445

Phe Ser Leu Trp Thr Asn Thr Ala Val Arg Arg Ala Val Arg Thr Gly
    450                 455                 460

Gly Lys Val Thr Gly Val Glu Leu Glu Cys Leu Thr Asp Gly Gly Tyr
465                 470                 475                 480

Ser Gly Ile Val Lys Leu Asn Glu Gly Gly Val Ile Phe Ser Ala
                485                 490                 495

Gly Ala Phe Gly Ser Ala Lys Leu Leu Phe Arg Ser Gly Ile Gly Pro
                500                 505                 510

Glu Asp Gln Leu Arg Val Val Ala Ser Ser Lys Asp Gly Glu Asp Phe
                515                 520                 525

Ile Asp Glu Lys Asp Trp Ile Lys Leu Pro Val Gly Tyr Asn Leu Ile
                530                 535                 540
```

```
Asp His Leu Asn Thr Asp Leu Ile Leu Thr His Pro Asp Val Val Phe
545                 550                 555                 560

Tyr Asp Phe Tyr Glu Ala Trp Thr Thr Pro Ile Glu Ala Asp Lys Gln
            565                 570                 575

Leu Tyr Leu Glu Gln Arg Ser Gly Ile Leu Ala Gln Ala Ala Pro Asn
        580                 585                 590

Ile Gly Pro Met Met Trp Glu Gln Val Thr Pro Ser Asp Gly Ile Thr
    595                 600                 605

Arg Gln Phe Gln Trp Thr Ala Arg Val Glu Gly Asp Ser Arg Phe Thr
610                 615                 620

Asn Ser Ser His Ala Met Thr Leu Ser Gln Tyr Leu Gly Arg Gly Val
625                 630                 635                 640

Val Ser Arg Gly Arg Ala Thr Ile Thr Gln Gly Leu Val Thr Thr Val
            645                 650                 655

Ala Glu His Pro Tyr Leu His Asn Ala Gly Asp Lys Glu Ala Val Ile
        660                 665                 670

Gln Gly Ile Lys Asn Leu Ile Glu Ser Leu Asn Val Ile Pro Asn Ile
    675                 680                 685

Thr Trp Val Leu Pro Pro Gly Ser Thr Val Glu Glu Tyr Val Asp
690                 695                 700

Ser Leu Leu Val Ser Ala Ser Ala Arg Arg Ser Asn His Trp Met Gly
705                 710                 715                 720

Thr Ala Lys Leu Gly Thr Asp Asp Gly Arg Tyr Gly Thr Ser Val
            725                 730                 735

Val Asp Leu Asp Thr Lys Val Tyr Gly Thr Asp Asn Leu Phe Val Val
        740                 745                 750

Asp Ala Ser Ile Phe Pro Gly Met Ser Thr Gly Asn Pro Ser Ala Met
    755                 760                 765

Ile Val Ile Ala Ala Glu Gln Ala Ala Glu Arg Ile Leu Lys Leu Arg
770                 775                 780

Lys
785

<210> SEQ ID NO 19
<211> LENGTH: 923
<212> TYPE: DNA
<213> ORGANISM: Humicola insolens

<400> SEQUENCE: 19
atgcgttcct ccccctcct ccgctccgcc gttgtggccg ccctgccggt gttggccctt     60
gccgctgatg caggtccac cgctactgg gactgctgca agccttcgtg cggctgggcc    120
aagaaggctc ccgtgaacca gcctgtcttt tcctgcaacg ccaacttcca gcgtatcacg    180
gacttcgacg ccaagtccgg ctgcgagccg ggcggtgtcg cctactcgtg cgccgaccag    240
accccatggg ctgtgaacga cgacttcgcg ctcggttttg ctgccacctc tattgccggc    300
agcaatgagg cgggctggtg ctgcgcctgc tacgagctca ccttcacatc cggtcctgtt    360
gctggcaaga gatggtcgt ccagtccacc agcactggcg gtgatcttgg cagcaaccac    420
ttcgatctca acatccccgg cggcggcgtc ggcatcttcg acggatgcac tccccagttc    480
ggcggtctgc ccggccagcg ctacggcggc atctcgtccc gcaacgagtg cgatcggttc    540
cccgacgccc tcaagcccgg ctgctactgg cgcttcgact ggttcaagaa cgccgacaat    600
ccgagcttca gcttccgtca ggtccagtgc ccagccgagc tcgtcgctcg caccggatgc    660
```

```
cgccgcaacg acgacggcaa cttccctgcc gtccagatcc cctccagcag caccagctct    720
ccggtcaacc agcctaccag caccagcacc acgtccacct ccaccacctc gagcccgcca    780
gtccagccta cgactcccag cggctgcact gctgagaggt gggctcagtg cggcggcaat    840
ggctggagcg gctgcaccac ctgcgtcgct ggcagcactt gcacgaagat taatgactgg    900
taccatcagt gcctgtagaa ttc                                            923
```

<210> SEQ ID NO 20
<211> LENGTH: 305
<212> TYPE: PRT
<213> ORGANISM: Humicola insolens

<400> SEQUENCE: 20

```
Met Arg Ser Ser Pro Leu Leu Arg Ser Ala Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Ser Ser Thr Ser Ser
225                 230                 235                 240

Pro Val Asn Gln Pro Thr Ser Thr Ser Thr Thr Ser Thr Ser Thr Thr
                245                 250                 255

Ser Ser Pro Pro Val Gln Pro Thr Thr Pro Ser Gly Cys Thr Ala Glu
            260                 265                 270

Arg Trp Ala Gln Cys Gly Gly Asn Gly Trp Ser Gly Cys Thr Thr Cys
        275                 280                 285

Val Ala Gly Ser Thr Cys Thr Lys Ile Asn Asp Trp Tyr His Gln Cys
    290                 295                 300

Leu
305
```

<210> SEQ ID NO 21
<211> LENGTH: 1188
<212> TYPE: DNA
<213> ORGANISM: Myceliophthora thermophila

<400> SEQUENCE: 21

```
cgacttgaaa cgccccaaat gaagtcctcc atcctcgcca gcgtcttcgc cacgggcgcc    60
gtggctcaaa gtggtccgtg gcagcaatgt ggtggcatcg gatggcaagg atcgaccgac   120
tgtgtgtcgg ctaccactg cgtctaccag aacgattggt acagccagtg cgtgcctggc   180
gcggcgtcga caacgctgca gacatcgacc acgtccaggc ccaccgccac cagcaccgcc   240
cctccgtcgt ccaccacctc gcctagcaag ggcaagctga gtggctcgg cagcaacgag   300
tcgggcgccg agttcgggga gggcaattac cccggcctct ggggcaagca cttcatcttc   360
ccgtcgactt cggcgattca gacgctcatc aatgatggat acaacatctt ccggatcgac   420
ttctcgatgg agcgtctggt gcccaaccag ttgacgtcgt ccttcgacca gggttacctc   480
cgcaaccctga ccgaggtggt caacttcgtg acgaacgcgg gcaagtacgc cgtcctggac   540
ccgcacaact acggccggta ctacggcaac atcatcacgg acacgaacgc gttccggacc   600
ttctggacca acctggccaa gcagttcgcc tccaactcgc tcgtcatctt cgacaccaac   660
aacgagtaca acacgatgga ccagaccctg gtgctcaacc tcaaccaggc cgccatcgac   720
ggcatccggg ccgccggcgc gacctcgcag tacatcttcg tcgagggcaa cgcgtggagc   780
ggggcctgga gctggaacac gaccaacacc aacatggccg ccctgacgga cccgcagaac   840
aagatcgtgt acgagatgca ccagtacctc gactcggaca gctcgggcac ccacgccgag   900
tgcgtcagca gcaccatcgg cgcccagcgc gtcgtcggag ccacccagtg gctccgcgcc   960
aacggcaagc tcggcgtcct cggcgagttc gccggcggcg ccaacgccgt ctgccagcag  1020
gccgtcaccg gcctcctcga ccacctccag gacaacagcg acgtctggct gggtgccctc  1080
tggtgggccg ccggtccctg gtggggcgac tacatgtact cgttcgagcc tccttcgggc  1140
accggctatg tcaactacaa ctcgatcttg aagaagtact gccgtaa           1188
```

<210> SEQ ID NO 22
<211> LENGTH: 389
<212> TYPE: PRT
<213> ORGANISM: Myceliophthora thermophila

<400> SEQUENCE: 22

```
Met Lys Ser Ser Ile Leu Ala Ser Val Phe Ala Thr Gly Ala Ala
1               5                   10                  15

Gln Ser Gly Pro Trp Gln Gln Cys Gly Gly Ile Gly Trp Gln Gly Ser
                20                  25                  30

Thr Asp Cys Val Ser Gly Tyr His Cys Val Tyr Gln Asn Asp Trp Tyr
            35                  40                  45

Ser Gln Cys Val Pro Gly Ala Ala Ser Thr Thr Leu Gln Thr Ser Thr
        50                  55                  60

Thr Ser Arg Pro Thr Ala Thr Ser Thr Ala Pro Ser Ser Thr Thr
65                  70                  75                  80

Ser Pro Ser Lys Gly Lys Leu Lys Trp Leu Gly Ser Asn Glu Ser Gly
                85                  90                  95

Ala Glu Phe Gly Glu Gly Asn Tyr Pro Gly Leu Trp Gly Lys His Phe
            100                 105                 110

Ile Phe Pro Ser Thr Ser Ala Ile Gln Thr Leu Ile Asn Asp Gly Tyr
        115                 120                 125
```

```
Asn Ile Phe Arg Ile Asp Phe Ser Met Glu Arg Leu Val Pro Asn Gln
130                 135                 140
Leu Thr Ser Ser Phe Asp Gln Gly Tyr Leu Arg Asn Leu Thr Glu Val
145                 150                 155                 160
Val Asn Phe Val Thr Asn Ala Gly Lys Tyr Ala Val Leu Asp Pro His
                165                 170                 175
Asn Tyr Gly Arg Tyr Tyr Gly Asn Ile Ile Thr Asp Thr Asn Ala Phe
                180                 185                 190
Arg Thr Phe Trp Thr Asn Leu Ala Lys Gln Phe Ala Ser Asn Ser Leu
            195                 200                 205
Val Ile Phe Asp Thr Asn Asn Glu Tyr Asn Thr Met Asp Gln Thr Leu
210                 215                 220
Val Leu Asn Leu Asn Gln Ala Ala Ile Asp Gly Ile Arg Ala Ala Gly
225                 230                 235                 240
Ala Thr Ser Gln Tyr Ile Phe Val Glu Gly Asn Ala Trp Ser Gly Ala
                245                 250                 255
Trp Ser Trp Asn Thr Thr Asn Thr Asn Met Ala Ala Leu Thr Asp Pro
            260                 265                 270
Gln Asn Lys Ile Val Tyr Glu Met His Gln Tyr Leu Asp Ser Asp Ser
        275                 280                 285
Ser Gly Thr His Ala Glu Cys Val Ser Ser Thr Ile Gly Ala Gln Arg
    290                 295                 300
Val Val Gly Ala Thr Gln Trp Leu Arg Ala Asn Gly Lys Leu Gly Val
305                 310                 315                 320
Leu Gly Glu Phe Ala Gly Gly Ala Asn Ala Val Cys Gln Gln Ala Val
                325                 330                 335
Thr Gly Leu Leu Asp His Leu Gln Asp Asn Ser Asp Val Trp Leu Gly
            340                 345                 350
Ala Leu Trp Trp Ala Ala Gly Pro Trp Trp Gly Asp Tyr Met Tyr Ser
        355                 360                 365
Phe Glu Pro Pro Ser Gly Thr Gly Tyr Val Asn Tyr Asn Ser Ile Leu
    370                 375                 380
Lys Lys Tyr Leu Pro
385

<210> SEQ ID NO 23
<211> LENGTH: 1232
<212> TYPE: DNA
<213> ORGANISM: Basidiomycete CBS 495.95

<400> SEQUENCE: 23
ggatccactt agtaacggcc gccagtgtgc tggaaagcat gaagtctctc ttcctgtcac    60
ttgtagcgac cgtcgcgctc agctcgccag tattctctgt cgcagtctgg gggcaatgcg   120
gcggcattgg cttcagcgga agcaccgtct gtgatgcagg cgccggctgt gtgaagctca   180
acgactatta ctctcaatgc caacccggcg ctcccactgc tacatccgcg cgccaagta    240
gcaacgcacc gtccggcact cgacggcct cggccccctc ctccagcctt tgctctggca    300
gccgcacgcc gttccagttc ttcggtgtca acgaatccgg cgcggagttc ggcaacctga   360
acatccccgg tgttctgggc accgactaca cctggccgtc gccatccagc attgacttct   420
tcatgggcaa gggaatgaat accttccgta ttccgttcct catggagcgt cttgtccccc   480
ctgccactgg catcacagga cctctcgacc agacgtactt gggcggcctg cagacgattg   540
tcaactacat caccggcaaa ggcggctttg ctctcattga cccgcacaac tttatgatct   600
```

```
acaatggcca gacgatctcc agtaccagcg acttccagaa gttctggcag aacctcgcag    660
gagtgtttaa atcgaacagt cacgtcatct tcgatgttat gaacgagcct cacgatattc    720
ccgcccagac cgtgttccaa ctgaaccaag ccgctgtcaa tggcatccgt gcgagcggtg    780
cgacgtcgca gctcattctg gtcgagggca caagctggac tggagcctgg acctggacga    840
cctctggcaa cagcgatgca ttcggtgcca ttaaggatcc caacaacaac gtcgcgatcc    900
agatgcatca gtacctggat agcgatggct ctggcacttc gcagacctgc gtgtctccca    960
ccatcggtgc cgagcggttg caggctgcga ctcaatggtt gaagcagaac aacctcaagg   1020
gcttcctggg cgagatcggc gccggctcta actccgcttg catcagcgct gtgcagggtg   1080
cgttgtgttc gatgcagcaa tctggtgtgt ggctcggcgc tctctggtgg gctgcgggcc   1140
cgtggtgggg cgactactac cagtccatcg agccgccctc tggcccggcg gtgtccgcga   1200
tcctcccgca ggccctgctg ccgttcgcgt aa                                  1232
```

<210> SEQ ID NO 24
<211> LENGTH: 397
<212> TYPE: PRT
<213> ORGANISM: Basidiomycete CBS 495.95

<400> SEQUENCE: 24

```
Met Lys Ser Leu Phe Leu Ser Leu Val Ala Thr Val Ala Leu Ser Ser
1               5                   10                  15

Pro Val Phe Ser Val Ala Val Trp Gly Gln Cys Gly Gly Ile Gly Phe
            20                  25                  30

Ser Gly Ser Thr Val Cys Asp Ala Gly Ala Gly Cys Val Lys Leu Asn
        35                  40                  45

Asp Tyr Tyr Ser Gln Cys Gln Pro Gly Ala Pro Thr Ala Thr Ser Ala
    50                  55                  60

Ala Pro Ser Ser Asn Ala Pro Ser Gly Thr Ser Thr Ala Ser Ala Pro
65                  70                  75                  80

Ser Ser Ser Leu Cys Ser Gly Ser Arg Thr Pro Phe Gln Phe Phe Gly
                85                  90                  95

Val Asn Glu Ser Gly Ala Glu Phe Gly Asn Leu Asn Ile Pro Gly Val
            100                 105                 110

Leu Gly Thr Asp Tyr Thr Trp Pro Ser Pro Ser Ser Ile Asp Phe Phe
        115                 120                 125

Met Gly Lys Gly Met Asn Thr Phe Arg Ile Pro Phe Leu Met Glu Arg
    130                 135                 140

Leu Val Pro Pro Ala Thr Gly Ile Thr Gly Pro Leu Asp Gln Thr Tyr
145                 150                 155                 160

Leu Gly Gly Leu Gln Thr Ile Val Asn Tyr Ile Thr Gly Lys Gly Gly
                165                 170                 175

Phe Ala Leu Ile Asp Pro His Asn Phe Met Ile Tyr Asn Gly Gln Thr
            180                 185                 190

Ile Ser Ser Thr Ser Asp Phe Gln Lys Phe Trp Gln Asn Leu Ala Gly
        195                 200                 205

Val Phe Lys Ser Asn Ser His Val Ile Phe Asp Val Met Asn Glu Pro
    210                 215                 220

His Asp Ile Pro Ala Gln Thr Val Phe Gln Leu Asn Gln Ala Ala Val
225                 230                 235                 240

Asn Gly Ile Arg Ala Ser Gly Ala Thr Ser Gln Leu Ile Leu Val Glu
                245                 250                 255

Gly Thr Ser Trp Thr Gly Ala Trp Thr Trp Thr Thr Ser Gly Asn Ser
```

```
                    260                 265                 270
Asp Ala Phe Gly Ala Ile Lys Asp Pro Asn Asn Val Ala Ile Gln
                275                 280                 285
Met His Gln Tyr Leu Asp Ser Asp Gly Ser Gly Thr Ser Gln Thr Cys
            290                 295                 300
Val Ser Pro Thr Ile Gly Ala Glu Arg Leu Gln Ala Ala Thr Gln Trp
305                 310                 315                 320
Leu Lys Gln Asn Asn Leu Lys Gly Phe Leu Gly Glu Ile Gly Ala Gly
                325                 330                 335
Ser Asn Ser Ala Cys Ile Ser Ala Val Gln Gly Ala Leu Cys Ser Met
                340                 345                 350
Gln Gln Ser Gly Val Trp Leu Gly Ala Leu Trp Ala Ala Gly Pro
                355                 360                 365
Trp Trp Gly Asp Tyr Tyr Gln Ser Ile Glu Pro Pro Ser Gly Pro Ala
            370                 375                 380
Val Ser Ala Ile Leu Pro Gln Ala Leu Leu Pro Phe Ala
385                 390                 395
```

<210> SEQ ID NO 25
<211> LENGTH: 1303
<212> TYPE: DNA
<213> ORGANISM: Basidiomycete CBS 495.95

<400> SEQUENCE: 25

```
ggaaagcgtc agtatggtga aatttgcgct tgtggcaact gtcggcgcaa tcttgagcgc      60
ttctgcggcc aatgcggctt ctatctacca gcaatgtgga ggcattggat ggtctgggtc     120
cactgtttgc gacgccggtc tcgcttgcgt tatcctcaat gcgtactact ttcagtgctt     180
gacgcccgcc gcgggccaga caacgacggg ctcgggcgca ccggcgtcaa catcaacctc     240
tcactcaacg gtcactacgg ggagctcaca ctcaacaacc gggacgacgg cgacgaaaac     300
aactaccact ccgtcgacca ccacgaccct acccgccatc tctgtgtctg gtcgcgtctg     360
ctctggctcc aggacgaagt tcaagttctt cggtgtgaat gaaagcggcg ccgaattcgg     420
gaacactgct tggccagggc agctcgggaa agactataca tggccttcgc ctagcagcgt     480
ggactacttc atgggggctg gattcaatac attccgtatc accttcttga tggagcgtat     540
gagccctccg gctaccggac tcactggccc attcaaccag acgtacctgt cgggcctcac     600
caccattgtc gactacatca cgaacaaagg aggatacgct cttattgacc cccacaactt     660
catgcgttac aacaacggca taatcagcag cacatctgac ttcgcgactt ggtggagcaa     720
tttggccact gtattcaaat ccacgaagaa cgccatcttc gacatccaga acgagccgta     780
cggaatcgat gcgcagaccg tatcgaact gaatcaagct gccatcaatt cgatccgcgc     840
cgctggcgct acgtcacagt tgattctggt tgaaggaacg tcatacactg agcttggac     900
gtgggtctcg tccggaaacg gagctgcttt cgcggccgtt acggatcctt acaacaacac     960
ggcaattgaa atgcaccaat acctcgacag cgacggttct gggacaaacg aagactgtgt    1020
ctcctccacc attgggtcgc aacgtctcca agctgccact gcgtggctgc aacaaacagg    1080
actcaaggga ttcctcggag agacgggtgc tgggtcgaat cccagtgca tgacgcgcgt    1140
gttcgatgaa ctttgctata tgcaacagca aggcggctcc tggatcggtg cactctggtg    1200
ggctgcgggt ccctggtggg gcacgtacat ttactcgatt gaacctccga gcggtgccgc    1260
tatcccagaa gtccttcctc agggtctcgc tccattcctc tag                      1303
```

```
<210> SEQ ID NO 26
<211> LENGTH: 429
<212> TYPE: PRT
<213> ORGANISM: Basidiomycete CBS 495.95

<400> SEQUENCE: 26

Met Val Lys Phe Ala Leu Val Ala Thr Val Gly Ala Ile Leu Ser Ala
  1               5                  10                  15

Ser Ala Asn Ala Ala Ser Ile Tyr Gln Gln Cys Gly Gly Ile Gly
             20                  25                  30

Trp Ser Gly Ser Thr Val Cys Asp Ala Gly Leu Ala Cys Val Ile Leu
         35                  40                  45

Asn Ala Tyr Tyr Phe Gln Cys Leu Thr Pro Ala Ala Gly Gln Thr Thr
 50                  55                  60

Thr Gly Ser Gly Ala Pro Ala Ser Thr Ser Ser His Ser Thr Val
 65                  70                  75                  80

Thr Thr Gly Ser Ser His Ser Thr Thr Gly Thr Thr Ala Thr Lys Thr
                 85                  90                  95

Thr Thr Thr Pro Ser Thr Thr Thr Leu Pro Ala Ile Ser Val Ser
                100                 105                 110

Gly Arg Val Cys Ser Gly Ser Arg Thr Lys Phe Lys Phe Gly Val
            115                 120                 125

Asn Glu Ser Gly Ala Glu Phe Gly Asn Thr Ala Trp Pro Gly Gln Leu
130                 135                 140

Gly Lys Asp Tyr Thr Trp Pro Ser Pro Ser Ser Val Asp Tyr Phe Met
145                 150                 155                 160

Gly Ala Gly Phe Asn Thr Phe Arg Ile Thr Phe Leu Met Glu Arg Met
                165                 170                 175

Ser Pro Pro Ala Thr Gly Leu Thr Gly Pro Phe Asn Gln Thr Tyr Leu
            180                 185                 190

Ser Gly Leu Thr Thr Ile Val Asp Tyr Ile Thr Asn Lys Gly Gly Tyr
            195                 200                 205

Ala Leu Ile Asp Pro His Asn Phe Met Arg Tyr Asn Asn Gly Ile Ile
210                 215                 220

Ser Ser Thr Ser Asp Phe Ala Thr Trp Trp Ser Asn Leu Ala Thr Val
225                 230                 235                 240

Phe Lys Ser Thr Lys Asn Ala Ile Phe Asp Ile Gln Asn Glu Pro Tyr
                245                 250                 255

Gly Ile Asp Ala Gln Thr Val Tyr Glu Leu Asn Gln Ala Ala Ile Asn
            260                 265                 270

Ser Ile Arg Ala Ala Gly Ala Thr Ser Gln Leu Ile Leu Val Glu Gly
            275                 280                 285

Thr Ser Tyr Thr Gly Ala Trp Thr Trp Val Ser Ser Gly Asn Gly Ala
290                 295                 300

Ala Phe Ala Ala Val Thr Asp Pro Tyr Asn Asn Thr Ala Ile Glu Met
305                 310                 315                 320

His Gln Tyr Leu Asp Ser Asp Gly Ser Gly Thr Asn Glu Asp Cys Val
                325                 330                 335

Ser Ser Thr Ile Gly Ser Gln Arg Leu Gln Ala Ala Thr Ala Trp Leu
            340                 345                 350

Gln Gln Thr Gly Leu Lys Gly Phe Leu Gly Glu Thr Gly Ala Gly Ser
            355                 360                 365

Asn Ser Gln Cys Ile Asp Ala Val Phe Asp Glu Leu Cys Tyr Met Gln
        370                 375                 380
```

Gln Gln Gly Gly Ser Trp Ile Gly Ala Leu Trp Ala Ala Gly Pro
385                 390                 395                 400

Trp Trp Gly Thr Tyr Ile Tyr Ser Ile Glu Pro Pro Ser Gly Ala Ala
            405                 410                 415

Ile Pro Glu Val Leu Pro Gln Gly Leu Ala Pro Phe Leu
            420                 425

<210> SEQ ID NO 27
<211> LENGTH: 1580
<212> TYPE: DNA
<213> ORGANISM: Thielavia terrestris

<400> SEQUENCE: 27

| | | | | | |
|---|---|---|---|---|---|
| agcccccgt | tcaggcacac | ttggcatcag | atcagcttag | cagcgcctgc | acagcatgaa | 60 |
| gctctcgcag | tcgccgcgc | tggcggcact | caccgcgacg | gcgctcgccg | cccctcgcc | 120 |
| cacgacgccg | caggcgccga | ggcaggcttc | agccggctgc | tcgtctgcgg | tcacgctcga | 180 |
| cgccagcacc | aacgtttgga | agaagtacac | gctgcacccc | aacagctact | accgcaagga | 240 |
| ggttgaggcc | gcggtggcgc | agatctcgga | cccggacctc | gccgccaagg | ccaagaaggt | 300 |
| ggccgacgtc | ggcaccttcc | tgtggctcga | ctcgatcgag | aacatcggca | agctggagcc | 360 |
| ggcgatccag | gacgtgccct | gcgagaacat | cctgggcctg | gtcatctacg | acctgccggg | 420 |
| ccgcgactgc | gcggccaagg | cgtccaacgg | cgagctcaag | gtcggcgaga | tcgaccgcta | 480 |
| caagaccgag | tacatcgaca | gtgagtgctg | cccccggggt | tcgagaagag | cgtgggggaa | 540 |
| agggaaaggg | ttgactgact | gacacggcgc | actgcagaga | tcgtgtcgat | cctcaaggca | 600 |
| caccccaaca | cggcgttcgc | gctggtcatc | gagccggact | cgctgcccaa | cctggtgacc | 660 |
| aacagcaact | tggacacgtg | ctcgagcagc | gcgtcgggct | accgcgaagg | cgtggcttac | 720 |
| gccctcaaga | acctcaacct | gcccaacgtg | atcatgtacc | tcgacgccgg | ccacggcggc | 780 |
| tggctcggct | gggacgccaa | cctgcagccc | ggcgcgcagg | agctagccaa | ggcgtacaag | 840 |
| aacgccggct | cgcccaagca | gctccgcggc | ttctcgacca | acgtggccgg | ctggaactcc | 900 |
| tggtgagctt | ttttccattc | catttcttct | tcctcttctc | tcttcgctcc | cactctgcag | 960 |
| ccccccctcc | cccaagcacc | cactggcgtt | ccggcttgct | gactcggcct | cccttttcccc | 1020 |
| gggcaccagg | gatcaatcgc | ccggcgaatt | ctcccaggcg | tccgacgcca | agtacaacaa | 1080 |
| gtgccagaac | gagaagatct | acgtcagcac | cttcggctcc | gcgctccagt | cggccggcat | 1140 |
| gcccaaccac | gccatcgtcg | acacgggccg | caacggcgtc | accggcctgc | gcaaggagtg | 1200 |
| gggtgactgg | tgcaacgtca | acggtgcagg | ttcgttgtct | tctttttctc | tctcttttgtt | 1260 |
| tgcacgtcgt | ggtccttttc | aagcagccgt | gtttggttgg | gggagatgga | ctccggctga | 1320 |
| tgttctgctt | cctctctagg | cttcggcgtg | cgcccgacga | gcaacacggg | cctcgagctg | 1380 |
| gccgacgcgt | tcgtgtgggt | caagcccggc | ggcgagtcgg | acggcaccag | cgacagctcg | 1440 |
| tcgccgcgct | acgacagctt | ctgcggcaag | gacgacgcct | tcaagccctc | gcccgaggcc | 1500 |
| ggcacctgga | acgaggccta | cttcgagatg | ctgctcaaga | acgccgtgcc | gtcgttctaa | 1560 |
| gacggtccag | catcatccgg | | | | | 1580 |

<210> SEQ ID NO 28
<211> LENGTH: 396
<212> TYPE: PRT
<213> ORGANISM: Thielavia terrestris

<400> SEQUENCE: 28

```
Met Lys Leu Ser Gln Ser Ala Ala Leu Ala Leu Thr Ala Thr Ala
1               5                   10                  15

Leu Ala Ala Pro Ser Pro Thr Thr Pro Gln Ala Pro Arg Gln Ala Ser
            20                  25                  30

Ala Gly Cys Ser Ser Ala Val Thr Leu Asp Ala Ser Thr Asn Val Trp
            35                  40                  45

Lys Lys Tyr Thr Leu His Pro Asn Ser Tyr Tyr Arg Lys Glu Val Glu
50                  55                  60

Ala Ala Val Ala Gln Ile Ser Asp Pro Asp Leu Ala Ala Lys Ala Lys
65                  70                  75                  80

Lys Val Ala Asp Val Gly Thr Phe Leu Trp Leu Asp Ser Ile Glu Asn
                85                  90                  95

Ile Gly Lys Leu Glu Pro Ala Ile Gln Asp Val Pro Cys Glu Asn Ile
            100                 105                 110

Leu Gly Leu Val Ile Tyr Asp Leu Pro Gly Arg Asp Cys Ala Ala Lys
            115                 120                 125

Ala Ser Asn Gly Glu Leu Lys Val Gly Glu Ile Asp Arg Tyr Lys Thr
            130                 135                 140

Glu Tyr Ile Asp Lys Ile Val Ser Ile Leu Lys Ala His Pro Asn Thr
145                 150                 155                 160

Ala Phe Ala Leu Val Ile Glu Pro Asp Ser Leu Pro Asn Leu Val Thr
                165                 170                 175

Asn Ser Asn Leu Asp Thr Cys Ser Ser Ser Ala Ser Gly Tyr Arg Glu
            180                 185                 190

Gly Val Ala Tyr Ala Leu Lys Asn Leu Asn Leu Pro Asn Val Ile Met
            195                 200                 205

Tyr Leu Asp Ala Gly His Gly Gly Trp Leu Gly Trp Asp Ala Asn Leu
210                 215                 220

Gln Pro Gly Ala Gln Glu Leu Ala Lys Ala Tyr Lys Asn Ala Gly Ser
225                 230                 235                 240

Pro Lys Gln Leu Arg Gly Phe Ser Thr Asn Val Ala Gly Trp Asn Ser
                245                 250                 255

Trp Asp Gln Ser Pro Gly Glu Phe Ser Gln Ala Ser Asp Ala Lys Tyr
            260                 265                 270

Asn Lys Cys Gln Asn Glu Lys Ile Tyr Val Ser Thr Phe Gly Ser Ala
            275                 280                 285

Leu Gln Ser Ala Gly Met Pro Asn His Ala Ile Val Asp Thr Gly Arg
290                 295                 300

Asn Gly Val Thr Gly Leu Arg Lys Glu Trp Gly Asp Trp Cys Asn Val
305                 310                 315                 320

Asn Gly Ala Gly Phe Gly Val Arg Pro Thr Ser Asn Thr Gly Leu Glu
                325                 330                 335

Leu Ala Asp Ala Phe Val Trp Val Lys Pro Gly Gly Glu Ser Asp Gly
            340                 345                 350

Thr Ser Asp Ser Ser Ser Pro Arg Tyr Asp Ser Phe Cys Gly Lys Asp
            355                 360                 365

Asp Ala Phe Lys Pro Ser Pro Glu Ala Gly Thr Trp Asn Glu Ala Tyr
370                 375                 380

Phe Glu Met Leu Leu Lys Asn Ala Val Pro Ser Phe
385                 390                 395
```

<210> SEQ ID NO 29
<211> LENGTH: 1203
<212> TYPE: DNA

<213> ORGANISM: Thielavia terrestris

<400> SEQUENCE: 29

| | | |
|---|---|---:|
| atgaagtacc tcaacctcct cgcagctctc ctcgccgtcg ctcctctctc cctcgctgca | | 60 |
| cccagcatcg aggccagaca gtcgaacgtc aacccataca tcggcaagag cccgctcgtt | | 120 |
| attaggtcgt acgcccaaaa gcttgaggag accgtcagga ccttccagca acgtggcgac | | 180 |
| cagctcaacg ctgcgaggac acggacggtg cagaacgttg cgactttcgc ctggatctcg | | 240 |
| gataccaatg gtattggagc cattcgacct ctcatccaag atgctctcgc ccagcaggct | | 300 |
| cgcactggac agaaggtcat cgtccaaatc gtcgtctaca acctcccaga tcgcgactgc | | 360 |
| tctgccaacg cctcgactgg agagttcacc gtaggaaacg acggtctcaa ccgatacaag | | 420 |
| aactttgtca caccatcgc ccgcgagctc tcgactgctg acgctgacaa gctccacttt | | 480 |
| gccctcctcc tcgaacccga cgcacttgcc aacctcgtca ccaacgcgaa tgccccagg | | 540 |
| tgccgaatcg ccgctcccgc ttacaaggag ggtatcgcct acaccctcgc caccttgtcc | | 600 |
| aagcccaacg tcgacgtcta catcgacgcc gccaacggtg gctggctcgg ctggaacgac | | 660 |
| aacctccgcc ccttcgccga actcttcaag gaagtctacg acctcgcccg ccgcatcaac | | 720 |
| cccaacgcca aggtccgcgg cgtccccgtc aacgtctcca actacaacca gtaccgcgct | | 780 |
| gaagtccgcg agcccttcac cgagtggaag gacgcctggg acgagagccg ctacgtcaac | | 840 |
| gtcctcaccc cgcacctcaa cgccgtcggc ttctccgcgc acttcatcgt tgaccaggga | | 900 |
| cgcggtggca agggcggtat caggacggag tggggccagt ggtgcaacgt taggaacgct | | 960 |
| gggttcggta tcaggcctac tgcggatcag ggcgtgctcc agaacccgaa tgtggatgcg | | 1020 |
| attgtgtggg ttaagccggg tggagagtcg gatggcacga gtgatttgaa ctcgaacagg | | 1080 |
| tatgatccta cgtgcaggag tccggtggcg catgttcccg ctcctgaggc tggccagtgg | | 1140 |
| ttcaacgagt atgttgttaa cctcgttttg aacgctaacc cccctcttga gcctacctgg | | 1200 |
| taa | | 1203 |

<210> SEQ ID NO 30
<211> LENGTH: 400
<212> TYPE: PRT
<213> ORGANISM: Thielavia terrestris

<400> SEQUENCE: 30

```
Met Lys Tyr Leu Asn Leu Leu Ala Ala Leu Ala Val Ala Pro Leu
1               5                   10                  15

Ser Leu Ala Ala Pro Ser Ile Glu Ala Arg Gln Ser Asn Val Asn Pro
            20                  25                  30

Tyr Ile Gly Lys Ser Pro Leu Val Ile Arg Ser Tyr Ala Gln Lys Leu
        35                  40                  45

Glu Glu Thr Val Arg Thr Phe Gln Gln Arg Gly Asp Gln Leu Asn Ala
    50                  55                  60

Ala Arg Thr Arg Thr Val Gln Asn Val Ala Thr Phe Ala Trp Ile Ser
65                  70                  75                  80

Asp Thr Asn Gly Ile Gly Ala Ile Arg Pro Leu Ile Gln Asp Ala Leu
                85                  90                  95

Ala Gln Gln Ala Arg Thr Gly Gln Lys Val Ile Val Gln Ile Val Val
            100                 105                 110

Tyr Asn Leu Pro Asp Arg Asp Cys Ser Ala Asn Ala Ser Thr Gly Glu
        115                 120                 125

Phe Thr Val Gly Asn Asp Gly Leu Asn Arg Tyr Lys Asn Phe Val Asn
```

```
                130                 135                 140
Thr Ile Ala Arg Glu Leu Ser Thr Ala Asp Ala Asp Lys Leu His Phe
145                 150                 155                 160

Ala Leu Leu Leu Glu Pro Asp Ala Leu Ala Asn Leu Val Thr Asn Ala
                165                 170                 175

Asn Ala Pro Arg Cys Arg Ile Ala Ala Pro Ala Tyr Lys Glu Gly Ile
                180                 185                 190

Ala Tyr Thr Leu Ala Thr Leu Ser Lys Pro Asn Val Asp Val Tyr Ile
                195                 200                 205

Asp Ala Ala Asn Gly Gly Trp Leu Gly Trp Asn Asp Asn Leu Arg Pro
                210                 215                 220

Phe Ala Glu Leu Phe Lys Glu Val Tyr Asp Leu Ala Arg Arg Ile Asn
225                 230                 235                 240

Pro Asn Ala Lys Val Arg Gly Val Pro Val Asn Val Ser Asn Tyr Asn
                245                 250                 255

Gln Tyr Arg Ala Glu Val Arg Glu Pro Phe Thr Glu Trp Lys Asp Ala
                260                 265                 270

Trp Asp Glu Ser Arg Tyr Val Asn Val Leu Thr Pro His Leu Asn Ala
                275                 280                 285

Val Gly Phe Ser Ala His Phe Ile Val Asp Gln Gly Arg Gly Gly Lys
                290                 295                 300

Gly Gly Ile Arg Thr Glu Trp Gly Gln Trp Cys Asn Val Arg Asn Ala
305                 310                 315                 320

Gly Phe Gly Ile Arg Pro Thr Ala Asp Gln Gly Val Leu Gln Asn Pro
                325                 330                 335

Asn Val Asp Ala Ile Val Trp Val Lys Pro Gly Gly Glu Ser Asp Gly
                340                 345                 350

Thr Ser Asp Leu Asn Ser Asn Arg Tyr Asp Pro Thr Cys Arg Ser Pro
                355                 360                 365

Val Ala His Val Pro Ala Pro Glu Ala Gly Gln Trp Phe Asn Glu Tyr
                370                 375                 380

Val Val Asn Leu Val Leu Asn Ala Asn Pro Pro Leu Glu Pro Thr Trp
385                 390                 395                 400

<210> SEQ ID NO 31
<211> LENGTH: 1501
<212> TYPE: DNA
<213> ORGANISM: Thielavia terrestris

<400> SEQUENCE: 31
gccgttgtca agatgggcca agacgctg cacggattcg ccgccacggc tttggccgtt      60
ctcccctttg tgaaggctca gcagcccggc aacttcacgc cggaggtgca cccgcaactg     120
ccaacgtgga agtgcacgac cgccggcggc tgcgttcagc aggacacttc ggtggtgctc     180
gactggaact accgttggat ccacaatgcc gacggcaccg cctcgtgcac gacgtccagc     240
ggggtcgacc acacgctgtg tccagatgag gcgacctgcg cgaagaactg cttcgtggaa     300
ggcgtcaact acacgagcag cggtgtcacc acatccggca gttcgctgac gatgaggcag     360
tatttcaagg ggagcaacgg gcagaccaac agcgtttcgc ctcgtctcta cctgctcggc     420
tcggatggaa actacgtaat gctcaagctg ctcggccagg agctgagctt cgatgtcgat     480
ctctccacgc tcccctgcgg cgagaacggc gcgctgtacc tgtccgagat ggacgcgacc     540
ggtggcagga accagtacaa caccggcggt gccaactacg gctcgggcta ctgtgacgcc     600
cagtgtcccg tgcagacgtg gatgaacggc acgctgaaca ccaacgggca gggctactgc     660
```

-continued

```
tgcaacgaga tggacatcct cgaggccaac tcccgcgcca acgcgatgac acctcacccc      720
tgcgccaacg gcagctgcga caagagcggg tgcggactca accctacgc cgagggctac       780 aagagctact acggaccggg cctcacggtt gacacgtcga agcccttcac catcattacc      840
cgcttcatca ccgacgacgg cacgaccagc ggcaccctca accagatcca gcggatctat      900
gtgcagaatg caagacggt cgcgtcggct gcgtccggag cgacatcat cacggcatcc        960 ggctgcacct cggcccaggc gttcggcggg ctggccaaca tgggcgcggc gcttggacgg      1020
ggcatggtgc tgaccttcag catctggaac gacgctgggg gctacatgaa ctggctcgac      1080
agcggcaaca acgcccgtg cagcagcacc gagggcaacc cgtccaacat cctggccaac       1140
tacccggaca cccacgtggt cttctccaac atccgctggg gagacatcgg ctcgacggtc      1200
caggtctcgg gaggcggcaa cggcggctcg accaccacca cgtcgaccac cacgctgagg      1260
acctcgacca cgaccaccac caccgccccg acggccactg ccacgcactg ggacaatgc       1320 ggcggaatcg gggtacgtca accgcctcct gcattctgtt gaggaagtta actaacgtgg      1380
cctacgcagt ggactggacc gaccgtctgc gaatcgccgt acgcatgcaa ggagctgaac      1440
ccctggtact accagtgcct ctaaagtatt gcagtgaagc catactccgt gctcggcatg      1500
g                                                                      1501
```

<210> SEQ ID NO 32
<211> LENGTH: 464
<212> TYPE: PRT
<213> ORGANISM: Thielavia terrestris

<400> SEQUENCE: 32

```
Met Gly Gln Lys Thr Leu His Gly Phe Ala Ala Thr Ala Leu Ala Val
1               5                   10                  15

Leu Pro Phe Val Lys Ala Gln Gln Pro Gly Asn Phe Thr Pro Glu Val
            20                  25                  30

His Pro Gln Leu Pro Thr Trp Lys Cys Thr Thr Ala Gly Gly Cys Val
        35                  40                  45

Gln Gln Asp Thr Ser Val Val Leu Asp Trp Asn Tyr Arg Trp Ile His
    50                  55                  60

Asn Ala Asp Gly Thr Ala Ser Cys Thr Thr Ser Ser Gly Val Asp His
65                  70                  75                  80

Thr Leu Cys Pro Asp Glu Ala Thr Cys Ala Lys Asn Cys Phe Val Glu
                85                  90                  95

Gly Val Asn Tyr Thr Ser Ser Gly Val Thr Thr Ser Gly Ser Ser Leu
            100                 105                 110

Thr Met Arg Gln Tyr Phe Lys Gly Ser Asn Gly Gln Thr Asn Ser Val
        115                 120                 125

Ser Pro Arg Leu Tyr Leu Leu Gly Ser Asp Gly Asn Tyr Val Met Leu
    130                 135                 140

Lys Leu Leu Gly Gln Glu Leu Ser Phe Asp Val Asp Leu Ser Thr Leu
145                 150                 155                 160

Pro Cys Gly Glu Asn Gly Ala Leu Tyr Leu Ser Glu Met Asp Ala Thr
                165                 170                 175

Gly Gly Arg Asn Gln Tyr Asn Thr Gly Gly Ala Asn Tyr Gly Ser Gly
            180                 185                 190

Tyr Cys Asp Ala Gln Cys Pro Val Gln Thr Trp Met Asn Gly Thr Leu
        195                 200                 205

Asn Thr Asn Gly Gln Gly Tyr Cys Cys Asn Glu Met Asp Ile Leu Glu
```

Ala Asn Ser Arg Ala Asn Ala Met Thr Pro His Pro Cys Ala Asn Gly
225                 230                 235                 240

Ser Cys Asp Lys Ser Gly Cys Gly Leu Asn Pro Tyr Ala Glu Gly Tyr
            245                 250                 255

Lys Ser Tyr Tyr Gly Pro Gly Leu Thr Val Asp Thr Ser Lys Pro Phe
                260                 265                 270

Thr Ile Ile Thr Arg Phe Ile Thr Asp Asp Gly Thr Thr Ser Gly Thr
            275                 280                 285

Leu Asn Gln Ile Gln Arg Ile Tyr Val Gln Asn Gly Lys Thr Val Ala
        290                 295                 300

Ser Ala Ala Ser Gly Gly Asp Ile Ile Thr Ala Ser Gly Cys Thr Ser
305                 310                 315                 320

Ala Gln Ala Phe Gly Gly Leu Ala Asn Met Gly Ala Ala Leu Gly Arg
                325                 330                 335

Gly Met Val Leu Thr Phe Ser Ile Trp Asn Asp Ala Gly Gly Tyr Met
                340                 345                 350

Asn Trp Leu Asp Ser Gly Asn Asn Gly Pro Cys Ser Ser Thr Glu Gly
            355                 360                 365

Asn Pro Ser Asn Ile Leu Ala Asn Tyr Pro Asp Thr His Val Val Phe
        370                 375                 380

Ser Asn Ile Arg Trp Gly Asp Ile Gly Ser Thr Val Gln Val Ser Gly
385                 390                 395                 400

Gly Gly Asn Gly Gly Ser Thr Thr Thr Ser Thr Thr Thr Leu Arg
                405                 410                 415

Thr Ser Thr Thr Thr Thr Thr Thr Ala Pro Thr Ala Thr Ala Thr His
                420                 425                 430

Trp Gly Gln Cys Gly Gly Ile Gly Trp Thr Gly Pro Thr Val Cys Glu
            435                 440                 445

Ser Pro Tyr Ala Cys Lys Glu Leu Asn Pro Trp Tyr Tyr Gln Cys Leu
        450                 455                 460

<210> SEQ ID NO 33
<211> LENGTH: 1368
<212> TYPE: DNA
<213> ORGANISM: Thielavia terrestris

<400> SEQUENCE: 33
accgatccgc tcgaagatgg cgcccaagtc tacagttctg gccgcctggc tgctctcctc     60
gctggccgcg gcccagcaga tcggcaaagc cgtgcccgag gtccacccca aactgacaac    120
gcagaagtgc actctccgcg gcgggtgcaa gcctgtccgc acctcggtcg tgctcgactc    180
gtccgcgcgc tcgctgcaca aggtcgggga ccccaacacc agctgcagcg tcggcggcga    240
cctgtgctcg gacgcgaagt cgtgcggcaa gaactgcgcg ctcgagggcg tcgactacgc    300
ggcccacggc gtggcgacca agggcgacgc cctcacgctg caccagtggc tcaaggggcc    360
cgacggcacc tacaggaccg tctcgccgcg cgtatacctc ctgggcgagg acgggaagaa    420
ctacgaggac ttcaagctgc tcaacgccga gctcagcttc gacgtcgacg tgtcccagct    480
cgtctgcggc atgaacggcg ccctgtactt ctccgagatg gagatggacg gcggccgcag    540
cccgctgaac ccggcgggcg ccacgtacgg cacgggctac tgcgacgcgc agtgccccaa    600
gttggacttt atcaacggcg aggtatttct tctctcttct gttttctttt tccatcgctt    660
tttctgaccg gaatccgccc tcttagctca acaccaacca cacgtacggg gcgtgctgca    720

```
acgagatgga catctgggag gccaacgcgc tggcgcaggc gctcacgccg cacccgtgca    780
acgcgacgcg ggtgtacaag tgcgacacgg cggacgagtg cgggcagccg gtgggcgtgt    840
gcgacgaatg ggggtgctcg tacaacccgt ccaacttcgg ggtcaaggac tactacgggc    900
gcaacctgac ggtggacacg aaccgcaagt tcacggtgac gacgcagttc gtgacgtcca    960
acgggcgggc ggacggcgag ctgaccgaga tccggcggct gtacgtgcag gacggcgtgg   1020
tgatccagaa ccacgcggtc acggcgggcg gggcgacgta cgacagcatc acggacggct   1080
tctgcaacgc gacggccacc tggacgcagc agcggggcgg gctcgcgcgc atgggcgagg   1140
ccatcggccg cggcatggtg ctcatcttca gcctgtgggt tgacaacggc ggcttcatga   1200
actggctcga cagcggcaac gccgggccct gcaacgccac cgagggcgac ccggccctga   1260
tcctgcagca gcaccggac gccagcgtca ccttctccaa catccgatgg ggcgagatcg   1320
gcagcacgta caagagcgag tgcagccact agagtagagc ttgtaatt              1368
```

<210> SEQ ID NO 34
<211> LENGTH: 423
<212> TYPE: PRT
<213> ORGANISM: Thielavia terrestris

<400> SEQUENCE: 34

```
Met Ala Pro Lys Ser Thr Val Leu Ala Ala Trp Leu Leu Ser Ser Leu
1               5                   10                  15

Ala Ala Ala Gln Gln Ile Gly Lys Ala Val Pro Glu Val His Pro Lys
                20                  25                  30

Leu Thr Thr Gln Lys Cys Thr Leu Arg Gly Gly Cys Lys Pro Val Arg
            35                  40                  45

Thr Ser Val Val Leu Asp Ser Ser Ala Arg Ser Leu His Lys Val Gly
        50                  55                  60

Asp Pro Asn Thr Ser Cys Ser Val Gly Gly Asp Leu Cys Ser Asp Ala
65                  70                  75                  80

Lys Ser Cys Gly Lys Asn Cys Ala Leu Glu Gly Val Asp Tyr Ala Ala
                85                  90                  95

His Gly Val Ala Thr Lys Gly Asp Ala Leu Thr Leu His Gln Trp Leu
            100                 105                 110

Lys Gly Ala Asp Gly Thr Tyr Arg Thr Val Ser Pro Arg Val Tyr Leu
        115                 120                 125

Leu Gly Glu Asp Gly Lys Asn Tyr Glu Asp Phe Lys Leu Leu Asn Ala
    130                 135                 140

Glu Leu Ser Phe Asp Val Asp Val Ser Gln Leu Val Cys Gly Met Asn
145                 150                 155                 160

Gly Ala Leu Tyr Phe Ser Glu Met Glu Met Asp Gly Gly Arg Ser Pro
                165                 170                 175

Leu Asn Pro Ala Gly Ala Thr Tyr Gly Thr Gly Tyr Cys Asp Ala Gln
            180                 185                 190

Cys Pro Lys Leu Asp Phe Ile Asn Gly Glu Leu Asn Thr Asn His Thr
        195                 200                 205

Tyr Gly Ala Cys Cys Asn Glu Met Asp Ile Trp Glu Ala Asn Ala Leu
    210                 215                 220

Ala Gln Ala Leu Thr Pro His Pro Cys Asn Ala Thr Arg Val Tyr Lys
225                 230                 235                 240

Cys Asp Thr Ala Asp Glu Cys Gly Gln Pro Val Gly Val Cys Asp Glu
                245                 250                 255

Trp Gly Cys Ser Tyr Asn Pro Ser Asn Phe Gly Val Lys Asp Tyr Tyr
```

```
              260                 265                 270
Gly Arg Asn Leu Thr Val Asp Thr Asn Arg Lys Phe Thr Val Thr Thr
            275                 280                 285

Gln Phe Val Thr Ser Asn Gly Arg Ala Asp Gly Glu Leu Thr Glu Ile
        290                 295                 300

Arg Arg Leu Tyr Val Gln Asp Gly Val Val Ile Gln Asn His Ala Val
305                 310                 315                 320

Thr Ala Gly Gly Ala Thr Tyr Asp Ser Ile Thr Asp Gly Phe Cys Asn
                325                 330                 335

Ala Thr Ala Thr Trp Thr Gln Gln Arg Gly Gly Leu Ala Arg Met Gly
            340                 345                 350

Glu Ala Ile Gly Arg Gly Met Val Leu Ile Phe Ser Leu Trp Val Asp
        355                 360                 365

Asn Gly Gly Phe Met Asn Trp Leu Asp Ser Gly Asn Ala Gly Pro Cys
    370                 375                 380

Asn Ala Thr Glu Gly Asp Pro Ala Leu Ile Leu Gln Gln His Pro Asp
385                 390                 395                 400

Ala Ser Val Thr Phe Ser Asn Ile Arg Trp Gly Glu Ile Gly Ser Thr
                405                 410                 415

Tyr Lys Ser Glu Cys Ser His
            420

<210> SEQ ID NO 35
<211> LENGTH: 1000
<212> TYPE: DNA
<213> ORGANISM: Thielavia terrestris

<400> SEQUENCE: 35
atgaccctac ggctccctgt catcagcctg ctggcctcgc tggcagcagg cgccgtcgtc      60
gtcccacggg cggagtttca ccccctctc ccgacttgga aatgcacgac ctccggggc      120 tgcgtgcagc agaacaccag cgtcgtcctg accgtgact cgaagtacgc cgcacacagc      180
gccggctcgc ggacggaatc ggattacgcg gcaatgggag tgtccacttc gggcaatgcc      240
gtgacgctgt accactacgt caagaccaac ggcaccctcg tccccgcttc gccgcgcatc      300
tacctcctgg gcgcggacgg caagtacgtg cttatggacc tcctcaacca ggagctgtcg      360
gtggacgtcg acttctcggc gctgccgtgc ggcgagaacg gggccttcta cctgtccgag      420
atggcggcgg acgggcgggg cgacgcgggg gcgggcgacg ggtactgcga cgcgcagtgc      480
cagggctact gctgcaacga gatggacatc ctcgaggcca actcgatggc gacggccatg      540
acgccgcacc cgtgcaaggg caacaactgc gaccgcagcg gctgcggcta caacccgtac      600
gccagcggcc agcgcggctt ctacgggccc ggcaagacgg tcgacacgag caagcccttc      660
accgtcgtca cgcagttcgc cgccagcggc ggcaagctga cccagatcac ccgcaagtac      720
atccagaacg gccgggagat cggcggcggc ggcaccatct ccagctgcgg ctccgagtct      780
tcgacgggcg gcctgaccgg catgggcgag gcgctggggc gcggaatggt gctggccatg      840
agcatctgga acgacgcggc ccaggagatg gcatggctcg atgccggcaa caacggccct      900
tgcgccagtg gccagggcag cccgtccgtc attcagtcgc agcatcccga cacccacgtc      960
gtcttctcca acatcaggtg gggcgacatc gggtctacca                          1000

<210> SEQ ID NO 36
<211> LENGTH: 336
<212> TYPE: PRT
<213> ORGANISM: Thielavia terrestris
```

<400> SEQUENCE: 36

```
Met Thr Leu Arg Leu Pro Val Ile Ser Leu Leu Ala Ser Leu Ala Ala
1               5                   10                  15
Gly Ala Val Val Pro Arg Ala Glu Phe His Pro Pro Leu Pro Thr
            20                  25                  30
Trp Lys Cys Thr Thr Ser Gly Gly Cys Val Gln Gln Asn Thr Ser Val
            35                  40                  45
Val Leu Asp Arg Asp Ser Lys Tyr Ala Ala His Ser Ala Gly Ser Arg
    50                  55                  60
Thr Glu Ser Asp Tyr Ala Ala Met Gly Val Ser Thr Ser Gly Asn Ala
65                  70                  75                  80
Val Thr Leu Tyr His Tyr Val Lys Thr Asn Gly Thr Leu Val Pro Ala
                85                  90                  95
Ser Pro Arg Ile Tyr Leu Leu Gly Ala Asp Gly Lys Tyr Val Leu Met
            100                 105                 110
Asp Leu Leu Asn Gln Glu Leu Ser Val Asp Val Asp Phe Ser Ala Leu
        115                 120                 125
Pro Cys Gly Glu Asn Gly Ala Phe Tyr Leu Ser Glu Met Ala Ala Asp
    130                 135                 140
Gly Arg Gly Asp Ala Gly Ala Gly Asp Gly Tyr Cys Asp Ala Gln Cys
145                 150                 155                 160
Gln Gly Tyr Cys Cys Asn Glu Met Asp Ile Leu Glu Ala Asn Ser Met
                165                 170                 175
Ala Thr Ala Met Thr Pro His Pro Cys Lys Gly Asn Asn Cys Asp Arg
            180                 185                 190
Ser Gly Cys Gly Tyr Asn Pro Tyr Ala Ser Gly Gln Arg Gly Phe Tyr
        195                 200                 205
Gly Pro Gly Lys Thr Val Asp Thr Ser Lys Pro Phe Thr Val Val Thr
    210                 215                 220
Gln Phe Ala Ala Ser Gly Gly Lys Leu Thr Gln Ile Thr Arg Lys Tyr
225                 230                 235                 240
Ile Gln Asn Gly Arg Glu Ile Gly Gly Gly Thr Ile Ser Ser Cys
                245                 250                 255
Gly Ser Glu Ser Ser Thr Gly Gly Leu Thr Gly Met Gly Glu Ala Leu
            260                 265                 270
Gly Arg Gly Met Val Leu Ala Met Ser Ile Trp Asn Asp Ala Ala Gln
        275                 280                 285
Glu Met Ala Trp Leu Asp Ala Gly Asn Asn Gly Pro Cys Ala Ser Gly
    290                 295                 300
Gln Gly Ser Pro Ser Val Ile Gln Ser Gln His Pro Asp Thr His Val
305                 310                 315                 320
Val Phe Ser Asn Ile Arg Trp Gly Asp Ile Gly Ser Thr Thr Lys Asn
                325                 330                 335
```

<210> SEQ ID NO 37
<211> LENGTH: 1480
<212> TYPE: DNA
<213> ORGANISM: Cladorrhinum foecundissimum

<400> SEQUENCE: 37

```
gatccgaatt cctcctctcg ttctttagtc acagaccaga catctgccca cgatggttca      60
caagttcgcc ctcctcaccg gcctcgccgc ctccctcgca tctgcccagc agatcggcac     120
cgtcgtcccc gagtctcacc ccaagcttcc caccaagcgc tgcactctcg ccggtggctg     180
```

```
ccagaccgtc gacacctcca tcgtcatcga cgccttccag cgtcccctcc acaagatcgg    240
cgacccttcc actccttgcg tcgtcggcgg ccctctctgc cccgacgcca agtcctgcgc    300
tgagaactgc gcgctcgagg gtgtcgacta tgcctcctgg ggcatcaaga ccgagggcga    360
cgccctaact ctcaaccagt ggatgcccga cccggcgaac cctggccagt acaagacgac    420
tactccccgt acttaccttg ttgctgagga cggcaagaac tacgaggatg tgaagctcct    480
ggctaaggag atctcgtttg atgccgatgt cagcaacctt ccctgcggca tgaacggtgc    540
tttctacttg tctgagatgt tgatggatgg tggacgtggc gacctcaacc ctgctggtgc    600
cgagtatggt accggttact gtgatgcgca gtgcttcaag ttggatttca tcaacggcga    660
ggccaacatc gaccaaaagc acggcgcctg ctgcaacgaa atggacattt cgaatccaa     720 ctcgcgcgcc aagaccttcg tcccccaccc ctgcaacatc acgcaggtct acaagtgcga    780
aggcgaagac gagtgcggcc agcccgtcgg cgtgtgcgac aagtgggggt gcggcttcaa    840
cgagtacaaa tggggcgtcg agtccttcta cggccggggc tcgcagttcg ccatcgactc    900
ctccaagaag ttcaccgtca ccacgcagtt cctgaccgac aacggcaagg aggacggcgt    960
cctcgtcgag atccgcgcct gtgtggcacca ggatggcaag ctgatcaaga acaccgctat   1020
ccaggttgag gagaactaca gcacggactc ggtgagcacc gagttctgcg agaagactgc   1080
ttctttcacc atgcagcgcg gtggtctcaa ggcgatgggc gaggctatcg gtcgtggtat   1140
ggtgctggtt ttcagcatct gggcggatga ttcgggtttt atgaactggt tggatgcgga   1200
gggtaatggc ccttgcagcg cgactgaggg cgatccgaag gagattgtca agaataagcc   1260
ggatgctagg gttacgttct caaacattag gattggtgag gttggtagca cgtatgctcc   1320
gggtgggaag tgcggtgtta agagcagggt tgctaggggg cttactgctt cttaaggggg   1380
gtgtgaagag aggaggaggt gttgttgggg gttggagatg ataattgggc gagatggtgt   1440
agagcgggtt ggttggatat gaatacgttg aattggatgt                          1480

<210> SEQ ID NO 38
<211> LENGTH: 440
<212> TYPE: PRT
<213> ORGANISM: Cladorrhinum foecundissimum

<400> SEQUENCE: 38

Met Val His Lys Phe Ala Leu Leu Thr Gly Leu Ala Ala Ser Leu Ala
1               5                   10                  15

Ser Ala Gln Gln Ile Gly Thr Val Val Pro Glu Ser His Pro Lys Leu
            20                  25                  30

Pro Thr Lys Arg Cys Thr Leu Ala Gly Gly Cys Gln Thr Val Asp Thr
        35                  40                  45

Ser Ile Val Ile Asp Ala Phe Gln Arg Pro Leu His Lys Ile Gly Asp
    50                  55                  60

Pro Ser Thr Pro Cys Val Val Gly Gly Pro Leu Cys Pro Asp Ala Lys
65                  70                  75                  80

Ser Cys Ala Glu Asn Cys Ala Leu Glu Gly Val Asp Tyr Ala Ser Trp
                85                  90                  95

Gly Ile Lys Thr Glu Gly Asp Ala Leu Thr Leu Asn Gln Trp Met Pro
            100                 105                 110

Asp Pro Ala Asn Pro Gly Gln Tyr Lys Thr Thr Pro Arg Thr Tyr
        115                 120                 125

Leu Val Ala Glu Asp Gly Lys Asn Tyr Glu Asp Val Lys Leu Leu Ala
    130                 135                 140
```

Lys Glu Ile Ser Phe Asp Ala Asp Val Ser Asn Leu Pro Cys Gly Met
145                 150                 155                 160

Asn Gly Ala Phe Tyr Leu Ser Glu Met Leu Met Asp Gly Gly Arg Gly
            165                 170                 175

Asp Leu Asn Pro Ala Gly Ala Glu Tyr Gly Thr Gly Tyr Cys Asp Ala
            180                 185                 190

Gln Cys Phe Lys Leu Asp Phe Ile Asn Gly Glu Ala Asn Ile Asp Gln
            195                 200                 205

Lys His Gly Ala Cys Cys Asn Glu Met Asp Ile Phe Glu Ser Asn Ser
            210                 215                 220

Arg Ala Lys Thr Phe Val Pro His Pro Cys Asn Ile Thr Gln Val Tyr
225                 230                 235                 240

Lys Cys Glu Gly Glu Asp Glu Cys Gly Gln Pro Val Gly Val Cys Asp
                245                 250                 255

Lys Trp Gly Cys Gly Phe Asn Glu Tyr Lys Trp Gly Val Glu Ser Phe
            260                 265                 270

Tyr Gly Arg Gly Ser Gln Phe Ala Ile Asp Ser Ser Lys Lys Phe Thr
            275                 280                 285

Val Thr Thr Gln Phe Leu Thr Asp Asn Gly Lys Glu Asp Gly Val Leu
            290                 295                 300

Val Glu Ile Arg Arg Leu Trp His Gln Asp Gly Lys Leu Ile Lys Asn
305                 310                 315                 320

Thr Ala Ile Gln Val Glu Glu Asn Tyr Ser Thr Asp Ser Val Ser Thr
                325                 330                 335

Glu Phe Cys Glu Lys Thr Ala Ser Phe Thr Met Gln Arg Gly Gly Leu
            340                 345                 350

Lys Ala Met Gly Glu Ala Ile Gly Arg Gly Met Val Leu Val Phe Ser
            355                 360                 365

Ile Trp Ala Asp Asp Ser Gly Phe Met Asn Trp Leu Asp Ala Glu Gly
            370                 375                 380

Asn Gly Pro Cys Ser Ala Thr Glu Gly Asp Pro Lys Glu Ile Val Lys
385                 390                 395                 400

Asn Lys Pro Asp Ala Arg Val Thr Phe Ser Asn Ile Arg Ile Gly Glu
                405                 410                 415

Val Gly Ser Thr Tyr Ala Pro Gly Gly Lys Cys Gly Val Lys Ser Arg
            420                 425                 430

Val Ala Arg Gly Leu Thr Ala Ser
            435                 440

<210> SEQ ID NO 39
<211> LENGTH: 1380
<212> TYPE: DNA
<213> ORGANISM: Trichoderma reesei

<400> SEQUENCE: 39
atggcgccct cagttacact gccgttgacc acggccatcc tggccattgc ccggctcgtc    60
gccgcccagc aaccgggtac cagcaccccc gaggtccatc ccaagttgac aacctacaag   120
tgtacaaagt ccgggggggtg cgtggcccag gacacctcgg tggtccttga ctggaactac   180
cgctggatgc acgacgcaaa ctacaactcg tgcaccgtca acgcggcgt caacaccacg   240 ctctgccctg acgaggcgac ctgtggcaag aactgcttca tcgagggcgt cgactacgcc   300
gcctcgggcg tcacgacctc gggcagcagc ctcaccatga accagtacat gcccagcagc   360
tctggcggct acagcagcgt ctctcctcgg ctgtatctcc tggactctga cggtgagtac   420

```
gtgatgctga agctcaacgg ccaggagctg agcttcgacg tcgacctctc tgctctgccg    480
tgtggagaga acggctcgct ctacctgtct cagatggacg agaacggggg cgccaaccag    540
tataacacgg ccggtgccaa ctacgggagc ggctactgcg atgctcagtg ccccgtccag    600
acatggagga acggcaccct caacactagc caccagggct tctgctgcaa cgagatggat    660
atcctggagg gcaactcgag ggcgaatgcc ttgaccccctc actcttgcac ggccacggcc    720
tgcgactctg ccggttgcgg cttcaacccc tatggcagcg gctacaaaag ctactacggc    780
cccggagata ccgttgacac ctccaagacc ttcaccatca tcacccagtt caacacggac    840
aacggctcgc cctcgggcaa ccttgtgagc atcacccgca agtaccagca aaacggcgtc    900
gacatcccca gcgcccagcc cggcggcgac accatctcgt cctgcccgtc cgcctcagcc    960
tacgccggcc tcgccaccat gggcaaggcc ctgagcagcg gcatggtgct cgtgttcagc   1020
atttggaacg acaacagcca gtacatgaac tggctcgaca gcggcaacgc cggccccctgc   1080
agcagcaccg agggcaaccc atccaacatc ctggccaaca accccaacac gcacgtcgtc   1140
ttctccaaca tccgctgggg agacattggg tctactacga actcgactgc gccccccgccc   1200
ccgcctgcgt ccagcacgac gttttcgact acacggagga gctcgacgac ttcgagcagc   1260
ccgagctgca cgcagactca ctgggggcag tgcggtggca ttgggtacag cgggtgcaag   1320
acgtgcacgt cgggcactac gtgccagtat agcaacgact actactcgca atgcctttag   1380
```

```
<210> SEQ ID NO 40
<211> LENGTH: 459
<212> TYPE: PRT
<213> ORGANISM: Trichoderma reesei

<400> SEQUENCE: 40
```

Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
            20                  25                  30

His Pro Lys Leu Thr Thr Tyr Lys Cys Thr Lys Ser Gly Gly Cys Val
        35                  40                  45

Ala Gln Asp Thr Ser Val Val Leu Asp Trp Asn Tyr Arg Trp Met His
    50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Phe Ile Glu Gly
                85                  90                  95

Val Asp Tyr Ala Ala Ser Gly Val Thr Thr Ser Gly Ser Ser Leu Thr
            100                 105                 110

Met Asn Gln Tyr Met Pro Ser Ser Gly Gly Tyr Ser Ser Val Ser
        115                 120                 125

Pro Arg Leu Tyr Leu Leu Asp Ser Asp Gly Glu Tyr Val Met Leu Lys
    130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
            180                 185                 190

Cys Asp Ala Gln Cys Pro Val Gln Thr Trp Arg Asn Gly Thr Leu Asn
        195                 200                 205

```
Thr Ser His Gln Gly Phe Cys Cys Asn Glu Met Asp Ile Leu Glu Gly
    210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
            260                 265                 270

Ile Ile Thr Gln Phe Asn Thr Asp Asn Gly Ser Pro Ser Gly Asn Leu
        275                 280                 285

Val Ser Ile Thr Arg Lys Tyr Gln Gln Asn Gly Val Asp Ile Pro Ser
290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Trp Asn Asp Asn Ser Gln Tyr Met Asn Trp Leu
            340                 345                 350

Asp Ser Gly Asn Ala Gly Pro Cys Ser Ser Thr Glu Gly Asn Pro Ser
        355                 360                 365

Asn Ile Leu Ala Asn Asn Pro Asn Thr His Val Val Phe Ser Asn Ile
370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
                405                 410                 415

Thr Ser Ser Ser Pro Ser Cys Thr Gln Thr His Trp Gly Gln Cys Gly
            420                 425                 430

Gly Ile Gly Tyr Ser Gly Cys Lys Thr Cys Thr Ser Gly Thr Thr Cys
        435                 440                 445

Gln Tyr Ser Asn Asp Tyr Tyr Ser Gln Cys Leu
450                 455
```

<210> SEQ ID NO 41
<211> LENGTH: 1545
<212> TYPE: DNA
<213> ORGANISM: Trichoderma reesei

<400> SEQUENCE: 41

```
atgtatcgga agttggccgt catctcggcc ttcttggcca cagctcgtgc tcagtcggcc      60
tgcactctcc aatcggagac tcacccgcct ctgacatggc agaaatgctc gtctggtggc     120
acgtgcactc aacagacagg ctccgtggtc atcgacgcca actggcgctg gactcacgct     180
acgaacagca gcacgaactg ctacgatggc aacacttgga gctcgaccct atgtcctgac     240
aacgagacct cgcgaagaa ctgctgtctg acggtgccg cctacgcgtc cacgtacgga     300
gttaccacga gcggtaacag cctctccatt ggctttgtca cccagtctgc gcagaagaac     360
gttggcgctc gcctttacct tatggcgagc gacacgacct accaggaatt caccctgctt     420
ggcaacgagt tctctttcga tgttgatgtt tcgcagctgc cgtgcggctt gaacggagct     480
ctctacttcg tgtccatgga cgcggatggt ggcgtgagca agtatcccac caacaccgct     540
ggcgccaagt acggcacggg gtactgtgac agccagtgtc ccgcgatct gaagttcatc     600
aatggccagg ccaacgttga gggctgggag ccgtcatcca caacgcgaa cacgggcatt     660
```

```
ggaggacacg gaagctgctg ctctgagatg gatatctggg aggccaactc catctccgag    720
gctcttaccc cccacccttg cacgactgtc ggccaggaga tctgcgaggg tgatgggtgc    780
ggcggaactt actccgataa cagatatggc ggcacttgcg atcccgatgg ctgcgactgg    840
aacccatacc gcctgggcaa caccagcttc tacggccctg gctcaagctt taccctcgat    900
accaccaaga aattgaccgt tgtcacccag ttcgagacgt cgggtgccat caaccgatac    960
tatgtccaga atggcgtcac tttccagcag cccaacgccg agcttggtag ttactctggc   1020
aacgagctca acgatgatta ctgcacagct gaggaggcag aattcggcgg atcctctttc   1080
tcagacaagg gcggcctgac tcagttcaag aaggctacct ctggcggcat ggttctggtc   1140
atgagtctgt gggatgatta ctacgccaac atgctgtggc tggactccac ctacccgaca   1200
aacgagacct cctccacacc cggtgccgtg cgcggaagct gctccaccag ctccggtgtc   1260
cctgctcagg tcgaatctca gtctcccaac gccaaggtca ccttctccaa catcaagttc   1320
ggacccattg gcagcaccgg caaccctagc ggcggcaacc ctcccggcgg aaacccgcct   1380
ggcaccacca ccacccgccg cccagccact accactggaa gctctcccgg acctacccag   1440
tctcactacg gccagtgcgg cggtattggc tacagcggcc ccacggtctg cgccagcggc   1500
acaacttgcc aggtcctgaa cccttactac tctcagtgcc tgtaa                   1545
```

<210> SEQ ID NO 42
<211> LENGTH: 514
<212> TYPE: PRT
<213> ORGANISM: Trichoderma reesei

<400> SEQUENCE: 42

```
Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220
```

```
Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
            245                 250                 255

Gly Asp Gly Cys Gly Gly Thr Tyr Ser Asp Asn Arg Tyr Gly Gly Thr
        260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
            405                 410                 415

Ser Ser Gly Val Pro Ala Gln Val Glu Ser Gln Ser Pro Asn Ala Lys
        420                 425                 430

Val Thr Phe Ser Asn Ile Lys Phe Gly Pro Ile Gly Ser Thr Gly Asn
        435                 440                 445

Pro Ser Gly Gly Asn Pro Pro Gly Gly Asn Pro Pro Gly Thr Thr Thr
    450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
            485                 490                 495

Cys Ala Ser Gly Thr Thr Cys Gln Val Leu Asn Pro Tyr Tyr Ser Gln
            500                 505                 510

Cys Leu

<210> SEQ ID NO 43
<211> LENGTH: 1611
<212> TYPE: DNA
<213> ORGANISM: Trichoderma reesei

<400> SEQUENCE: 43
atgattgtcg gcattctcac cacgctggct acgctggcca cactcgcagc tagtgtgcct      60
ctagaggagc ggcaagcttg ctcaagcgtc tggtaattat gtgaaccctc tcaagagacc     120
caaatactga gatatgtcaa ggggccaatg tggtggccag aattggtcgg gtccgacttg     180
ctgtgcttcc ggaagcacat gcgtctactc aacgactact actcccagt gtcttcccgg     240 cgctgcaagc tcaagctcgt ccacgcgcgc gcgtcgacg acttctcgag tatcccccac     300
aacatcccgg tcgagctccg cgacgcctcc acctggttct actactacca gagtacctcc     360
agtcggatcg ggaaccgcta cgtattcagg caacccttt gttggggtca ctccttgggc     420
```

```
caatgcatat tacgcctctg aagttagcag cctcgctatt cctagcttga ctggagccat    480
ggccactgct gcagcagctg tcgcaaaggt tccctctttt atgtggctgt aggtcctccc    540
ggaaccaagg caatctgtta ctgaaggctc atcattcact gcagagatac tcttgacaag    600
acccctctca tggagcaaac cttggccgac atccgcaccg ccaacaagaa tggcggtaac    660
tatgccggac agtttgtggt gtatgacttg ccggatcgcg attgcgctgc ccttgcctcg    720
aatggcgaat actctattgc cgatggtggc gtcgccaaat ataagaacta tatcgacacc    780
attcgtcaaa ttgtcgtgga atattccgat atccggaccc tcctggttat tggtatgagt    840
ttaaacacct gcctcccccc cccctttccct tcctttcccg ccggcatctt gtcgttgtgc    900
taactattgt tccctcttcc agagcctgac tctcttgcca acctggtgac caacctcggt    960
actccaaagt gtgccaatgc tcagtcagcc taccttgagt gcatcaacta cgccgtcaca   1020
cagctgaacc ttccaaatgt tgcgatgtat ttggacgctg gccatgcagg atggcttggc   1080
tggccggcaa accaagaccc ggccgctcag ctatttgcaa atgtttacaa gaatgcatcg   1140
tctccgagag ctcttcgcgg attggcaacc aatgtcgcca actacaacgg gtggaacatt   1200
accagccccc catcgtacac gcaaggcaac gctgtctaca cgagaagct gtacatccac    1260
gctattggac gtcttcttgc caatcacggc tggtccaacg ccttcttcat cactgatcaa   1320
ggtcgatcgg gaaagcagcc taccggacag caacagtggg gagactggtg caatgtgatc   1380
ggcaccggat ttggtattcg cccatccgca acactgggg actcgttgct ggattcgttt   1440
gtctgggtca agccaggcgg cgagtgtgac ggcaccagcg acagcagtgc gccacgattt   1500
gactcccact gtgcgctccc agatgccttg caaccggcgc ctcaagctgg tgcttggttc   1560
caagcctact ttgtgcagct tctcacaaac gcaaacccat cgttcctgta a              1611

<210> SEQ ID NO 44
<211> LENGTH: 471
<212> TYPE: PRT
<213> ORGANISM: Trichoderma reesei

<400> SEQUENCE: 44

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Ser Thr Arg Ala Ala Ser Thr Thr Ser Arg
65                  70                  75                  80

Val Ser Pro Thr Thr Ser Arg Ser Ser Ser Ala Thr Pro Pro Pro Gly
                85                  90                  95

Ser Thr Thr Thr Arg Val Pro Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
    130                 135                 140

Ala Thr Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
```

```
                  165                 170                 175
Arg Thr Ala Asn Lys Asn Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asp Gly Val Ala Lys Tyr Lys Asn Tyr Ile Asp
    210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
        275                 280                 285

Gly His Ala Gly Trp Leu Gly Trp Pro Ala Asn Gln Asp Pro Ala Ala
    290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Arg Leu Leu Ala Asn His Gly Trp Ser Asn
        355                 360                 365

Ala Phe Phe Ile Thr Asp Gln Gly Arg Ser Gly Lys Gln Pro Thr Gly
    370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
            420                 425                 430

Pro Arg Phe Asp Ser His Cys Ala Leu Pro Asp Ala Leu Gln Pro Ala
        435                 440                 445

Pro Gln Ala Gly Ala Trp Phe Gln Ala Tyr Phe Val Gln Leu Leu Thr
    450                 455                 460

Asn Ala Asn Pro Ser Phe Leu
465                 470

<210> SEQ ID NO 45
<211> LENGTH: 2046
<212> TYPE: DNA
<213> ORGANISM: Humicola insolens

<400> SEQUENCE: 45
gccgtgacct tgcgcgcttt gggtggcggt ggcgagtcgt ggacggtgct tgctggtcgc      60
cggccttccc ggcgatccgc gtgatgagag ggccaccaac ggcgggatga tgctccatgg     120
ggaacttccc catggagaag agagagaaac ttgcggagcc gtgatctggg aaagatgct      180 ccgtgtctcg tctatataac tcgagtctcc ccgagccctc aacaccacca gctctgatct     240
caccatcccc atcgacaatc acgcaaacac agcagttgtc gggccattcc ttcagacaca     300
tcagtcaccc tccttcaaaa tgcgtaccgc caagttcgcc accctcgccg cccttgtggc     360
```

```
ctcggccgcc gcccagcagg cgtgcagtct caccaccgag aggcacccttc cctctcttg      420 gaacaagtgc accgccggcg gccagtgcca gaccgtccag gcttccatca ctctcgactc      480
caactggcgc tggactcacc aggtgtctgg ctccaccaac tgctacacgg caacaagtg      540 ggatactagc atctgcactg atgccaagtc gtgcgctcag aactgctgcg tcgatggtgc      600
cgactacacc agcacctatg gcatcaccac caacggtgat ccctgagcc tcaagttcgt      660 caccaagggc cagcactcga ccaacgtcgg ctcgcgtacc tacctgatgg acggcgagga      720
caagtatcag agtacgttct atcttcagcc ttctcgcgcc ttgaatcctg gctaacgttt      780
acacttcaca gccttcgagc tcctcggcaa cgagttcacc ttcgatgtcg atgtctccaa      840
catcggctgc ggtctcaacg gcgccctgta cttcgtctcc atggacgccg atggtggtct      900
cagccgctat cctggcaaca aggctggtgc caagtacggt accggctact gcgatgctca      960
gtgcccccgt gacatcaagt tcatcaacgg cgaggccaac attgagggct ggaccggctc     1020
caccaacgac cccaacgccg cgcgcgggccg ctatggtacc tgctgctctg agatggatat     1080
ctgggaagcc aacaacatgg ctactgcctt cactcctcac ccttgcacca tcattggcca     1140
gagccgctgc gagggcgact cgtgcggtgg cacctacagc aacgagcgct acgccggcgt     1200
ctgcgacccc gatggctgcg acttcaactc gtaccgccag ggcaacaaga ccttctacgg     1260
caagggcatg accgtcgaca ccaccaagaa gatcactgtc gtcacccagt tcctcaagga     1320
tgccaacggc gatctcggcg agatcaagcg cttctacgtc caggatggca agatcatccc     1380
caactccgag tccaccatcc ccggcgtcga gggcaattcc atcacccagg actggtgcga     1440
ccgccagaag gttgcctttg gcgacattga cgacttcaac cgcaagggcg gcatgaagca     1500
gatgggcaag gccctcgccg gccccatggt cctggtcatg tccatctggg atgaccacgc     1560
ctccaacatg ctctggctcg actcgacctt ccctgtcgat gccgctggca gcccggcgc     1620 cgagcgcggt gcctgcccga ccacctcggg tgtccctgct gaggttgagg ccgaggcccc     1680
caacagcaac gtcgtcttct ccaacatccg cttcggcccc atcggctcga ccgttgctgg     1740
tctccccggc gcgggcaacg gcggcaacaa cggcggcaac ccccgcccc ccaccaccac     1800 cacctcctcg gctccggcca ccaccaccac cgccagcgct ggcccaagg ctggccgctg     1860 gcagcagtgc ggcggcatcg gcttcactgg cccgacccag tgcgaggagc cctacatttg     1920
caccaagctc aacgactggt actctcagtg cctgtaaatt ctgagtcgct gactcgacga     1980
tcacggccgg ttttttgcatg aaaggaaaca aacgaccgcg ataaaaatgg agggtaatga     2040
gatgtc                                                               2046
```

<210> SEQ ID NO 46
<211> LENGTH: 525
<212> TYPE: PRT
<213> ORGANISM: Humicola insolens

<400> SEQUENCE: 46

Met Arg Thr Ala Lys Phe Ala Thr Leu Ala Ala Leu Val Ala Ser Ala
1               5                   10                  15

Ala Ala Gln Gln Ala Cys Ser Leu Thr Thr Glu Arg His Pro Ser Leu
                20                  25                  30

Ser Trp Asn Lys Cys Thr Ala Gly Gly Gln Cys Gln Thr Val Gln Ala
            35                  40                  45

Ser Ile Thr Leu Asp Ser Asn Trp Arg Trp Thr His Gln Val Ser Gly
        50                  55                  60

Ser Thr Asn Cys Tyr Thr Gly Asn Lys Trp Asp Thr Ser Ile Cys Thr

```
            65                  70                  75                  80
Asp Ala Lys Ser Cys Ala Gln Asn Cys Cys Val Asp Gly Ala Asp Tyr
                85                  90                  95

Thr Ser Thr Tyr Gly Ile Thr Thr Asn Gly Asp Ser Leu Ser Leu Lys
               100                 105                 110

Phe Val Thr Lys Gly Gln His Ser Thr Asn Val Gly Ser Arg Thr Tyr
               115                 120                 125

Leu Met Asp Gly Glu Asp Lys Tyr Gln Thr Phe Glu Leu Leu Gly Asn
    130                 135                 140

Glu Phe Thr Phe Asp Val Asp Val Ser Asn Ile Gly Cys Gly Leu Asn
145                 150                 155                 160

Gly Ala Leu Tyr Phe Val Ser Met Asp Ala Asp Gly Gly Leu Ser Arg
                165                 170                 175

Tyr Pro Gly Asn Lys Ala Gly Ala Lys Tyr Gly Thr Gly Tyr Cys Asp
                180                 185                 190

Ala Gln Cys Pro Arg Asp Ile Lys Phe Ile Asn Gly Glu Ala Asn Ile
        195                 200                 205

Glu Gly Trp Thr Gly Ser Thr Asn Asp Pro Asn Ala Gly Ala Gly Arg
    210                 215                 220

Tyr Gly Thr Cys Cys Ser Glu Met Asp Ile Trp Glu Ala Asn Asn Met
225                 230                 235                 240

Ala Thr Ala Phe Thr Pro His Pro Cys Thr Ile Ile Gly Gln Ser Arg
                245                 250                 255

Cys Glu Gly Asp Ser Cys Gly Gly Thr Tyr Ser Asn Glu Arg Tyr Ala
                260                 265                 270

Gly Val Cys Asp Pro Asp Gly Cys Asp Phe Asn Ser Tyr Arg Gln Gly
        275                 280                 285

Asn Lys Thr Phe Tyr Gly Lys Gly Met Thr Val Asp Thr Thr Lys Lys
    290                 295                 300

Ile Thr Val Val Thr Gln Phe Leu Lys Asp Ala Asn Gly Asp Leu Gly
305                 310                 315                 320

Glu Ile Lys Arg Phe Tyr Val Gln Asp Gly Lys Ile Ile Pro Asn Ser
                325                 330                 335

Glu Ser Thr Ile Pro Gly Val Glu Gly Asn Ser Ile Thr Gln Asp Trp
                340                 345                 350

Cys Asp Arg Gln Lys Val Ala Phe Gly Asp Ile Asp Asp Phe Asn Arg
        355                 360                 365

Lys Gly Gly Met Lys Gln Met Gly Lys Ala Leu Ala Gly Pro Met Val
    370                 375                 380

Leu Val Met Ser Ile Trp Asp Asp His Ala Ser Asn Met Leu Trp Leu
385                 390                 395                 400

Asp Ser Thr Phe Pro Val Asp Ala Ala Gly Lys Pro Gly Ala Glu Arg
                405                 410                 415

Gly Ala Cys Pro Thr Thr Ser Gly Val Pro Ala Glu Val Glu Ala Glu
                420                 425                 430

Ala Pro Asn Ser Asn Val Val Phe Ser Asn Ile Arg Phe Gly Pro Ile
        435                 440                 445

Gly Ser Thr Val Ala Gly Leu Pro Gly Ala Gly Asn Gly Gly Asn Asn
    450                 455                 460

Gly Gly Asn Pro Pro Pro Thr Thr Thr Ser Ser Ala Pro Ala
465                 470                 475                 480

Thr Thr Thr Thr Ala Ser Ala Gly Pro Lys Ala Gly Arg Trp Gln Gln
                485                 490                 495
```

```
Cys Gly Gly Ile Gly Phe Thr Gly Pro Thr Gln Cys Glu Glu Pro Tyr
            500                 505                 510

Ile Cys Thr Lys Leu Asn Asp Trp Tyr Ser Gln Cys Leu
            515                 520                 525

<210> SEQ ID NO 47
<211> LENGTH: 1812
<212> TYPE: DNA
<213> ORGANISM: Myceliophthora thermophila

<400> SEQUENCE: 47
atggccaaga agcttttcat caccgccgcc cttgcggctg ccgtgttggc ggccccgtc      60
attgaggagc gccagaactg cggcgctgtg tggtaagaaa gcccggtctg agtttcccat    120
gactttctca tcgagtaatg gcataaggcc acccccttcg actgactgtg agaatcgatc    180
aaatccagga ctcaatgcgg cggcaacggg tggcagggtc ccacatgctg cgcctcgggc    240
tcgacctgcg ttgcgcagaa cgagtggtac tctcagtgcc tgcccaacaa tcaggtgacg    300
agttccaaca ctccgtcgtc gacttccacc tcgcagcgca gcagcagcac ctccagcagc    360
agcaccagga gcggcagctc ctcctcctcc accaccacgc ccctcccgt ctccagcccc     420
gtgactagca ttcccggcgg tgcgaccacc acggcgagct actctggcaa cccttctcg     480
ggcgtccggc tcttcgccaa cgactactac aggtccgagg tccacaatct cgccattcct    540
agcatgaccg gtactctggc ggccaaggct tccgccgtcg ccgaagtccc tagcttccag    600
tggctcgacc ggaacgtcac catcgacacc ctgatggtcc agactctgtc ccagatccgg    660
gctgccaata atgccggtgc caatcctccc tatgctggtg agttacatgg cggcgacttg    720
ccttctcgtc ccccaccttt cttgacggga tcggttacct gacctggagg caaaacaaaa    780
ccagcccaac ttgtcgtcta cgacctcccc gaccgtgact gcgccgccgc tgcgtccaac    840
ggcgagtttt cgattgcaaa cggcggcgcc gccaactaca ggagctacat cgacgctatc    900
cgcaagcaca tcattgagta ctcggacatc cggatcatcc tggttatcga gcccgactcg    960
atggccaaca tggtgaccaa catgaacgtg ccaagtgca gcaacgccgc gtcgacgtac     1020
cacgagttga ccgtgtacgc gctcaagcag ctgaacctgc caacgtcgc catgtatctc     1080
gacgccggcc acgccggctg gctcggctgg cccgccaaca tccagcccgc gccgacctg    1140
tttgccggca tctacaatga cgccggcaag ccggctgccg tccgcggcct ggccactaac   1200
gtcgccaact acaacgcctg gagtatcgct tcggccccgt cgtacacgtc ccctaaccct   1260
aactacgacg agaagcacta catcgaggcc ttcagcccgc tcctgaacgc ggccggcttc   1320
cccgcacgct tcattgtcga cactggccgc aacggcaaac aacctaccgg tatggttttt   1380
ttcttttttt ttctctgttc ccctcccct tccccttcag ttggcgtcca caaggtctct    1440
tagtcttgct tcttctcgga ccaaccttcc cccacccca aaacgcaccg cccacaaccg    1500
ttcgactcta tactcttggg aatgggcgcc gaaactgacc gttcgacagg caacaacag    1560
tggggtgact ggtgcaatgt caagggcact ggctttggcg tgcgcccgac ggccaacacg   1620
ggccacgacc tggtcgatgc ctttgtctgg gtcaagcccg gcggcgagtc cgacggcaca   1680
agcgacacca gcgccgcccg ctacgactac cactgcggcc tgtccgatgc cctgcagcct   1740
gctccggagg ctggacagtg gttccaggcc tacttcgagc agctgctcac caacgccaac   1800
ccgcccttct aa                                                       1812

<210> SEQ ID NO 48
```

<211> LENGTH: 482
<212> TYPE: PRT
<213> ORGANISM: Myceliophthora thermophila

<400> SEQUENCE: 48

```
Met Ala Lys Lys Leu Phe Ile Thr Ala Ala Leu Ala Ala Val Leu
1               5                   10                  15

Ala Ala Pro Val Ile Glu Glu Arg Gln Asn Cys Gly Ala Val Trp Thr
            20                  25                  30

Gln Cys Gly Gly Asn Gly Trp Gln Gly Pro Thr Cys Cys Ala Ser Gly
        35                  40                  45

Ser Thr Cys Val Ala Gln Asn Glu Trp Tyr Ser Gln Cys Leu Pro Asn
    50                  55                  60

Asn Gln Val Thr Ser Ser Asn Thr Pro Ser Ser Thr Ser Thr Ser Gln
65                  70                  75                  80

Arg Ser Ser Ser Thr Ser Ser Ser Thr Arg Ser Gly Ser Ser Ser
                85                  90                  95

Ser Ser Thr Thr Thr Pro Pro Val Ser Ser Pro Thr Ser Ile
                100                 105                 110

Pro Gly Gly Ala Thr Thr Thr Ala Ser Tyr Ser Gly Asn Pro Phe Ser
            115                 120                 125

Gly Val Arg Leu Phe Ala Asn Asp Tyr Tyr Arg Ser Glu Val His Asn
        130                 135                 140

Leu Ala Ile Pro Ser Met Thr Gly Thr Leu Ala Ala Lys Ala Ser Ala
145                 150                 155                 160

Val Ala Glu Val Pro Ser Phe Gln Trp Leu Asp Arg Asn Val Thr Ile
                165                 170                 175

Asp Thr Leu Met Val Gln Thr Leu Ser Gln Ile Arg Ala Ala Asn Asn
            180                 185                 190

Ala Gly Ala Asn Pro Pro Tyr Ala Ala Gln Leu Val Val Tyr Asp Leu
        195                 200                 205

Pro Asp Arg Asp Cys Ala Ala Ala Ala Ser Asn Gly Glu Phe Ser Ile
    210                 215                 220

Ala Asn Gly Gly Ala Ala Asn Tyr Arg Ser Tyr Ile Asp Ala Ile Arg
225                 230                 235                 240

Lys His Ile Ile Glu Tyr Ser Asp Ile Arg Ile Ile Leu Val Ile Glu
                245                 250                 255

Pro Asp Ser Met Ala Asn Met Val Thr Asn Met Asn Val Ala Lys Cys
            260                 265                 270

Ser Asn Ala Ala Ser Thr Tyr His Glu Leu Thr Val Tyr Ala Leu Lys
        275                 280                 285

Gln Leu Asn Leu Pro Asn Val Ala Met Tyr Leu Asp Ala Gly His Ala
    290                 295                 300

Gly Trp Leu Gly Trp Pro Ala Asn Ile Gln Pro Ala Ala Asp Leu Phe
305                 310                 315                 320

Ala Gly Ile Tyr Asn Asp Ala Gly Lys Pro Ala Ala Val Arg Gly Leu
                325                 330                 335

Ala Thr Asn Val Ala Asn Tyr Asn Ala Trp Ser Ile Ala Ser Ala Pro
            340                 345                 350

Ser Tyr Thr Ser Pro Asn Pro Asn Tyr Asp Glu Lys His Tyr Ile Glu
        355                 360                 365

Ala Phe Ser Pro Leu Leu Asn Ala Ala Gly Phe Pro Ala Arg Phe Ile
    370                 375                 380

Val Asp Thr Gly Arg Asn Gly Lys Gln Pro Thr Gly Gln Gln Gln Trp
```

| | | | | 385 | | | 390 | | | 395 | | | 400 | |
|---|---|---|---|---|---|---|---|---|---|---|---|---|---|---|

Gly Asp Trp Cys Asn Val Lys Gly Thr Gly Phe Gly Val Arg Pro Thr
                        405                      410                      415

Ala Asn Thr Gly His Asp Leu Val Asp Ala Phe Val Trp Val Lys Pro
                  420                      425                      430

Gly Gly Glu Ser Asp Gly Thr Ser Asp Thr Ser Ala Ala Arg Tyr Asp
              435                      440                      445

Tyr His Cys Gly Leu Ser Asp Ala Leu Gln Pro Ala Pro Glu Ala Gly
      450                      455                      460

Gln Trp Phe Gln Ala Tyr Phe Glu Gln Leu Leu Thr Asn Ala Asn Pro
465                      470                      475                      480

Pro Phe

```
<210> SEQ ID NO 49
<211> LENGTH: 1725
<212> TYPE: DNA
<213> ORGANISM: Trichoderma reesei

<400> SEQUENCE: 49
gagggcagct cacctgaaga ggcttgtaag atcaccctct gtgtattgca ccatgattgt     60
cggcattctc accacgctgg ctacgctggc cacactcgca gctagtgtgc ctctagagga    120
gcggcaagct tgctcaagcg tctggggcca atgtggtggc cagaattggt cgggtccgac    180
ttgctgtgct tccggaagca catgcgtcta ctccaacgac tattactccc agtgtcttcc    240
cggcgctgca agctcaagct cgtccacgcg cgccgcgtcg acgacttctc gagtatcccc    300
cacaacatcc cggtcgagct ccgcgacgcc tccacctggt tctactacta ccagagtacc    360
tccagtcgga tcgggaaccg ctacgtattc aggcaaccct tttgttgggg tcactccttg    420
ggccaatgca tattacgcct ctgaagttag cagcctcgct attcctagct tgactggagc    480
catggccact gctgcagcag ctgtcgcaaa ggttccctct tttatgtggc tagatactct    540
tgacaagacc cctctcatgg agcaaacctt ggccgacatc cgcaccgcca acaagaatgg    600
cggtaactat gccggacagt tgtggtgta tgacttgccg gatcgcgatt gcgctgccct    660
tgcctcgaat ggcgaatact ctattgccga tggtggcgtc gccaaatata agaactatat    720
cgacaccatt cgtcaaattg tcgtggaata ttccgatatc cggaccctcc tggttattga    780
gcctgactct cttgccaacc tggtgaccaa cctcggtact ccaaagtgtg ccaatgctca    840
gtcagcctac cttgagtgca tcaactacgc cgtcacacag ctgaaccttc aaatgttgc    900 gatgtatttg gacgctggcc atgcaggatg gcttggctgg ccggcaaacc aagacccggc    960
cgctcagcta tttgcaaatg tttacaagaa tgcatcgtct ccgagagctc ttcgcggatt   1020
ggcaaccaat gtcgccaact acaacgggtg gaacattacc agccccccat cgtacacgca   1080
aggcaacgct gtctacaacg agaagctgta catccacgct attggacctc ttcttgccaa   1140
tcacggctgg tccaacgcct tcttcatcac tgatcaaggt cgatcgggaa agcagcctac   1200
cggacagcaa cagtggggag actggtgcaa tgtgatcggc accggatttg gtattcgccc   1260
atccgcaaac actggggact cgttgctgga ttcgtttgtc tgggtcaagc caggcggcga   1320
gtgtgacggc accagcgaca gcagtgcgcc acgatttgac tcccactgtg cgctcccaga   1380
tgccttgcaa ccggcgcctc aagctggtgc ttggttccaa gcctactttg tgcagcttct   1440
cacaaacgca aacccatcgt tcctgtaagg ctttcgtgac cgggcttcaa acaatgatgt   1500
gcgatggtgt ggttcccggt tggcggagtc tttgtctact ttggttgtct gtcgcaggtc   1560
```

```
ggtagaccgc aaatgagcaa ctgatggatt gttgccagcg atactataat tcacatggat    1620
ggtctttgtc gatcagtagc tagtgagaga gagagaacat ctatccacaa tgtcgagtgt    1680
ctattagaca tactccgaga aaaaaaaaaa aaaaaaaaa aaaaa                      1725

<210> SEQ ID NO 50
<211> LENGTH: 471
<212> TYPE: PRT
<213> ORGANISM: Trichoderma reesei

<400> SEQUENCE: 50

Met Ile Val Gly Ile Leu Thr Thr Leu Ala Thr Leu Ala
1               5                   10              15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Ser Thr Arg Ala Ala Ser Thr Thr Ser Arg
65                  70                  75                  80

Val Ser Pro Thr Thr Ser Arg Ser Ser Ser Ala Thr Pro Pro Pro Gly
                85                  90                  95

Ser Thr Thr Thr Arg Val Pro Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
    130                 135                 140

Ala Thr Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
    210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
        275                 280                 285

Gly His Ala Gly Trp Leu Gly Trp Pro Ala Asn Gln Asp Pro Ala Ala
    290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350
```

```
Tyr Ile His Ala Ile Gly Pro Leu Leu Ala Asn His Gly Trp Ser Asn
        355                 360                 365

Ala Phe Phe Ile Thr Asp Gln Gly Arg Ser Gly Lys Gln Pro Thr Gly
    370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
            420                 425                 430

Pro Arg Phe Asp Ser His Cys Ala Leu Pro Asp Ala Leu Gln Pro Ala
        435                 440                 445

Pro Gln Ala Gly Ala Trp Phe Gln Ala Tyr Phe Val Gln Leu Leu Thr
    450                 455                 460

Asn Ala Asn Pro Ser Phe Leu
465                 470

<210> SEQ ID NO 51
<211> LENGTH: 1446
<212> TYPE: DNA
<213> ORGANISM: Thielavia terrestris

<400> SEQUENCE: 51
atggctcaga agctccttct cgccgccgcc cttgcggcca gcgccctcgc tgctcccgtc      60
gtcgaggagc gccagaactg cggttccgtc tggagccaat gcggcggcat tggctggtcc     120
ggcgcgacct gctgcgcttc gggcaatacc tgcgttgagc tgaacccgta ctactcgcag     180
tgcctgccca cagccaggt gactacctcg accagcaaga ccacctccac caccaccagg     240
agcagcacca ccagccacag cagcggtccc accagcacga gcaccaccac caccagcagt     300
cccgtggtca ctaccccgcc gagtacctcc atccccggcg gtgcctcgtc aacggccagc     360
tggtccggca accgttctc gggcgtgcag atgtgggcca cgactacta cgcctccgag     420 gtctcgtcgc tggccatccc cagcatgacg ggcgccatgg ccaccaaggc ggccgaggtg     480
gccaaggtgc ccagcttcca gtggcttgac cgcaacgtca ccatcgacac gctgttcgcc     540
cacacgctgt cgcagatccg cgcggccaac cagaaaggcg ccaacccgcc ctacgcgggc     600
atcttcgtgg tctacgacct ccggaccgc gactgcgccg ccgccgcgtc caacggcgag     660
ttctccatcg cgaacaacgg ggcggccaac tacaagacgt acatcgacgc gatccggagc     720
ctcgtcatcc agtactcaga catccgcatc atcttcgtca tcgagcccga ctcgctggcc     780
aacatggtga ccaacctgaa cgtggccaag tgcgccaacg ccgagtcgac ctacaaggag     840
ttgaccgtct acgcgctgca gcagctgaac ctgcccaacg tggccatgta cctggacgcc     900
ggccacgccg gctggctcgg ctggcccgcc aacatccagc cggccgccaa cctcttcgcc     960
gagatctaca cgagcgccgg caagccggcc gccgtgcgcg gcctcgccac caacgtggcc    1020
aactacaacg gctggagcct ggccacgccg ccctcgtaca cccagggcga ccccaactac    1080
gacgagagcc actacgtcca ggccctcgcc ccgctgctca ccgccaacgg cttccccgcc    1140
cacttcatca ccgacaccgg ccgcaacggc aagcagccga ccggacaacg gcaatgggga    1200
gactggtgca acgttatcgg aactggcttc ggcgtgcgcc cgacgacaaa caccggcctc    1260
gacatcgagg acgccttcgt ctgggtcaag cccggcggcg agtgcgacgg cacgagcaac    1320
acgacctctc cccgctacga ctaccactgc ggcctgtcgg acgcgctgca gcctgctccg    1380
```

```
gaggccggca cttggttcca ggcctacttc gagcagctcc tgaccaacgc caacccgccc    1440
ttttaa                                                                1446
```

<210> SEQ ID NO 52
<211> LENGTH: 481
<212> TYPE: PRT
<213> ORGANISM: Thielavia terrestris

<400> SEQUENCE: 52

```
Met Ala Gln Lys Leu Leu Leu Ala Ala Ala Leu Ala Ala Ser Ala Leu
 1               5                  10                  15

Ala Ala Pro Val Val Glu Glu Arg Gln Asn Cys Gly Ser Val Trp Ser
             20                  25                  30

Gln Cys Gly Gly Ile Gly Trp Ser Gly Ala Thr Cys Cys Ala Ser Gly
         35                  40                  45

Asn Thr Cys Val Glu Leu Asn Pro Tyr Tyr Ser Gln Cys Leu Pro Asn
     50                  55                  60

Ser Gln Val Thr Thr Ser Thr Lys Thr Thr Ser Thr Thr Thr Arg
 65                  70                  75                  80

Ser Ser Thr Thr Ser His Ser Ser Gly Pro Thr Ser Thr Ser Thr Thr
                 85                  90                  95

Thr Thr Ser Ser Pro Val Val Thr Thr Pro Pro Ser Thr Ser Ile Pro
            100                 105                 110

Gly Gly Ala Ser Ser Thr Ala Ser Trp Ser Gly Asn Pro Phe Ser Gly
        115                 120                 125

Val Gln Met Trp Ala Asn Asp Tyr Tyr Ala Ser Glu Val Ser Ser Leu
    130                 135                 140

Ala Ile Pro Ser Met Thr Gly Ala Met Ala Thr Lys Ala Ala Glu Val
145                 150                 155                 160

Ala Lys Val Pro Ser Phe Gln Trp Leu Asp Arg Asn Val Thr Ile Asp
                165                 170                 175

Thr Leu Phe Ala His Thr Leu Ser Gln Ile Arg Ala Ala Asn Gln Lys
            180                 185                 190

Gly Ala Asn Pro Pro Tyr Ala Gly Ile Phe Val Val Tyr Asp Leu Pro
        195                 200                 205

Asp Arg Asp Cys Ala Ala Ala Ser Asn Gly Glu Phe Ser Ile Ala
    210                 215                 220

Asn Asn Gly Ala Ala Asn Tyr Lys Thr Tyr Ile Asp Ala Ile Arg Ser
225                 230                 235                 240

Leu Val Ile Gln Tyr Ser Asp Ile Arg Ile Phe Val Ile Glu Pro
                245                 250                 255

Asp Ser Leu Ala Asn Met Val Thr Asn Leu Asn Val Ala Lys Cys Ala
            260                 265                 270

Asn Ala Glu Ser Thr Tyr Lys Glu Leu Thr Val Tyr Ala Leu Gln Gln
        275                 280                 285

Leu Asn Leu Pro Asn Val Ala Met Tyr Leu Asp Ala Gly His Ala Gly
    290                 295                 300

Trp Leu Gly Trp Pro Ala Asn Ile Gln Pro Ala Ala Asn Leu Phe Ala
305                 310                 315                 320

Glu Ile Tyr Thr Ser Ala Gly Lys Pro Ala Ala Val Arg Gly Leu Ala
                325                 330                 335

Thr Asn Val Ala Asn Tyr Asn Gly Trp Ser Leu Ala Thr Pro Pro Ser
            340                 345                 350

Tyr Thr Gln Gly Asp Pro Asn Tyr Asp Glu Ser His Tyr Val Gln Ala
```

```
                355                 360                 365
Leu Ala Pro Leu Leu Thr Ala Asn Gly Phe Pro Ala His Phe Ile Thr
            370                 375                 380

Asp Thr Gly Arg Asn Gly Lys Gln Pro Thr Gly Gln Arg Gln Trp Gly
385                 390                 395                 400

Asp Trp Cys Asn Val Ile Gly Thr Gly Phe Gly Val Arg Pro Thr Thr
                405                 410                 415

Asn Thr Gly Leu Asp Ile Glu Asp Ala Phe Val Trp Val Lys Pro Gly
            420                 425                 430

Gly Glu Cys Asp Gly Thr Ser Asn Thr Thr Ser Pro Arg Tyr Asp Tyr
                435                 440                 445

His Cys Gly Leu Ser Asp Ala Leu Gln Pro Ala Pro Glu Ala Gly Thr
            450                 455                 460

Trp Phe Gln Ala Tyr Phe Glu Gln Leu Leu Thr Asn Ala Asn Pro Pro
465                 470                 475                 480

Phe

<210> SEQ ID NO 53
<211> LENGTH: 1593
<212> TYPE: DNA
<213> ORGANISM: Chaetomium thermophilum

<400> SEQUENCE: 53
atgatgtaca agaagttcgc cgctctcgcc gccctcgtgg ctggcgccgc cgcccagcag    60
gcttgctccc tcaccactga gacccacccc agactcactt ggaagcgctg cacctctggc   120
ggcaactgct cgaccgtgaa cggcgccgtc accatcgatg ccaactggcg ctggactcac   180
actgtttccg gctcgaccaa ctgctacacc ggcaacgagt gggatacctc catctgctct   240
gatggcaaga gctgcgccca gacctgctgc gtcgacggcg ctgactactc ttcgacctat   300
ggtatcacca ccagcggtga ctccctgaac ctcaagttcg tcaccaagca ccagcacggc   360
accaatgtcg gctctcgtgt ctacctgatg gagaacgaca ccaagtacca gatgttcgag   420
ctcctcggca acgagttcac cttcgatgtc gatgtctcta acctgggctg cggtctcaac   480
ggcgccctct acttcgtctc catggacgct gatggtggta tgagcaagta ctctggcaac   540
aaggctggcg ccaagtacgg taccggctac tgcgatgctc agtgcccgcg cgaccttaag   600
ttcatcaacg gcgaggccaa cattgagaac tggacccctt cgaccaatga tgccaacgcc   660
ggtttcggcc gctatggcag ctgctgctct gagatggata tctgggatgc aacaacatg    720 gctactgcct tcactcctca cccttgcacc attatcggcc agagccgctg cgagggcaac   780
agctgcggtg gcacctacag ctctgagcgc tatgctggtg tttgcgatcc tgatggctgc   840
gacttcaacg cctaccgcca gggcgacaag accttctacg caagggcat gaccgtcgac   900 accaccaaga gatgaccgt cgtcacccag ttccacaaga actcggctgg cgtcctcagc   960
gagatcaagc gcttctacgt tcaggacggc aagatcattg ccaacgccga gtccaagatc  1020
cccggcaacc ccggcaactc catcacccag gagtggtgcg atgcccagaa ggtcgccttc  1080
ggtgacatcg atgacttcaa ccgcaagggc ggtatggctc agatgagcaa ggccctcgag  1140
ggccctatgg tcctggtcat gtccgtctgg gatgaccact acgccaacat gctctggctc  1200
gactcgacct accccattga aaggccggc accccggcg ccgagcgcgg tgcttgcccg  1260
accacctccg gtgccctgc cgagattgag gcccaggtcc ccaacagcaa cgttatcttc  1320
tccaacatcc gcttcggccc catcggctcg accgtccctg gcctcgacgg cagcacccc  1380
```

```
agcaacccga  ccgccaccgt  tgctcctccc  acttctacca  ccaccagcgt  gagaagcagc      1440
actactcaga  tttccacccc  gactagccag  cccggcggct  gcaccaccca  gaagtggggc      1500
cagtgcggtg  gtatcggcta  caccggctgc  actaactgcg  ttgctggcac  tacctgcact      1560
gagctcaacc  cctggtacag  ccagtgcctg  taa                                    1593
```

<210> SEQ ID NO 54
<211> LENGTH: 530
<212> TYPE: PRT
<213> ORGANISM: Chaetomium thermophilum

<400> SEQUENCE: 54

```
Met Met Tyr Lys Lys Phe Ala Ala Leu Ala Ala Leu Val Ala Gly Ala
1               5                   10                  15

Ala Ala Gln Gln Ala Cys Ser Leu Thr Thr Glu Thr His Pro Arg Leu
            20                  25                  30

Thr Trp Lys Arg Cys Thr Ser Gly Gly Asn Cys Ser Thr Val Asn Gly
        35                  40                  45

Ala Val Thr Ile Asp Ala Asn Trp Arg Trp Thr His Thr Val Ser Gly
    50                  55                  60

Ser Thr Asn Cys Tyr Thr Gly Asn Glu Trp Asp Thr Ser Ile Cys Ser
65                  70                  75                  80

Asp Gly Lys Ser Cys Ala Gln Thr Cys Cys Val Asp Gly Ala Asp Tyr
                85                  90                  95

Ser Ser Thr Tyr Gly Ile Thr Thr Ser Gly Asp Ser Leu Asn Leu Lys
            100                 105                 110

Phe Val Thr Lys His Gln His Gly Thr Asn Val Gly Ser Arg Val Tyr
        115                 120                 125

Leu Met Glu Asn Asp Thr Lys Tyr Gln Met Phe Glu Leu Leu Gly Asn
    130                 135                 140

Glu Phe Thr Phe Asp Val Asp Val Ser Asn Leu Gly Cys Gly Leu Asn
145                 150                 155                 160

Gly Ala Leu Tyr Phe Val Ser Met Asp Ala Asp Gly Gly Met Ser Lys
                165                 170                 175

Tyr Ser Gly Asn Lys Ala Gly Ala Lys Tyr Gly Thr Gly Tyr Cys Asp
            180                 185                 190

Ala Gln Cys Pro Arg Asp Leu Lys Phe Ile Asn Gly Glu Ala Asn Ile
        195                 200                 205

Glu Asn Trp Thr Pro Ser Thr Asn Asp Ala Asn Ala Gly Phe Gly Arg
    210                 215                 220

Tyr Gly Ser Cys Cys Ser Glu Met Asp Ile Trp Asp Ala Asn Asn Met
225                 230                 235                 240

Ala Thr Ala Phe Thr Pro His Pro Cys Thr Ile Ile Gly Gln Ser Arg
                245                 250                 255

Cys Glu Gly Asn Ser Cys Gly Gly Thr Tyr Ser Ser Glu Arg Tyr Ala
            260                 265                 270

Gly Val Cys Asp Pro Asp Gly Cys Asp Phe Asn Ala Tyr Arg Gln Gly
        275                 280                 285

Asp Lys Thr Phe Tyr Gly Lys Gly Met Thr Val Asp Thr Thr Lys Lys
    290                 295                 300

Met Thr Val Val Thr Gln Phe His Lys Asn Ser Ala Gly Val Leu Ser
305                 310                 315                 320

Glu Ile Lys Arg Phe Tyr Val Gln Asp Gly Lys Ile Ile Ala Asn Ala
                325                 330                 335
```

```
Glu Ser Lys Ile Pro Gly Asn Pro Gly Asn Ser Ile Thr Gln Glu Trp
            340                 345                 350
Cys Asp Ala Gln Lys Val Ala Phe Gly Asp Ile Asp Asp Phe Asn Arg
        355                 360                 365
Lys Gly Gly Met Ala Gln Met Ser Lys Ala Leu Glu Gly Pro Met Val
    370                 375                 380
Leu Val Met Ser Val Trp Asp Asp His Tyr Ala Asn Met Leu Trp Leu
385                 390                 395                 400
Asp Ser Thr Tyr Pro Ile Asp Lys Ala Gly Thr Pro Gly Ala Glu Arg
                405                 410                 415
Gly Ala Cys Pro Thr Thr Ser Gly Val Pro Ala Glu Ile Glu Ala Gln
            420                 425                 430
Val Pro Asn Ser Asn Val Ile Phe Ser Asn Ile Arg Phe Gly Pro Ile
        435                 440                 445
Gly Ser Thr Val Pro Gly Leu Asp Gly Ser Thr Pro Ser Asn Pro Thr
    450                 455                 460
Ala Thr Val Ala Pro Pro Thr Ser Thr Thr Thr Ser Val Arg Ser Ser
465                 470                 475                 480
Thr Thr Gln Ile Ser Thr Pro Thr Ser Gln Pro Gly Gly Cys Thr Thr
                485                 490                 495
Gln Lys Trp Gly Gln Cys Gly Gly Ile Gly Tyr Thr Gly Cys Thr Asn
            500                 505                 510
Cys Val Ala Gly Thr Thr Cys Thr Glu Leu Asn Pro Trp Tyr Ser Gln
        515                 520                 525
Cys Leu
    530

<210> SEQ ID NO 55
<211> LENGTH: 1434
<212> TYPE: DNA
<213> ORGANISM: Chaetomium thermophilum

<400> SEQUENCE: 55
atggctaagc agctgctgct cactgccgct cttgcggcca cttcgctggc tgcccctctc    60
cttgaggagc gccagagctg ctcctccgtc tggggtcaat gcggtggcat caattacaac   120
ggcccgacct gctgccagtc cggcagtgtt tgcacttacc tgaatgactg gtacagccag   180
tgcattcccg gtcaggctca gcccggcacg actagcacca cggctcggac caccagcacc   240
agcaccacca gcacttcgtc ggtccgcccg accacctcga ataccctgt gacgactgct   300
cccccgacga ccaccatccc gggcggcgcc tcgagcacgg ccagctacaa cggcaacccg   360
ttttcgggtg ttcaactttg gccaacacc tactactcgt ccgaggtgca cactttggcc   420
atccccagct gtctcctga ctggctgcc aaggccgcca aggtcgctga ggttcccagc   480
ttccagtggc tcgaccgcaa tgtgactgtt gacactctct ctccggcac tcttgccgaa   540
atccgcgccg ccaaccagcg cggtgccaac ccgccttatg ccggcatttt cgtggtttat   600
gacttaccag accgtgattg cgcggctgct gcttcgaacg gcgagtggtc tatcgccaac   660
aatggtgcca acaactacaa gcgctacatc gaccggatcc gtgagctcct tatccagtac   720
tccgatatcc gcactattct ggtcattgaa cctgattccc tggccaacat ggtcaccaac   780
atgaacgtcc agaagtgctc gaacgctgcc tccacttaca aggagcttac tgtctatgcc   840
ctcaaacagc tcaatcttcc tcacgttgcc atgtacatgg atgctggcca cgctggctgg   900
cttggctggc ccgccaacat ccagcctgct gctgagctct tgctcaaat ctaccgcgac   960
```

```
gctggcaggc cgctgctgt ccgcggtctt gcgaccaacg ttgccaacta caatgcttgg    1020
tcgatcgcca gccctccgtc ctacacctct cctaacccga actacgacga gaagcactat    1080
attgaggcct ttgctcctct tctccgcaac cagggcttcg acgcaaagtt catcgtcgac    1140
accggccgta acggcaagca gcccactggc cagcttgaat ggggtcactg gtgcaatgtc    1200
aagggaactg gcttcggtgt cgccctact gctaacactg gcatgaact tgttgatgct    1260 ttcgtgtggg tcaagcccgg tggcgagtcc gacggcacca gtgcggacac cagcgctgct    1320
cgttatgact atcactgcgg cctttccgac gcactgactc cggcgcctga ggctggccaa    1380
tggttccagg cttatttcga acagctgctc atcaatgcca accctccgct ctga          1434
```

<210> SEQ ID NO 56
<211> LENGTH: 477
<212> TYPE: PRT
<213> ORGANISM: Chaetomium thermophilum

<400> SEQUENCE: 56

```
Met Ala Lys Gln Leu Leu Thr Ala Ala Leu Ala Ala Thr Ser Leu
1               5                   10                  15

Ala Ala Pro Leu Leu Glu Glu Arg Gln Ser Cys Ser Ser Val Trp Gly
            20                  25                  30

Gln Cys Gly Gly Ile Asn Tyr Asn Gly Pro Thr Cys Cys Gln Ser Gly
        35                  40                  45

Ser Val Cys Thr Tyr Leu Asn Asp Trp Tyr Ser Gln Cys Ile Pro Gly
    50                  55                  60

Gln Ala Gln Pro Gly Thr Thr Ser Thr Thr Ala Arg Thr Thr Ser Thr
65                  70                  75                  80

Ser Thr Thr Ser Thr Ser Ser Val Arg Pro Thr Thr Ser Asn Thr Pro
                85                  90                  95

Val Thr Thr Ala Pro Pro Thr Thr Thr Ile Pro Gly Gly Ala Ser Ser
            100                 105                 110

Thr Ala Ser Tyr Asn Gly Asn Pro Phe Ser Gly Val Gln Leu Trp Ala
        115                 120                 125

Asn Thr Tyr Tyr Ser Ser Glu Val His Thr Leu Ala Ile Pro Ser Leu
    130                 135                 140

Ser Pro Glu Leu Ala Ala Lys Ala Ala Lys Val Ala Glu Val Pro Ser
145                 150                 155                 160

Phe Gln Trp Leu Asp Arg Asn Val Thr Val Asp Thr Leu Phe Ser Gly
                165                 170                 175

Thr Leu Ala Glu Ile Arg Ala Ala Asn Gln Arg Gly Ala Asn Pro Pro
            180                 185                 190

Tyr Ala Gly Ile Phe Val Val Tyr Asp Leu Pro Asp Arg Asp Cys Ala
        195                 200                 205

Ala Ala Ala Ser Asn Gly Glu Trp Ser Ile Ala Asn Asn Gly Ala Asn
    210                 215                 220

Asn Tyr Lys Arg Tyr Ile Asp Arg Ile Arg Glu Leu Leu Ile Gln Tyr
225                 230                 235                 240

Ser Asp Ile Arg Thr Ile Leu Val Ile Glu Pro Asp Ser Leu Ala Asn
                245                 250                 255

Met Val Thr Asn Met Asn Val Gln Lys Cys Ser Asn Ala Ala Ser Thr
            260                 265                 270

Tyr Lys Glu Leu Thr Val Tyr Ala Leu Lys Gln Leu Asn Leu Pro His
        275                 280                 285

Val Ala Met Tyr Met Asp Ala Gly His Ala Gly Trp Leu Gly Trp Pro
```

```
                    290                 295                 300

Ala Asn Ile Gln Pro Ala Ala Glu Leu Phe Ala Gln Ile Tyr Arg Asp
305                 310                 315                 320

Ala Gly Arg Pro Ala Val Arg Gly Leu Ala Thr Asn Val Ala Asn
                325                 330                 335

Tyr Asn Ala Trp Ser Ile Ala Ser Pro Ser Tyr Thr Ser Pro Asn
                340                 345                 350

Pro Asn Tyr Asp Glu Lys His Tyr Ile Glu Ala Phe Ala Pro Leu Leu
            355                 360                 365

Arg Asn Gln Gly Phe Asp Ala Lys Phe Ile Val Asp Thr Gly Arg Asn
        370                 375                 380

Gly Lys Gln Pro Thr Gly Gln Leu Glu Trp Gly His Trp Cys Asn Val
385                 390                 395                 400

Lys Gly Thr Gly Phe Gly Val Arg Pro Thr Ala Asn Thr Gly His Glu
                405                 410                 415

Leu Val Asp Ala Phe Val Trp Val Lys Pro Gly Gly Glu Ser Asp Gly
                420                 425                 430

Thr Ser Ala Asp Thr Ser Ala Ala Arg Tyr Asp Tyr His Cys Gly Leu
            435                 440                 445

Ser Asp Ala Leu Thr Pro Ala Pro Glu Ala Gly Gln Trp Phe Gln Ala
        450                 455                 460

Tyr Phe Glu Gln Leu Leu Ile Asn Ala Asn Pro Pro Leu
465                 470                 475

<210> SEQ ID NO 57
<211> LENGTH: 2586
<212> TYPE: DNA
<213> ORGANISM: Aspergillus oryzae

<400> SEQUENCE: 57
atgaagcttg gttggatcga ggtggccgca ttggcggctg cctcagtagt cagtgccaag     60
gatgatctcg cgtactcccc tcctttctac ccttccccat gggcagatgg tcagggtgaa    120
tgggcggaag tatacaaacg cgctgtagac atagtttccc agatgacgtt gacagagaaa    180
gtcaacttaa cgactggaac aggatggcaa ctagagaggg tgttggaca aactggcagt     240
gttcccagac tcaacatccc cagcttgtgt ttgcaggata gtcctcttgg tattcgtttc    300
tcggactaca attcagcttt ccctgcgggt gttaatgtcg ctgccacctg ggacaagacg    360
ctcgcctacc ttcgtggtca ggcaatgggt gaggagttca gtgataaggg tattgacgtt    420
cagctgggtc ctgctgctgg ccctctcggt gctcatccgg atggcggtag aaactgggaa    480
ggtttctcac cagatccagc cctcaccggt gtacttttttg cggagacgat taagggtatt    540
caagatgctg tgtcattgc gacagctaag cattatatca tgaacgaaca agagcatttc    600
cgccaacaac ccgaggctgc gggttacgga ttcaacgtaa gcgacagttt gagttccaac    660
gttgatgaca agactatgca tgaattgtac ctctggccct tcgcggatgc agtacgcgct    720
ggagtcggtg ctgtcatgtg ctcttacaac caaatcaaca acagctacgg ttgcgagaat    780
agcgaaactc tgaacaagct tttgaaggcg gagcttggtt tccaaggctt cgtcatgagt    840
gattggaccg ctcatcacag cggcgtaggc gctgctttag caggtctgga tatgtcgatg    900
cccgtgatg ttaccttcga tagtggtacg tcttttctggg gtgcaaactt gacggtcgt     960
gtccttaacg gtacaatccc ccaatggcgt gttgatgaca tggctgtccg tatcatggcc   1020
gcttattaca aggttggccg cgacaccaaa tacaccctc ccaacttcag ctcgtggacc   1080
```

```
aggacgaat atggtttcgc gcataaccat gtttcggaag gtgcttacga gagggtcaac    1140
gaattcgtgg acgtgcaacg cgatcatgcc gacctaatcc gtcgcatcgg cgcgcagagc    1200
actgttctgc tgaagaacaa gggtgccttg cccttgagcc gcaaggaaaa gctggtcgcc    1260
cttctgggag aggatgcggg ttccaactcg tgggcgcta acggctgtga tgaccgtggt     1320
tgcgataacg gtaccttgc catggcctgg ggtagcggta ctgcgaattt cccatacctc     1380
gtgacaccag agcaggcgat tcagaacgaa gttcttcagg gccgtggtaa tgtcttcgcc    1440
gtgaccgaca gttgggcgct cgacaagatc gctgcggctg cccgccaggc cagcgtatct    1500
ctcgtgttcg tcaactccga ctcaggagaa ggctatctta gtgtggatgg aaatgagggc    1560
gatcgtaaca acatcactct gtggaagaac ggcgacaatg tggtcaagac cgcagcgaat    1620
aactgtaaca acaccgttgt catcatccac tccgtcggac cagttttgat cgatgaatgg    1680
tatgaccacc ccaatgtcac tggtattctc tgggctggtc tgccaggcca ggagtctggt    1740
aactccattg ccgatgtgct gtacggtcgt gtcaaccctg gcgccaagtc tcctttcact    1800
tggggcaaga cccgggagtc gtatggttct cccttggtca aggatgccaa caatggcaac    1860
ggagcgcccc agtctgattt cacccagggt gttttcatcg attaccgcca tttcgataag    1920
ttcaatgaga cccctatcta cgagtttggc tacggcttga gctacaccac cttcgagctc    1980
tccgacctcc atgttcagcc cctgaacgcg tcccgataca ctcccaccag tggcatgact    2040
gaagctgcaa gaactttggg tgaaattggc gatgcgtcgg agtacgtgta ccggaggggg    2100
ctggaaagga tccatgagtt tatctatccc tggatcaact ctaccgacct gaaggcatcg    2160
tctgacgatt ctaactacgg ctgggaagac tccaagtata ttcccgaagg cgccacggat    2220
gggtctgccc agccccgttt gcccgctagt ggtggtgccg aggaaaaccc cggtctgtac    2280
gaggatcttt tccgcgtctc tgtgaaggtc aagaacacgg gcaatgtcgc cggtgatgaa    2340
gttcctcagc tgtacgtttc cctaggcggc ccgaatgagc ccaaggtggt actgcgcaag    2400
tttgagcgta ttcacttggc cccttcgcag gaggccgtgt ggacaacgac ccttacccgt    2460
cgtgaccttg caaactggga cgtttcggct caggactgga ccgtcactcc ttaccccaag    2520
acgatctacg ttggaaactc ctcacggaaa ctgccgctcc aggcctcgct gcctaaggcc    2580
cagtaa                                                                2586
```

```
<210> SEQ ID NO 58
<211> LENGTH: 861
<212> TYPE: PRT
<213> ORGANISM: Aspergillus oryzae

<400> SEQUENCE: 58

Met Lys Leu Gly Trp Ile Glu Val Ala Ala Leu Ala Ala Ala Ser Val
1               5                   10                  15

Val Ser Ala Lys Asp Asp Leu Ala Tyr Ser Pro Pro Phe Tyr Pro Ser
            20                  25                  30

Pro Trp Ala Asp Gly Gln Gly Glu Trp Ala Glu Val Tyr Lys Arg Ala
        35                  40                  45

Val Asp Ile Val Ser Gln Met Thr Leu Thr Glu Lys Val Asn Leu Thr
    50                  55                  60

Thr Gly Thr Gly Trp Gln Leu Glu Arg Cys Val Gly Gln Thr Gly Ser
65                  70                  75                  80

Val Pro Arg Leu Asn Ile Pro Ser Leu Cys Leu Gln Asp Ser Pro Leu
                85                  90                  95

Gly Ile Arg Phe Ser Asp Tyr Asn Ser Ala Phe Pro Ala Gly Val Asn
```

```
            100                 105                 110
Val Ala Ala Thr Trp Asp Lys Thr Leu Ala Tyr Leu Arg Gly Gln Ala
            115                 120                 125
Met Gly Glu Glu Phe Ser Asp Lys Gly Ile Asp Val Gln Leu Gly Pro
            130                 135             140
Ala Ala Gly Pro Leu Gly Ala His Pro Asp Gly Arg Asn Trp Glu
145                 150                 155                 160
Gly Phe Ser Pro Asp Pro Ala Leu Thr Gly Val Leu Phe Ala Glu Thr
                    165                 170                 175
Ile Lys Gly Ile Gln Asp Ala Gly Val Ile Ala Thr Ala Lys His Tyr
                180                 185                 190
Ile Met Asn Glu Gln Glu His Phe Arg Gln Gln Pro Glu Ala Ala Gly
            195                 200                 205
Tyr Gly Phe Asn Val Ser Asp Ser Leu Ser Ser Asn Val Asp Asp Lys
        210                 215                 220
Thr Met His Glu Leu Tyr Leu Trp Pro Phe Ala Asp Ala Val Arg Ala
225                 230                 235                 240
Gly Val Gly Ala Val Met Cys Ser Tyr Asn Gln Ile Asn Asn Ser Tyr
                    245                 250                 255
Gly Cys Glu Asn Ser Glu Thr Leu Asn Lys Leu Leu Lys Ala Glu Leu
                260                 265                 270
Gly Phe Gln Gly Phe Val Met Ser Asp Trp Thr Ala His His Ser Gly
            275                 280                 285
Val Gly Ala Ala Leu Ala Gly Leu Asp Met Ser Met Pro Gly Asp Val
        290                 295                 300
Thr Phe Asp Ser Gly Thr Ser Phe Trp Gly Ala Asn Leu Thr Val Gly
305                 310                 315                 320
Val Leu Asn Gly Thr Ile Pro Gln Trp Arg Val Asp Asp Met Ala Val
                    325                 330                 335
Arg Ile Met Ala Ala Tyr Tyr Lys Val Gly Arg Asp Thr Lys Tyr Thr
                340                 345                 350
Pro Pro Asn Phe Ser Ser Trp Thr Arg Asp Glu Tyr Gly Phe Ala His
            355                 360                 365
Asn His Val Ser Glu Gly Ala Tyr Glu Arg Val Asn Glu Phe Val Asp
        370                 375                 380
Val Gln Arg Asp His Ala Asp Leu Ile Arg Arg Ile Gly Ala Gln Ser
385                 390                 395                 400
Thr Val Leu Leu Lys Asn Lys Gly Ala Leu Pro Leu Ser Arg Lys Glu
                    405                 410                 415
Lys Leu Val Ala Leu Leu Gly Glu Asp Ala Gly Ser Asn Ser Trp Gly
                420                 425                 430
Ala Asn Gly Cys Asp Asp Arg Gly Cys Asp Asn Gly Thr Leu Ala Met
            435                 440                 445
Ala Trp Gly Ser Gly Thr Ala Asn Phe Pro Tyr Leu Val Thr Pro Glu
        450                 455                 460
Gln Ala Ile Gln Asn Glu Val Leu Gln Gly Arg Gly Asn Val Phe Ala
465                 470                 475                 480
Val Thr Asp Ser Trp Ala Leu Asp Lys Ile Ala Ala Ala Arg Gln
                    485                 490                 495
Ala Ser Val Ser Leu Val Phe Val Asn Ser Asp Ser Gly Glu Gly Tyr
            500                 505                 510
Leu Ser Val Asp Gly Asn Glu Gly Asp Arg Asn Asn Ile Thr Leu Trp
            515                 520                 525
```

Lys Asn Gly Asp Asn Val Val Lys Thr Ala Ala Asn Cys Asn Asn
530                 535                 540

Thr Val Val Ile Ile His Ser Val Gly Pro Val Leu Ile Asp Glu Trp
545                 550                 555                 560

Tyr Asp His Pro Asn Val Thr Gly Ile Leu Trp Ala Gly Leu Pro Gly
            565                 570                 575

Gln Glu Ser Gly Asn Ser Ile Ala Asp Val Leu Tyr Gly Arg Val Asn
        580                 585                 590

Pro Gly Ala Lys Ser Pro Phe Thr Trp Gly Lys Thr Arg Glu Ser Tyr
    595                 600                 605

Gly Ser Pro Leu Val Lys Asp Ala Asn Asn Gly Asn Gly Ala Pro Gln
610                 615                 620

Ser Asp Phe Thr Gln Gly Val Phe Ile Asp Tyr Arg His Phe Asp Lys
625                 630                 635                 640

Phe Asn Glu Thr Pro Ile Tyr Glu Phe Gly Tyr Gly Leu Ser Tyr Thr
            645                 650                 655

Thr Phe Glu Leu Ser Asp Leu His Val Gln Pro Leu Asn Ala Ser Arg
        660                 665                 670

Tyr Thr Pro Thr Ser Gly Met Thr Glu Ala Ala Lys Asn Phe Gly Glu
    675                 680                 685

Ile Gly Asp Ala Ser Glu Tyr Val Tyr Pro Glu Gly Leu Glu Arg Ile
690                 695                 700

His Glu Phe Ile Tyr Pro Trp Ile Asn Ser Thr Asp Leu Lys Ala Ser
705                 710                 715                 720

Ser Asp Asp Ser Asn Tyr Gly Trp Glu Asp Ser Lys Tyr Ile Pro Glu
            725                 730                 735

Gly Ala Thr Asp Gly Ser Ala Gln Pro Arg Leu Pro Ala Ser Gly Gly
        740                 745                 750

Ala Gly Gly Asn Pro Gly Leu Tyr Glu Asp Leu Phe Arg Val Ser Val
    755                 760                 765

Lys Val Lys Asn Thr Gly Asn Val Ala Gly Asp Glu Val Pro Gln Leu
770                 775                 780

Tyr Val Ser Leu Gly Gly Pro Asn Glu Pro Lys Val Val Leu Arg Lys
785                 790                 795                 800

Phe Glu Arg Ile His Leu Ala Pro Ser Gln Glu Ala Val Trp Thr Thr
            805                 810                 815

Thr Leu Thr Arg Arg Asp Leu Ala Asn Trp Asp Val Ser Ala Gln Asp
        820                 825                 830

Trp Thr Val Thr Pro Tyr Pro Lys Thr Ile Tyr Val Gly Asn Ser Ser
    835                 840                 845

Arg Lys Leu Pro Leu Gln Ala Ser Leu Pro Lys Ala Gln
850                 855                 860

<210> SEQ ID NO 59
<211> LENGTH: 3060
<212> TYPE: DNA
<213> ORGANISM: Aspergillus fumigatus

<400> SEQUENCE: 59
atgagattcg gttggctcga ggtggccgct ctgacggccg cttctgtagc caatgcccag     60
gtttgtgatg ctttcccgtc attgtttcgg atatagttga caatagtcat ggaaataatc    120
aggaattggc tttctctcca ccattctacc cttcgccttg ggctgatggc cagggagagt    180
gggcagatgc ccatcgacgc gccgtcgaga tcgtttctca gatgacactg gcggagaagg    240

```
ttaaccttac aacgggtact gggtgggttg cgactttttt gttgacagtg agctttcttc    300
actgaccatc tacacagatg ggaaatggac cgatgcgtcg gtcaaaccgg cagcgttccc    360
aggtaagctt gcaattctgc aacaacgtgc aagtgtagtt gctaaaacgc ggtggtgcag    420
acttggtatc aactggggtc tttgtggcca ggattcccct ttgggtatcc gtttctgtga    480
gctatacccg cggagtcttt cagtccttgt attatgtgct gatgattgtc tctgtatagc    540
tgacctcaac tccgccttcc ctgctggtac taatgtcgcc gcgacatggg acaagacact    600
cgcctacctt cgtggcaagg ccatgggtga ggaattcaac gacaagggcg tggacatttt    660 gctgggcct gctgctggtc ctctcggcaa atacccggac ggcggcagaa tctgggaagg    720
cttctctcct gatccggttc tcactggtgt acttttcgcc gaaactatca agggtatcca    780
agacgcgggt gtgattgcta ctgccaagca ttacattctg aatgaacagg agcatttccg    840
acaggttggc gaggcccagg atatggttta acatcacg gagacgatca gctccaacgt    900
ggatgacaag accatgcacg agttgtacct ttggtgagta gttgacactg caaatgagga    960
ccttgattga tttgactgac ctggaatgca ggcccttttgc agatgctgtg cgcggtaaga   1020
ttttccgtag acttgacctc gcgacgaaga aatcgctgac gaaccatcgt agctggcgtt   1080
ggcgctgtca tgtgttccta caatcaaatc aacaacagct acggttgtca aaacagtcaa   1140
actctcaaca agctcctcaa ggctgagctg gcttccaag gcttcgtcat gagtgactgg   1200
agcgctcacc acagcggtgt cggcgctgcc ctcgctgggt tggatatgtc gatgcctgga   1260
gacatttcct tcgacgacgg actctccttc tggggcacga acctaactgt cagtgttctt   1320
aacggcaccg ttccagcctg gcgtgtcgat gacatggctg ttcgtatcat gaccgcgtac   1380
tacaaggttg gtcgtgaccg tcttcgtatt cccctaact tcagctcctg gacccgggat   1440
gagtacggct gggagcattc tgctgtctcc gagggagcct ggaccaaggt gaacgacttc   1500
gtcaatgtgc agcgcagtca ctctcagatc atccgtgaga ttggtgccgc tagtacagtg   1560
ctcttgaaga acacgggtgc tcttcctttg accggcaagg aggttaaagt gggtgttctc   1620
ggtgaagacg ctggttccaa cccgtggggt gctaacggct gccccgaccg cggctgtgat   1680
aacggcactc ttgctatggc ctggggtagt ggtactgcca acttcccta ccttgtcacc   1740 cccgagcagg ctatccagcg agaggtcatc agcaacggcg gcaatgtctt tgctgtgact   1800
gataacgggg ctctcagcca gatggcagat gttgcatctc aatccaggtg agtgcgggct   1860
cttagaaaaa gaacgttctc tgaatgaagt ttttaacca ttgcgaacag cgtgtctttg   1920
gtgtttgtca acgccgactc tggagagggt ttcatcagtg tcgacggcaa cgagggtgac   1980
cgcaaaaatc tcactctgtg gaagaacggc gaggccgtca ttgacactgt tgtcagccac   2040
tgcaacaaca cgattgtggt tattcacagt gttgggcccg tcttgatcga ccggtggtat   2100
gataacccca acgtcactgc catcatctgg gccggcttgc ccggtcagga gagtggcaac   2160
tccctggtcg acgtgctcta tggccgcgtc aaccccagcg ccaagacccc gttcacctgg   2220
ggcaagactc gggagtctta cggggctccc ttgctcaccg agcctaacaa tggcaatggt   2280
gctccccagg atgatttcaa cgagggcgtc ttcattgact accgtcactt tgacaagcgc   2340
aatgagaccc ccatttatga gtttggccat ggcttgagct acaccacctt tggttactct   2400
caccttcggg ttcaggccct caatagttcg agttcggcat atgtcccgac tagcggagag   2460
accaagcctg cgccaaccta tgtgagatc ggtagtgccg ccgactacct gtatcccgag   2520
ggtctcaaaa gaattaccaa gtttatttac ccttggctca actcgaccga cctcgaggat   2580
```

-continued

```
tcttctgacg acccgaacta cggctgggag gactcggagt acattcccga aggcgctagg    2640
gatgggtctc ctcaaccccct cctgaaggct ggcggcgctc ctggtggtaa ccctaccctt    2700
tatcaggatc ttgttagggt gtcggccacc ataaccaaca ctggtaacgt cgccggttat    2760
gaagtccctc aattggtgag tgacccgcat gttccttgcg ttgcaatttg gctaactcgc    2820
ttctagtatg tttcactggg cggaccgaac gagcctcggg tcgttctgcg caagttcgac    2880
cgaatcttcc tggctcctgg ggagcaaaag gtttggacca cgactcttaa ccgtcgtgat    2940
ctcgccaatt gggatgtgga ggctcaggac tgggtcatca aaagtaccc caagaaagtg    3000 cacgtcggca gctcctcgcg taagctgcct ctgagagcgc ctctgccccg tgtctactag    3060
```

<210> SEQ ID NO 60
<211> LENGTH: 863
<212> TYPE: PRT
<213> ORGANISM: Aspergillus fumigatus

<400> SEQUENCE: 60

```
Met Arg Phe Gly Trp Leu Glu Val Ala Ala Leu Thr Ala Ala Ser Val
  1               5                  10                  15

Ala Asn Ala Gln Glu Leu Ala Phe Ser Pro Pro Phe Tyr Pro Ser Pro
             20                  25                  30

Trp Ala Asp Gly Gln Gly Glu Trp Ala Asp Ala His Arg Arg Ala Val
         35                  40                  45

Glu Ile Val Ser Gln Met Thr Leu Ala Glu Lys Val Asn Leu Thr Thr
     50                  55                  60

Gly Thr Gly Trp Glu Met Asp Arg Cys Val Gly Gln Thr Gly Ser Val
 65                  70                  75                  80

Pro Arg Leu Gly Ile Asn Trp Gly Leu Cys Gly Gln Asp Ser Pro Leu
                 85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
    130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Leu Asn Glu Gln Glu His Phe Arg Gln Val Gly Glu Ala Gln Gly
        195                 200                 205

Tyr Gly Tyr Asn Ile Thr Glu Thr Ile Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
            260                 265                 270

Gly Phe Gln Gly Phe Val Met Ser Asp Trp Ser Ala His His Ser Gly
        275                 280                 285

Val Gly Ala Ala Leu Ala Gly Leu Asp Met Ser Met Pro Gly Asp Ile
```

```
                290                 295                 300
Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
                340                 345                 350

Pro Pro Asn Phe Ser Ser Trp Thr Arg Asp Glu Tyr Gly Trp Glu His
                355                 360                 365

Ser Ala Val Ser Glu Gly Ala Trp Thr Lys Val Asn Asp Phe Val Asn
                370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
                420                 425                 430

Ala Asn Gly Cys Pro Asp Arg Gly Cys Asp Asn Gly Thr Leu Ala Met
                435                 440                 445

Ala Trp Gly Ser Gly Thr Ala Asn Phe Pro Tyr Leu Val Thr Pro Glu
                450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
                485                 490                 495

Ser Ser Val Ser Leu Val Phe Val Asn Ala Asp Ser Gly Glu Gly Phe
                500                 505                 510

Ile Ser Val Asp Gly Asn Glu Gly Asp Arg Lys Asn Leu Thr Leu Trp
                515                 520                 525

Lys Asn Gly Glu Ala Val Ile Asp Thr Val Val Ser His Cys Asn Asn
530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
                580                 585                 590

Pro Ser Ala Lys Thr Pro Phe Thr Trp Gly Lys Thr Arg Glu Ser Tyr
                595                 600                 605

Gly Ala Pro Leu Leu Thr Glu Pro Asn Asn Gly Asn Gly Ala Pro Gln
                610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
                660                 665                 670

Ser Ala Tyr Val Pro Thr Ser Gly Glu Thr Lys Pro Ala Pro Thr Tyr
                675                 680                 685

Gly Glu Ile Gly Ser Ala Ala Asp Tyr Leu Tyr Pro Glu Gly Leu Lys
                690                 695                 700

Arg Ile Thr Lys Phe Ile Tyr Pro Trp Leu Asn Ser Thr Asp Leu Glu
705                 710                 715                 720
```

```
Asp Ser Ser Asp Asp Pro Asn Tyr Gly Trp Glu Asp Ser Glu Tyr Ile
            725                 730                 735
Pro Glu Gly Ala Arg Asp Gly Ser Pro Gln Pro Leu Leu Lys Ala Gly
        740                 745                 750
Gly Ala Pro Gly Gly Asn Pro Thr Leu Tyr Gln Asp Leu Val Arg Val
        755                 760                 765
Ser Ala Thr Ile Thr Asn Thr Gly Asn Val Ala Gly Tyr Glu Val Pro
    770                 775                 780
Gln Leu Tyr Val Ser Leu Gly Gly Pro Asn Glu Pro Arg Val Val Leu
785                 790                 795                 800
Arg Lys Phe Asp Arg Ile Phe Leu Ala Pro Gly Glu Gln Lys Val Trp
            805                 810                 815
Thr Thr Thr Leu Asn Arg Arg Asp Leu Ala Asn Trp Asp Val Glu Ala
            820                 825                 830
Gln Asp Trp Val Ile Thr Lys Tyr Pro Lys Lys Val His Val Gly Ser
            835                 840                 845
Ser Ser Arg Lys Leu Pro Leu Arg Ala Pro Leu Pro Arg Val Tyr
        850                 855                 860

<210> SEQ ID NO 61
<211> LENGTH: 2800
<212> TYPE: DNA
<213> ORGANISM: Penicillium brasilianum

<400> SEQUENCE: 61
tgaaaatgca gggttctaca atctttctgg ctttcgcctc atgggcgagc caggttgctg      60
ccattgcgca gcccatacag aagcacgagg tttgttttat cttgctcatg acgtgctttt     120
gacttgacta attgttttac atacagcccg gatttctgca cgggcccaa gccatagaat      180
cgttctcaga accgttctac ccgtcgccct ggatgaatcc tcacgccgag ggctgggagg     240
ccgcatatca gaaagctcaa gattttgtct cgcaactcac tatcttggag aaaataaatc     300
tgaccaccgg tgttgggtaa gtctctccga ctgcttctgg gtcacggtgc gacgagccac     360
tgacttttg aagctgggaa atgggccgt gtgtaggaaa cactggatca attcctcgtc      420
tcggattcaa aggattttgt acccaggatt caccacaggg tgttcggttc gcagattatt     480
cctccgcttt cacatctagc caaatggccg ccgcaacatt tgaccgctca attctttatc     540
aacgaggcca agccatggca caggaacaca aggctaaggg tatcacaatt caattgggcc     600
ctgttgccgg ccctctcggt cgcatccccg agggcggccg caactgggaa ggattctccc     660
ctgatcctgt cttgactggt atagccatgg ctgagacaat aagggcatg caggatactg      720
gagtgattgc ttgcgctaaa cattatattg gaaacgagca ggagcacttc cgtcaagtgg     780
gtgaagctgc gggtcacgga tacactattt ccgatactat ttcatctaat attgacgacc     840
gtgctatgca tgagctatac ttgtggccat ttgctgatgc cgttcgcgct ggtgtgggtt     900
ctttcatgtg ctcatactct cagatcaaca actcctacgg atgccaaaac agtcagaccc     960
tcaacaagct cctcaagagc gaattgggct tccaaggctt tgtcatgagc gattggggtg    1020
cccatcactc tggagtgtca tcggcgctag ctggacttga tatgagcatg ccgggtgata    1080
ccgaatttga ttctggcttg agcttctggg gctctaacct caccattgca attctgaacg    1140
gcacggttcc cgaatggcgc ctggatgaca tggcgatgcg aattatggct gcatacttca    1200
aagttggcct tactattgag gatcaaccag atgtcaactt caatgcctgg acccatgaca    1260
cctacggata taaatacgct tatagcaagg aagattacga gcaggtcaac tggcatgtcg    1320
```

-continued

```
atgttcgcag cgaccacaat aagctcattc gcgagactgc cgcgaagggt acagttctgc    1380
tgaagaacaa ctttcatgct ctccctctga agcagcccag gttcgtggcc gtcgttggtc    1440
aggatgccgg gccaaacccc aagggcccta acggctgcgc agaccgagga tgcgaccaag    1500
gcactctcgc aatgggatgg ggctcagggt ctaccgaatt cccttacctg gtcactcctg    1560
acactgctat tcagtcaaag gtcctcgaat acggggtcg atacgagagt attttgata     1620
actatgacga caatgctatc ttgtcgcttg tctcacagcc tgatgcaacc tgtatcgttt    1680
ttgcaaatgc cgattccggt gaaggctaca tcactgtcga caacaactgg ggtgaccgca    1740
acaatctgac cctctggcaa aatgccgatc aagtgattag cactgtcagc tcgcgatgca    1800
acaacacaat cgttgttctc cactctgtcg accagtgtt gctaaatggt atatatgagc    1860
acccgaacat cacagctatt gtctgggcag ggatgccagg cgaagaatct ggcaatgctc    1920
tcgtggatat tctttggggc aatgttaacc ctgccggtcg cactccgttc acctgggcca    1980
aaagtcgaga ggactatggc actgatataa tgtacgagcc caacaacggc cagcgtgcgc    2040
ctcagcagga tttcaccgag agcatctacc tcgactaccg ccatttcgac aaagctggta    2100
tcgagccaat ttacgagttt ggattcggcc tctcctatac caccttcgaa tactctgacc    2160
tccgtgttgt gaagaagtat gttcaaccat acagtcccac gaccggcacc ggtgctcaag    2220
caccttccat cggacagcca cctagccaga acctggatac ctacaagttc cctgctacat    2280
acaagtacat caaaaccttc atttatccct acctgaacag cactgtctcc ctccgcgctg    2340
cttccaagga tcccgaatac ggtcgtacag actttatccc accccacgcg cgtgatggct    2400
cccctcaacc tctcaacccc gctggagacc cagtggccag tggtggaaac aacatgctct    2460
acgacgaact ttacgaggtc actgcacaga tcaaaaacac tggcgacgtg ccggcgacg    2520
aagtcgtcca gctttacgta gatctcgggg gtgacaaccc gcctcgtcag ttgagaaact    2580
ttgacaggtt ttatctgctg cccggtcaga gctcaacatt ccgggctaca ttgacgcgcc    2640
gtgatttgag caactgggat attgaggcgc agaactggcg agttacggaa tcgcctaaga    2700
gagtgtatgt tggacggtcg agtcgggatt tgccgctgag ctcacaattg gagtaatgat    2760
catgtctacc aatagatgtt gaatgtctgg tgtggatatt                         2800
```

<210> SEQ ID NO 62
<211> LENGTH: 878
<212> TYPE: PRT
<213> ORGANISM: Penicillium brasilianum

<400> SEQUENCE: 62

```
Met Gln Gly Ser Thr Ile Phe Leu Ala Phe Ala Ser Trp Ala Ser Gln
1               5                   10                  15

Val Ala Ala Ile Ala Gln Pro Ile Gln Lys His Glu Pro Gly Phe Leu
            20                  25                  30

His Gly Pro Gln Ala Ile Glu Ser Phe Ser Glu Pro Phe Tyr Pro Ser
        35                  40                  45

Pro Trp Met Asn Pro His Ala Glu Gly Trp Glu Ala Ala Tyr Gln Lys
    50                  55                  60

Ala Gln Asp Phe Val Ser Gln Leu Thr Ile Leu Glu Lys Ile Asn Leu
65                  70                  75                  80

Thr Thr Gly Val Gly Trp Glu Asn Gly Pro Cys Val Gly Asn Thr Gly
                85                  90                  95

Ser Ile Pro Arg Leu Gly Phe Lys Gly Phe Cys Thr Gln Asp Ser Pro
            100                 105                 110
```

```
Gln Gly Val Arg Phe Ala Asp Tyr Ser Ser Ala Phe Thr Ser Ser Gln
            115                 120                 125
Met Ala Ala Ala Thr Phe Asp Arg Ser Ile Leu Tyr Gln Arg Gly Gln
130                 135                 140
Ala Met Ala Gln Glu His Lys Ala Lys Gly Ile Thr Ile Gln Leu Gly
145                 150                 155                 160
Pro Val Ala Gly Pro Leu Gly Arg Ile Pro Glu Gly Gly Arg Asn Trp
            165                 170                 175
Glu Gly Phe Ser Pro Asp Pro Val Leu Thr Gly Ile Ala Met Ala Glu
            180                 185                 190
Thr Ile Lys Gly Met Gln Asp Thr Gly Val Ile Ala Cys Ala Lys His
            195                 200                 205
Tyr Ile Gly Asn Glu Gln Glu His Phe Arg Gln Val Gly Glu Ala Ala
            210                 215                 220
Gly His Gly Tyr Thr Ile Ser Asp Thr Ile Ser Ser Asn Ile Asp Asp
225                 230                 235                 240
Arg Ala Met His Glu Leu Tyr Leu Trp Pro Phe Ala Asp Ala Val Arg
                245                 250                 255
Ala Gly Val Gly Ser Phe Met Cys Ser Tyr Ser Gln Ile Asn Asn Ser
            260                 265                 270
Tyr Gly Cys Gln Asn Ser Gln Thr Leu Asn Lys Leu Leu Lys Ser Glu
            275                 280                 285
Leu Gly Phe Gln Gly Phe Val Met Ser Asp Trp Gly Ala His His Ser
            290                 295                 300
Gly Val Ser Ser Ala Leu Ala Gly Leu Asp Met Ser Met Pro Gly Asp
305                 310                 315                 320
Thr Glu Phe Asp Ser Gly Leu Ser Phe Trp Gly Ser Asn Leu Thr Ile
                325                 330                 335
Ala Ile Leu Asn Gly Thr Val Pro Glu Trp Arg Leu Asp Asp Met Ala
            340                 345                 350
Met Arg Ile Met Ala Ala Tyr Phe Lys Val Gly Leu Thr Ile Glu Asp
            355                 360                 365
Gln Pro Asp Val Asn Phe Asn Ala Trp Thr His Asp Thr Tyr Gly Tyr
            370                 375                 380
Lys Tyr Ala Tyr Ser Lys Glu Asp Tyr Glu Gln Val Asn Trp His Val
385                 390                 395                 400
Asp Val Arg Ser Asp His Asn Lys Leu Ile Arg Glu Thr Ala Ala Lys
                405                 410                 415
Gly Thr Val Leu Leu Lys Asn Asn Phe His Ala Leu Pro Leu Lys Gln
            420                 425                 430
Pro Arg Phe Val Ala Val Gly Gln Asp Ala Gly Pro Asn Pro Lys
            435                 440                 445
Gly Pro Asn Gly Cys Ala Asp Arg Gly Cys Asp Gln Gly Thr Leu Ala
450                 455                 460
Met Gly Trp Gly Ser Gly Ser Thr Glu Phe Pro Tyr Leu Val Thr Pro
465                 470                 475                 480
Asp Thr Ala Ile Gln Ser Lys Val Leu Glu Tyr Gly Gly Arg Tyr Glu
                485                 490                 495
Ser Ile Phe Asp Asn Tyr Asp Asp Asn Ala Ile Leu Ser Leu Val Ser
            500                 505                 510
Gln Pro Asp Ala Thr Cys Ile Val Phe Ala Asn Ala Asp Ser Gly Glu
            515                 520                 525
```

Gly Tyr Ile Thr Val Asp Asn Asn Trp Gly Asp Arg Asn Asn Leu Thr
    530                 535                 540
Leu Trp Gln Asn Ala Asp Gln Val Ile Ser Thr Val Ser Ser Arg Cys
545                 550                 555                 560
Asn Asn Thr Ile Val Val Leu His Ser Val Gly Pro Val Leu Leu Asn
                565                 570                 575
Gly Ile Tyr Glu His Pro Asn Ile Thr Ala Ile Val Trp Ala Gly Met
            580                 585                 590
Pro Gly Glu Glu Ser Gly Asn Ala Leu Val Asp Ile Leu Trp Gly Asn
        595                 600                 605
Val Asn Pro Ala Gly Arg Thr Pro Phe Thr Trp Ala Lys Ser Arg Glu
610                 615                 620
Asp Tyr Gly Thr Asp Ile Met Tyr Glu Pro Asn Asn Gly Gln Arg Ala
625                 630                 635                 640
Pro Gln Gln Asp Phe Thr Glu Ser Ile Tyr Leu Asp Tyr Arg His Phe
                645                 650                 655
Asp Lys Ala Gly Ile Glu Pro Ile Tyr Glu Phe Gly Phe Gly Leu Ser
            660                 665                 670
Tyr Thr Thr Phe Glu Tyr Ser Asp Leu Arg Val Val Lys Lys Tyr Val
        675                 680                 685
Gln Pro Tyr Ser Pro Thr Thr Gly Thr Gly Ala Gln Ala Pro Ser Ile
690                 695                 700
Gly Gln Pro Pro Ser Gln Asn Leu Asp Thr Tyr Lys Phe Pro Ala Thr
705                 710                 715                 720
Tyr Lys Tyr Ile Lys Thr Phe Ile Tyr Pro Tyr Leu Asn Ser Thr Val
                725                 730                 735
Ser Leu Arg Ala Ala Ser Lys Asp Pro Glu Tyr Gly Arg Thr Asp Phe
            740                 745                 750
Ile Pro Pro His Ala Arg Asp Gly Ser Pro Gln Pro Leu Asn Pro Ala
        755                 760                 765
Gly Asp Pro Val Ala Ser Gly Gly Asn Asn Met Leu Tyr Asp Glu Leu
770                 775                 780
Tyr Glu Val Thr Ala Gln Ile Lys Asn Thr Gly Asp Val Ala Gly Asp
785                 790                 795                 800
Glu Val Val Gln Leu Tyr Val Asp Leu Gly Gly Asp Asn Pro Pro Arg
                805                 810                 815
Gln Leu Arg Asn Phe Asp Arg Phe Tyr Leu Leu Pro Gly Gln Ser Ser
            820                 825                 830
Thr Phe Arg Ala Thr Leu Thr Arg Arg Asp Leu Ser Asn Trp Asp Ile
        835                 840                 845
Glu Ala Gln Asn Trp Arg Val Thr Glu Ser Pro Lys Arg Val Tyr Val
850                 855                 860
Gly Arg Ser Ser Arg Asp Leu Pro Leu Ser Ser Gln Leu Glu
865                 870                 875

<210> SEQ ID NO 63
<211> LENGTH: 2583
<212> TYPE: DNA
<213> ORGANISM: Aspergillus niger

<400> SEQUENCE: 63
atgaggttca ctttgatcga ggcggtggct ctgactgccg tctcgctggc cagcgctgat         60
gaattggcct actccccacc gtattaccca tccccttggg ccaatggcca gggcgactgg        120
gcgcaggcat accagcgcgc tgttgatatt gtctcgcaaa tgacattgga tgagaaggtc        180

```
aatctgacca caggaactgg atgggaattg aactatgtg ttggtcgac tggcggtgtt      240 cccccgattgg gagttccggg aatgtgttta caggatagcc ctctgggcgt tcgcgactcc   300
gactacaact ctgctttccc tgccggcatg aacgtggctg caacctggga caagaatctg   360
gcataccttc gcggcaaggc tatgggtcag gaatttagtg acaaggggtgc cgatatccaa  420 ttgggtccag ctgccggccc tctcggtaga agtcccgacg gtggtcgtaa ctgggagggc   480
ttctccccag accctgccct aagtggtgtg ctctttgccg agaccatcaa gggtatccaa   540
gatgctggtg tggttgcgac ggctaagcac tacattgctt acgagcaaga gcatttccgt   600
caggcgcctg aagcccaagg ttttggattt aatatttccg agagtggaag tgcgaacctc   660
gatgataaga ctatgcacga gctgtacctc tggcccttcg cggatgccat ccgtgcaggt   720
gctggcgctg tgatgtgctc ctacaaccag atcaacaaca gttatggctg ccagaacagc   780
tacactctga caagctgct caaggccgag ctgggcttcc agggctttgt catgagtgat   840
tgggctgctc accatgctgg tgtgagtggt gctttggcag gattggatat gtctatgcca   900
ggagacgtcg actacgacag tggtacgtct tactggggta caaacttgac cattagcgtg   960
ctcaacggaa cggtgcccca atggcgtgtt gatgacatgg ctgtccgcat catggccgcc  1020
tactacaagg tcggccgtga ccgtctgtgg actcctccca acttcagctc atggaccaga  1080
gatgaatacg gctacaagta ctactacgtg tcggagggac cgtacgagaa ggtcaaccag  1140
tacgtgaatg tgcaacgcaa ccacagcgaa ctgattcgcc gcattggagc ggacagcacg  1200
gtgctcctca agaacgacgg cgctctgcct ttgactggta aggagcgcct ggtcgcgctt  1260
atcggagaag atgcgggctc caacccttat ggtgccaacg gctgcagtga ccgtggatgc  1320
gacaatggaa cattggcgat gggctgggga agtggtactg ccaacttccc ataccctggtg 1380 accccccgagc aggccatctc aaacgaggtg cttaagcaca gaatggtgt attcaccgcc   1440 accgataact gggctatcga tcagattgag gcgcttgcta agaccgccag tgtctctctt   1500
gtctttgtca cgccgactc tggtgagggt tacatcaatg tggacggaaa cctgggtgac   1560
cgcaggaacc tgaccctgtg gaggaacggc gataatgtga tcaaggctgc tgctagcaac   1620
tgcaacaaca caatcgttgt cattcactct gtcggaccag tcttggttaa cgagtggtac   1680 gacaaccccca atgttaccgc tatcctctgg ggtggtttgc ccggtcagga gtctggcaac  1740
tctcttgccg acgtcctcta tggccgtgtc aaccccggtg ccagtcgcc ctttacctgg    1800 ggcaagactc gtgaggccta ccaagactac ttggtcaccg agcccaacaa cggcaacgga   1860 gccccctcagg aagactttgt cgagggcgtc ttcattgact accgtggatt tgacaagcgc  1920
aacgagaccc cgatctacga gttcggctat ggtctgagct acaccacttt caactactcg   1980
aaccttgagg tgcaggtgct gagcgcccct gcatacgagc tgcttcgggg tgagaccgag   2040
gcagcgccaa ccttcggaga ggttggaaat gcgtcggatt acctctaccc cagcggattg   2100
cagagaatta ccaagttcat ctaccccctgg ctcaacggta ccgatctcga ggcatcttcc  2160
ggggatgcta gctacgggca ggactcctcc gactatcttc ccgagggagc caccgatggc  2220
tctgcgcaac cgatcctgcc tgccggtggc ggtcctggcg caacccctcg cctgtacgac  2280
gagctcatcc gcgtgtcagt gaccatcaag aacaccggca aggttgctgg tgatgaagtt   2340
ccccaactgt atgtttccct tggcggtccc aatgagccca agatcgtgct gcgtcaattc   2400
gagcgcatca cgctgcagcc gtcggaggag acgaagtgga gcacgactct gacgcgccgt   2460
gaccttgcaa actggaatgt tgagaagcag gactgggaga ttacgtcgta tcccaagatg   2520
```

```
gtgtttgtcg aagctcctc gcggaagctg ccgctccggg cgtctctgcc tactgttcac    2580
taa                                                                 2583
```

<210> SEQ ID NO 64
<211> LENGTH: 860
<212> TYPE: PRT
<213> ORGANISM: Aspergillus niger

<400> SEQUENCE: 64

```
Met Arg Phe Thr Leu Ile Glu Ala Val Ala Leu Thr Ala Val Ser Leu
1               5                   10                  15

Ala Ser Ala Asp Glu Leu Ala Tyr Ser Pro Pro Tyr Tyr Pro Ser Pro
            20                  25                  30

Trp Ala Asn Gly Gln Gly Asp Trp Ala Gln Ala Tyr Gln Arg Ala Val
        35                  40                  45

Asp Ile Val Ser Gln Met Thr Leu Asp Glu Lys Val Asn Leu Thr Thr
    50                  55                  60

Gly Thr Gly Trp Glu Leu Glu Leu Cys Val Gly Gln Thr Gly Gly Val
65                  70                  75                  80

Pro Arg Leu Gly Val Pro Gly Met Cys Leu Gln Asp Ser Pro Leu Gly
                85                  90                  95

Val Arg Asp Ser Asp Tyr Asn Ser Ala Phe Pro Ala Gly Met Asn Val
            100                 105                 110

Ala Ala Thr Trp Asp Lys Asn Leu Ala Tyr Leu Arg Gly Lys Ala Met
        115                 120                 125

Gly Gln Glu Phe Ser Asp Lys Gly Ala Asp Ile Gln Leu Gly Pro Ala
    130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Ser Gly Val Leu Phe Ala Glu Thr Ile
                165                 170                 175

Lys Gly Ile Gln Asp Ala Gly Val Val Ala Thr Ala Lys His Tyr Ile
            180                 185                 190

Ala Tyr Glu Gln Glu His Phe Arg Gln Ala Pro Glu Ala Gln Gly Phe
        195                 200                 205

Gly Phe Asn Ile Ser Glu Ser Gly Ser Ala Asn Leu Asp Asp Lys Thr
    210                 215                 220

Met His Glu Leu Tyr Leu Trp Pro Phe Ala Asp Ala Ile Arg Ala Gly
225                 230                 235                 240

Ala Gly Ala Val Met Cys Ser Tyr Asn Gln Ile Asn Asn Ser Tyr Gly
                245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Ala Ala His His Ala Gly Val
        275                 280                 285

Ser Gly Ala Leu Ala Gly Leu Asp Met Ser Met Pro Gly Asp Val Asp
    290                 295                 300

Tyr Asp Ser Gly Thr Ser Tyr Trp Gly Thr Asn Leu Thr Ile Ser Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Trp Thr Pro
            340                 345                 350

Pro Asn Phe Ser Ser Trp Thr Arg Asp Glu Tyr Gly Tyr Lys Tyr Tyr
```

-continued

```
            355                 360                 365
Tyr Val Ser Glu Gly Pro Tyr Glu Lys Val Asn Gln Tyr Val Asn Val
        370                 375                 380
Gln Arg Asn His Ser Glu Leu Ile Arg Arg Ile Gly Ala Asp Ser Thr
385                 390                 395                 400
Val Leu Leu Lys Asn Asp Gly Ala Leu Pro Leu Thr Gly Lys Glu Arg
                405                 410                 415
Leu Val Ala Leu Ile Gly Glu Asp Ala Gly Ser Asn Pro Tyr Gly Ala
            420                 425                 430
Asn Gly Cys Ser Asp Arg Gly Cys Asp Asn Gly Thr Leu Ala Met Gly
            435                 440                 445
Trp Gly Ser Gly Thr Ala Asn Phe Pro Tyr Leu Val Thr Pro Glu Gln
            450                 455                 460
Ala Ile Ser Asn Glu Val Leu Lys His Lys Asn Gly Val Phe Thr Ala
465                 470                 475                 480
Thr Asp Asn Trp Ala Ile Asp Gln Ile Glu Ala Leu Ala Lys Thr Ala
                485                 490                 495
Ser Val Ser Leu Val Phe Val Asn Ala Asp Ser Gly Glu Gly Tyr Ile
            500                 505                 510
Asn Val Asp Gly Asn Leu Gly Asp Arg Arg Asn Leu Thr Leu Trp Arg
            515                 520                 525
Asn Gly Asp Asn Val Ile Lys Ala Ala Ser Asn Cys Asn Asn Thr
            530                 535                 540
Ile Val Val Ile His Ser Val Gly Pro Val Leu Val Asn Glu Trp Tyr
545                 550                 555                 560
Asp Asn Pro Asn Val Thr Ala Ile Leu Trp Gly Leu Pro Gly Gln
                565                 570                 575
Glu Ser Gly Asn Ser Leu Ala Asp Val Leu Tyr Gly Arg Val Asn Pro
            580                 585                 590
Gly Ala Lys Ser Pro Phe Thr Trp Gly Lys Thr Arg Glu Ala Tyr Gln
            595                 600                 605
Asp Tyr Leu Val Thr Glu Pro Asn Asn Gly Asn Gly Ala Pro Gln Glu
            610                 615                 620
Asp Phe Val Glu Gly Val Phe Ile Asp Tyr Arg Gly Phe Asp Lys Arg
625                 630                 635                 640
Asn Glu Thr Pro Ile Tyr Glu Phe Gly Tyr Gly Leu Ser Tyr Thr Thr
                645                 650                 655
Phe Asn Tyr Ser Asn Leu Glu Val Gln Val Leu Ser Ala Pro Ala Tyr
            660                 665                 670
Glu Pro Ala Ser Gly Glu Thr Glu Ala Ala Pro Thr Phe Gly Glu Val
            675                 680                 685
Gly Asn Ala Ser Asp Tyr Leu Tyr Pro Ser Gly Leu Gln Arg Ile Thr
            690                 695                 700
Lys Phe Ile Tyr Pro Trp Leu Asn Gly Thr Asp Leu Glu Ala Ser Ser
705                 710                 715                 720
Gly Asp Ala Ser Tyr Gly Gln Asp Ser Ser Asp Tyr Leu Pro Glu Gly
                725                 730                 735
Ala Thr Asp Gly Ser Ala Gln Pro Ile Leu Pro Ala Gly Gly Gly Pro
            740                 745                 750
Gly Gly Asn Pro Arg Leu Tyr Asp Glu Leu Ile Arg Val Ser Val Thr
            755                 760                 765
Ile Lys Asn Thr Gly Lys Val Ala Gly Asp Glu Val Pro Gln Leu Tyr
770                 775                 780
```

```
Val Ser Leu Gly Gly Pro Asn Glu Pro Lys Ile Val Leu Arg Gln Phe
785                 790                 795                 800

Glu Arg Ile Thr Leu Gln Pro Ser Glu Glu Thr Lys Trp Ser Thr Thr
                805                 810                 815

Leu Thr Arg Arg Asp Leu Ala Asn Trp Asn Val Glu Lys Gln Asp Trp
        820                 825                 830

Glu Ile Thr Ser Tyr Pro Lys Met Val Phe Val Gly Ser Ser Ser Arg
            835                 840                 845

Lys Leu Pro Leu Arg Ala Ser Leu Pro Thr Val His
        850                 855                 860

<210> SEQ ID NO 65
<211> LENGTH: 2583
<212> TYPE: DNA
<213> ORGANISM: Aspergillus aculeatus

<400> SEQUENCE: 65
```

| | | | | | |
|---|---|---|---|---|---|
| atgaagctca | gttggcttga | ggcggctgcc | ttgacggctg | cttcagtcgt | cagcgctgat | 60 |
| gaactggcgt | tctctcctcc | tttctacccc | tctccgtggg | ccaatggcca | gggagagtgg | 120 |
| gcggaagcct | accagcgtgc | agtggccatt | gtatcccaga | tgactctgga | tgagaaggtc | 180 |
| aacctgacca | ccggaactgg | atgggagctg | agaagtgcg | tcggtcagac | tggtggtgtc | 240 |
| ccaagactga | acatcggtgg | catgtgtctt | caggacagtc | cctgggaat | cgtgatagt | 300 |
| gactacaatt | cggctttccc | tgctggtgtc | aacgttgctg | cgacatggga | caagaacctt | 360 |
| gcttatctac | gtggtcaggc | tatgggtcaa | gagttcagtg | acaaaggaat | tgatgttcaa | 420 |
| ttgggaccgg | ccgcgggtcc | cctcggcagg | agccctgatg | gaggtcgcaa | ctgggaaggt | 480 |
| ttctctccag | acccggctct | tactggtgtg | ctctttgcgg | agacgattaa | gggtattcaa | 540 |
| gacgctggtg | tcgtggcgac | agccaagcat | tacattctca | atgagcaaga | gcatttccgc | 600 |
| caggtcgcag | aggctgcggg | ctacggattc | aatatctccg | cacgatcag | ctctaacgtt | 660 |
| gatgacaaga | ccattcatga | aatgtacctc | tggcccttcg | cggatgccgt | tcgcgccggc | 720 |
| gttggcgcca | tcatgtgttc | ctacaaccag | atcaacaaca | gctacggttg | ccagaacagt | 780 |
| tacactctga | caaagcttct | gaaggccgag | ctcggcttcc | agggctttgt | gatgtctgac | 840 |
| tggggtgctc | accacagtgg | tgttggctct | gctttggccg | gcttggatat | gtcaatgcct | 900 |
| ggcgatatca | ccttcgattc | tgccactagt | ttctggggta | ccaacctgac | cattgctgtg | 960 |
| ctcaacggta | ccgtcccgca | gtggcgcgtt | gacgacatgg | ctgtccgtat | catggctgcc | 1020 |
| tactacaagg | ttggccgcga | ccgcctgtac | cagccgccta | acttcagctc | ctggactcgc | 1080 |
| gatgaatacg | gcttcaagta | tttctacccc | caggaagggc | cctatgagaa | ggtcaatcac | 1140 |
| tttgtcaatg | tgcagcgcaa | ccacagcgag | gttattcgca | agtgggagc | agacagtact | 1200 |
| gttctactga | gaacaacaa | tgccctgccg | ctgaccggaa | aggagcgcaa | agttgcgatc | 1260 |
| ctgggtgaag | atgctggatc | caactcgtac | ggtgccaatg | ctgctctga | ccgtggctgt | 1320 |
| gacaacggta | tcttgctat | ggcttggggt | agcggcactg | ccgaattccc | atatctcgtg | 1380 |
| accccctgagc | aggctattca | agccgaggtg | ctcaagcata | agggcagcgt | ctacgccatc | 1440 |
| acggacaact | gggcgctgag | ccaggtggag | accctcgcta | acaagccag | tgtctctctt | 1500 |
| gtatttgtca | actcggacgc | gggagagggc | tatatctccg | tggacggaaa | cgagggcgac | 1560 |
| cgcaacaacc | tcaccctctg | gaagaacggc | gacaacctca | tcaaggctgc | tgcaaacaac | 1620 |
| tgcaacaaca | ccatcgttgt | catccactcc | gttggacctg | ttttggttga | cgagtggtat | 1680 |

-continued

```
gaccacccca acgttactgc catcctctgg gcgggcttgc ctggccagga gtctggcaac   1740
tccttggctg acgtgctcta cggccgcgtc aacccgggcg ccaaatctcc attcacctgg   1800
ggcaagacga gggaggcgta cggggattac cttgtccgtg agctcaacaa cggcaacgga   1860
gctccccaag atgatttctc ggaaggtgtt ttcattgact accgcggatt cgacaagcgc   1920
aatgagaccc cgatctacga gttcggacat ggtctgagct acaccacttt caactactct   1980
ggccttcaca tccaggttct caacgcttcc tccaacgctc aagtagccac tgagactggc   2040
gccgctccca ccttcggaca gtcggcaat gcctctgact acgtgtaccc tgagggattg    2100
accagaatca gcaagttcat ctatccctgg cttaattcca cagacctgaa ggcctcatct    2160
ggcgacccgt actatggagt cgacaccgcg gagcacgtgc ccgagggtgc tactgatggc    2220
tctccgcagc ccgttctgcc tgccggtggt ggctctggtg gtaacccgcg cctctacgat    2280
gagttgatcc gtgtttcggt gacagtcaag aacactggtc gtgttgccgg tgatgctgtg    2340
cctcaattgt atgtttccct tggtggaccc aatgagccca aggttgtgtt gcgcaaattc    2400
gaccgcctca ccctcaagcc ctccgaggag acggtgtgga cgactaccct gacccgccgc    2460
gatctgtcta actgggacgt tgcggctcag gactgggtca tcacttctta cccgaagaag    2520
gtccatgttg gtagctcttc gcgtcagctg ccccttcacg cggcgctccc gaaggtgcaa    2580
tga                                                                 2583
```

<210> SEQ ID NO 66
<211> LENGTH: 860
<212> TYPE: PRT
<213> ORGANISM: Aspergillus aculeatus

<400> SEQUENCE: 66

```
Met Lys Leu Ser Trp Leu Glu Ala Ala Ala Leu Thr Ala Ala Ser Val
1               5                   10                  15

Val Ser Ala Asp Glu Leu Ala Phe Ser Pro Pro Phe Tyr Pro Ser Pro
            20                  25                  30

Trp Ala Asn Gly Gln Gly Glu Trp Ala Glu Ala Tyr Gln Arg Ala Val
        35                  40                  45

Ala Ile Val Ser Gln Met Thr Leu Asp Glu Lys Val Asn Leu Thr Thr
    50                  55                  60

Gly Thr Gly Trp Glu Leu Glu Lys Cys Val Gly Gln Thr Gly Gly Val
65                  70                  75                  80

Pro Arg Leu Asn Ile Gly Gly Met Cys Leu Gln Asp Ser Pro Leu Gly
                85                  90                  95

Ile Arg Asp Ser Asp Tyr Asn Ser Ala Phe Pro Ala Gly Val Asn Val
            100                 105                 110

Ala Ala Thr Trp Asp Lys Asn Leu Ala Tyr Leu Arg Gly Gln Ala Met
        115                 120                 125

Gly Gln Glu Phe Ser Asp Lys Gly Ile Asp Val Gln Leu Gly Pro Ala
    130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Thr Gly Val Leu Phe Ala Glu Thr Ile
                165                 170                 175

Lys Gly Ile Gln Asp Ala Gly Val Val Ala Thr Ala Lys His Tyr Ile
            180                 185                 190

Leu Asn Glu Gln Glu His Phe Arg Gln Val Ala Glu Ala Gly Tyr
            195                 200                 205
```

-continued

Gly Phe Asn Ile Ser Asp Thr Ile Ser Ser Asn Val Asp Asp Lys Thr
    210                 215                 220

Ile His Glu Met Tyr Leu Trp Pro Phe Ala Asp Ala Val Arg Ala Gly
225                 230                 235                 240

Val Gly Ala Ile Met Cys Ser Tyr Asn Gln Ile Asn Asn Ser Tyr Gly
            245                 250                 255

Cys Gln Asn Ser Tyr Thr Leu Asn Lys Leu Leu Lys Ala Glu Leu Gly
        260                 265                 270

Phe Gln Gly Phe Val Met Ser Asp Trp Gly Ala His His Ser Gly Val
    275                 280                 285

Gly Ser Ala Leu Ala Gly Leu Asp Met Ser Met Pro Gly Asp Ile Thr
290                 295                 300

Phe Asp Ser Ala Thr Ser Phe Trp Gly Thr Asn Leu Thr Ile Ala Val
305                 310                 315                 320

Leu Asn Gly Thr Val Pro Gln Trp Arg Val Asp Asp Met Ala Val Arg
            325                 330                 335

Ile Met Ala Ala Tyr Tyr Lys Val Gly Arg Asp Arg Leu Tyr Gln Pro
        340                 345                 350

Pro Asn Phe Ser Ser Trp Thr Arg Asp Glu Tyr Gly Phe Lys Tyr Phe
    355                 360                 365

Tyr Pro Gln Glu Gly Pro Tyr Glu Lys Val Asn His Phe Val Asn Val
370                 375                 380

Gln Arg Asn His Ser Glu Val Ile Arg Lys Leu Gly Ala Asp Ser Thr
385                 390                 395                 400

Val Leu Leu Lys Asn Asn Asn Ala Leu Pro Leu Thr Gly Lys Glu Arg
            405                 410                 415

Lys Val Ala Ile Leu Gly Glu Asp Ala Gly Ser Asn Ser Tyr Gly Ala
        420                 425                 430

Asn Gly Cys Ser Asp Arg Gly Cys Asp Asn Gly Thr Leu Ala Met Ala
    435                 440                 445

Trp Gly Ser Gly Thr Ala Glu Phe Pro Tyr Leu Val Thr Pro Glu Gln
450                 455                 460

Ala Ile Gln Ala Glu Val Leu Lys His Lys Gly Ser Val Tyr Ala Ile
465                 470                 475                 480

Thr Asp Asn Trp Ala Leu Ser Gln Val Glu Thr Leu Ala Lys Gln Ala
            485                 490                 495

Ser Val Ser Leu Val Phe Val Asn Ser Asp Ala Gly Glu Gly Tyr Ile
        500                 505                 510

Ser Val Asp Gly Asn Glu Gly Asp Arg Asn Asn Leu Thr Leu Trp Lys
    515                 520                 525

Asn Gly Asp Asn Leu Ile Lys Ala Ala Ala Asn Cys Asn Asn Thr
530                 535                 540

Ile Val Val Ile His Ser Val Gly Pro Val Leu Val Asp Glu Trp Tyr
545                 550                 555                 560

Asp His Pro Asn Val Thr Ala Ile Leu Trp Ala Gly Leu Pro Gly Gln
            565                 570                 575

Glu Ser Gly Asn Ser Leu Ala Asp Val Leu Tyr Gly Arg Val Asn Pro
        580                 585                 590

Gly Ala Lys Ser Pro Phe Thr Trp Gly Lys Thr Arg Glu Ala Tyr Gly
    595                 600                 605

Asp Tyr Leu Val Arg Glu Leu Asn Asn Gly Asn Gly Ala Pro Gln Asp
610                 615                 620

Asp Phe Ser Glu Gly Val Phe Ile Asp Tyr Arg Gly Phe Asp Lys Arg
625                 630                 635                 640

Asn Glu Thr Pro Ile Tyr Glu Phe Gly His Gly Leu Ser Tyr Thr Thr
            645                 650                 655

Phe Asn Tyr Ser Gly Leu His Ile Gln Val Leu Asn Ala Ser Ser Asn
        660                 665                 670

Ala Gln Val Ala Thr Glu Thr Gly Ala Ala Pro Thr Phe Gly Gln Val
    675                 680                 685

Gly Asn Ala Ser Asp Tyr Val Tyr Pro Glu Gly Leu Thr Arg Ile Ser
690                 695                 700

Lys Phe Ile Tyr Pro Trp Leu Asn Ser Thr Asp Leu Lys Ala Ser Ser
705                 710                 715                 720

Gly Asp Pro Tyr Tyr Gly Val Asp Thr Ala Glu His Val Pro Glu Gly
            725                 730                 735

Ala Thr Asp Gly Ser Pro Gln Pro Val Leu Pro Ala Gly Gly Gly Ser
        740                 745                 750

Gly Gly Asn Pro Arg Leu Tyr Asp Glu Leu Ile Arg Val Ser Val Thr
    755                 760                 765

Val Lys Asn Thr Gly Arg Val Ala Gly Asp Ala Val Pro Gln Leu Tyr
770                 775                 780

Val Ser Leu Gly Gly Pro Asn Glu Pro Lys Val Val Leu Arg Lys Phe
785                 790                 795                 800

Asp Arg Leu Thr Leu Lys Pro Ser Glu Glu Thr Val Trp Thr Thr Thr
            805                 810                 815

Leu Thr Arg Arg Asp Leu Ser Asn Trp Asp Val Ala Ala Gln Asp Trp
        820                 825                 830

Val Ile Thr Ser Tyr Pro Lys Lys Val His Val Gly Ser Ser Ser Arg
    835                 840                 845

Gln Leu Pro Leu His Ala Ala Leu Pro Lys Val Gln
850                 855                 860

<210> SEQ ID NO 67
<211> LENGTH: 3294
<212> TYPE: DNA
<213> ORGANISM: Aspergillus oryzae

<400> SEQUENCE: 67
atgcgttcct cccccctcct ccgctccgcc gttgtggccg ccctgccggt gttggccctt      60
gccgctgatg caggtccacc ccgctactgg gactgctgca agccttcgtg cggctgggcc     120
aagaaggctc ccgtgaacca gcctgtcttt cctgcaacg ccaacttcca gcgtatcacg      180
gacttcgacg ccaagtccgg ctgcgagccg ggcggtgtcg cctactcgtg cgccgaccag     240
acccatgggc tgtgaacga cgacttcgcg ctcggttttg ctgccaccct tattgccggc      300
agcaatgagg cgggctggtg ctgcgcctgc tacgagctca ccttcacatc cggtcctgtt     360
gctggcaaga gatggtcgt ccagtccacc agcactggcg gtgatcttgg cagcaaccac      420
ttcgatctca acatccccgg cggcggcgtc ggcatcttcg acggatgcac tccccagttc     480
ggtggtctgc ccggccagcg ctacggcggc atctcgtccc gcaacgagtg cgatcggttc     540
cccgacgccc tcaagcccgg ctgctactgg cgcttcgact ggttcaagaa cgccgacaat     600
ccgagcttca gcttccgtca ggtccagtgc ccagccgagc tcgtcgctcg caccggatgc     660
cgccgcaacg acgacggcaa cttccctgcc gtccagatcc ccatgcgttc ctcccccctc     720
ctccgctccg ccgttgtggc cgccctgccg gtgttggccc ttgccaagga tgatctcgcg     780

```
tactcccctc ctttctaccc ttccccatgg gcagatggtc agggtgaatg ggcggaagta      840
tacaaacgcg ctgtagacat agtttcccag atgacgttga cagagaaagt caacttaacg      900
actggaacag gatggcaact agagaggtgt gttggacaaa ctggcagtgt tcccagactc      960
aacatcccca gcttgtgttt gcaggatagt cctcttggta ttcgtttctc ggactacaat     1020
tcagctttcc ctgcgggtgt taatgtcgct gccacctggg acaagacgct cgcctacctt     1080
cgtggtcagg caatgggtga ggagttcagt gataagggta ttgacgttca gctgggtcct     1140
gctgctggcc ctctcggtgc tcatccggat ggcggtagaa actgggaagg tttctcacca     1200
gatccagccc tcaccggtgt acttttttgcg gagacgatta agggtattca agatgctggt     1260
gtcattgcga cagctaagca ttatatcatg aacgaacaag agcatttccg ccaacaaccc     1320
gaggctgcgg gttacggatt caacgtaagc gacagtttga gttccaacgt tgatgacaag     1380
actatgcatg aattgtacct ctggcccttc gcggatgcag tacgcgctgg agtcggtgct     1440
gtcatgtgct cttacaacca aatcaacaac agctacggtt gcgagaatag cgaaactctg     1500
aacaagcttt tgaaggcgga gcttggtttc caaggcttcg tcatgagtga ttggaccgct     1560
catcacagcg gcgtaggcgc tgctttagca ggtctggata tgtcgatgcc cggtgatgtt     1620
accttcgata gtggtacgtc tttctggggt gcaaacttga cggtcggtgt ccttaacggt     1680
acaatccccc aatggcgtgt tgatgacatg gctgtccgta tcatggccgc ttattacaag     1740
gttggccgcg acaccaaata cacccctccc aacttcagct cgtggaccag ggacgaatat     1800
ggtttcgcgc ataaccatgt ttcggaaggt gcttacgaga gggtcaacga attcgtggac     1860
gtgcaacgcg atcatgccga cctaatccgt cgcatcggcg cgcagagcac tgttctgctg     1920
aagaacaagg gtgccttgcc cttgagccgc aaggaaaagc tggtcgccct tctgggagag     1980
gatgcgggtt ccaactcgtg gggcgctaac ggctgtgatg accgtggttg cgataacggt     2040
acccttgcca tggcctgggg tagcggtact gcgaatttcc catacctcgt gacaccagag     2100
caggcgattc agaacgaagt tcttcagggc cgtggtaatg tcttcgccgt gaccgacagt     2160
tgggcgctcg acaagatcgc tgcggctgcc cgccaggcca gcgtatctct cgtgttcgtc     2220
aactccgact caggagaagg ctatcttagt gtggatggaa atgagggcga tcgtaacaac     2280
atcactctgt ggaagaacgg cgacaatgtg gtcaagaccg cagcgaataa ctgtaacaac     2340
accgttgtca tcatccactc cgtcggacca gttttgatcg atgaatggta tgaccacccc     2400
aatgtcactg gtattctctg ggctggtctg ccaggccagg agtctggtaa ctccattgcc     2460
gatgtgctgt acggtcgtgt caaccctggc gccaagtctc ctttcacttg gggcaagacc     2520
cgggagtcgt atggttctcc cttggtcaag gatgccaaca atggcaacgg agcgccccag     2580
tctgatttca cccagggtgt tttcatcgat taccgccatt tcgataagtt caatgagacc     2640
cctatctacg agtttggcta cggcttgagc tacaccacct tcgagctctc cgacctccat     2700
gttcagcccc tgaacgcgtc ccgatacact cccaccagtg gcatgactga agctgcaaag     2760
aactttggtg aaattggcga tgcgtcggag tacgtgtatc cggaggggct ggaaaggatc     2820
catgagttta tctatccctg gatcaactct accgacctga aggcatcgtc tgacgattct     2880
aactacggct gggaagactc caagtatatt cccgaaggcg ccacggatgg gtctgcccag     2940
ccccgtttgc ccgctagtgg tggtgccgga ggaaacccccg gtctgtacga ggatcttttc     3000
cgcgtctctg tgaaggtcaa gaacacgggc aatgtcgccg gtgatgaagt tcctcagctg     3060
tacgtttccc taggcggccc gaatgagccc aaggtggtac tgcgcaagtt tgagcgtatt     3120
cacttggccc cttcgcagga ggccgtgtgg acaacgaccc ttacccgtcg tgaccttgca     3180
```

-continued

```
aactgggacg tttcggctca ggactggacc gtcactcctt accccaagac gatctacgtt    3240
ggaaactcct cacggaaact gccgctccag gcctcgctgc ctaaggccca gtaa          3294
```

<210> SEQ ID NO 68
<211> LENGTH: 1097
<212> TYPE: PRT
<213> ORGANISM: Aspergillus oryzae

<400> SEQUENCE: 68

```
Met Arg Ser Ser Pro Leu Leu Arg Ser Ala Val Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Met Arg Ser Ser Pro Leu
225                 230                 235                 240

Leu Arg Ser Ala Val Val Ala Ala Leu Pro Val Leu Ala Leu Ala Lys
                245                 250                 255

Asp Asp Leu Ala Tyr Ser Pro Pro Phe Tyr Pro Ser Pro Trp Ala Asp
            260                 265                 270

Gly Gln Gly Glu Trp Ala Glu Val Tyr Lys Arg Ala Val Asp Ile Val
        275                 280                 285

Ser Gln Met Thr Leu Thr Glu Lys Val Asn Leu Thr Thr Gly Thr Gly
    290                 295                 300

Trp Gln Leu Glu Arg Cys Val Gly Gln Thr Gly Ser Val Pro Arg Leu
305                 310                 315                 320

Asn Ile Pro Ser Leu Cys Leu Gln Asp Ser Pro Leu Gly Ile Arg Phe
                325                 330                 335

Ser Asp Tyr Asn Ser Ala Phe Pro Ala Gly Val Asn Val Ala Ala Thr
            340                 345                 350
```

```
Trp Asp Lys Thr Leu Ala Tyr Leu Arg Gly Gln Ala Met Gly Glu Glu
            355                 360                 365

Phe Ser Asp Lys Gly Ile Asp Val Gln Leu Gly Pro Ala Ala Gly Pro
        370                 375                 380

Leu Gly Ala His Pro Asp Gly Arg Asn Trp Glu Gly Phe Ser Pro
385                 390                 395                 400

Asp Pro Ala Leu Thr Gly Val Leu Phe Ala Glu Thr Ile Lys Gly Ile
                405                 410                 415

Gln Asp Ala Gly Val Ile Ala Thr Ala Lys His Tyr Ile Met Asn Glu
            420                 425                 430

Gln Glu His Phe Arg Gln Gln Pro Glu Ala Ala Gly Tyr Gly Phe Asn
        435                 440                 445

Val Ser Asp Ser Leu Ser Ser Asn Val Asp Asp Lys Thr Met His Glu
    450                 455                 460

Leu Tyr Leu Trp Pro Phe Ala Asp Ala Val Arg Ala Gly Val Gly Ala
465                 470                 475                 480

Val Met Cys Ser Tyr Asn Gln Ile Asn Asn Ser Tyr Gly Cys Glu Asn
                485                 490                 495

Ser Glu Thr Leu Asn Lys Leu Leu Lys Ala Glu Leu Gly Phe Gln Gly
            500                 505                 510

Phe Val Met Ser Asp Trp Thr Ala His His Ser Gly Val Gly Ala Ala
        515                 520                 525

Leu Ala Gly Leu Asp Met Ser Met Pro Gly Asp Val Thr Phe Asp Ser
    530                 535                 540

Gly Thr Ser Phe Trp Gly Ala Asn Leu Thr Val Gly Val Leu Asn Gly
545                 550                 555                 560

Thr Ile Pro Gln Trp Arg Val Asp Asp Met Ala Val Arg Ile Met Ala
                565                 570                 575

Ala Tyr Tyr Lys Val Gly Arg Asp Thr Lys Tyr Thr Pro Pro Asn Phe
            580                 585                 590

Ser Ser Trp Thr Arg Asp Glu Tyr Gly Phe Ala His Asn His Val Ser
        595                 600                 605

Glu Gly Ala Tyr Glu Arg Val Asn Glu Phe Val Asp Val Gln Arg Asp
    610                 615                 620

His Ala Asp Leu Ile Arg Arg Ile Gly Ala Gln Ser Thr Val Leu Leu
625                 630                 635                 640

Lys Asn Lys Gly Ala Leu Pro Leu Ser Arg Lys Glu Lys Leu Val Ala
                645                 650                 655

Leu Leu Gly Glu Asp Ala Gly Ser Asn Ser Trp Gly Ala Asn Gly Cys
            660                 665                 670

Asp Asp Arg Gly Cys Asp Asn Gly Thr Leu Ala Met Ala Trp Gly Ser
        675                 680                 685

Gly Thr Ala Asn Phe Pro Tyr Leu Val Thr Pro Glu Gln Ala Ile Gln
    690                 695                 700

Asn Glu Val Leu Gln Gly Arg Gly Asn Val Phe Ala Val Thr Asp Ser
705                 710                 715                 720

Trp Ala Leu Asp Lys Ile Ala Ala Ala Arg Gln Ala Ser Val Ser
                725                 730                 735

Leu Val Phe Val Asn Ser Asp Ser Gly Glu Gly Tyr Leu Ser Val Asp
            740                 745                 750

Gly Asn Glu Gly Asp Arg Asn Asn Ile Thr Leu Trp Lys Asn Gly Asp
        755                 760                 765

Asn Val Val Lys Thr Ala Ala Asn Cys Asn Asn Thr Val Val Ile
```

```
                770             775             780
Ile His Ser Val Gly Pro Val Leu Ile Asp Glu Trp Tyr Asp His Pro
785             790             795             800

Asn Val Thr Gly Ile Leu Trp Ala Gly Leu Pro Gly Gln Glu Ser Gly
                805             810             815

Asn Ser Ile Ala Asp Val Leu Tyr Gly Arg Val Asn Pro Gly Ala Lys
                820             825             830

Ser Pro Phe Thr Trp Gly Lys Thr Arg Glu Ser Tyr Gly Ser Pro Leu
                835             840             845

Val Lys Asp Ala Asn Asn Gly Asn Gly Ala Pro Gln Ser Asp Phe Thr
850             855             860

Gln Gly Val Phe Ile Asp Tyr Arg His Phe Asp Lys Phe Asn Glu Thr
865             870             875             880

Pro Ile Tyr Glu Phe Gly Tyr Gly Leu Ser Tyr Thr Thr Phe Glu Leu
                885             890             895

Ser Asp Leu His Val Gln Pro Leu Asn Ala Ser Arg Tyr Thr Pro Thr
                900             905             910

Ser Gly Met Thr Glu Ala Ala Lys Asn Phe Gly Glu Ile Gly Asp Ala
                915             920             925

Ser Glu Tyr Val Tyr Pro Glu Gly Leu Glu Arg Ile His Glu Phe Ile
                930             935             940

Tyr Pro Trp Ile Asn Ser Thr Asp Leu Lys Ala Ser Ser Asp Asp Ser
945             950             955             960

Asn Tyr Gly Trp Glu Asp Ser Lys Tyr Ile Pro Glu Gly Ala Thr Asp
                965             970             975

Gly Ser Ala Gln Pro Arg Leu Pro Ala Ser Gly Gly Ala Gly Gly Asn
                980             985             990

Pro Gly Leu Tyr Glu Asp Leu Phe Arg Val Ser Val Lys Val Lys Asn
                995             1000            1005

Thr Gly Asn Val Ala Gly Asp Glu Val Pro Gln Leu Tyr Val Ser
    1010            1015            1020

Leu Gly Gly Pro Asn Glu Pro Lys Val Val Leu Arg Lys Phe Glu
    1025            1030            1035

Arg Ile His Leu Ala Pro Ser Gln Glu Ala Val Trp Thr Thr Thr
    1040            1045            1050

Leu Thr Arg Arg Asp Leu Ala Asn Trp Asp Val Ser Ala Gln Asp
    1055            1060            1065

Trp Thr Val Thr Pro Tyr Pro Lys Thr Ile Tyr Val Gly Asn Ser
    1070            1075            1080

Ser Arg Lys Leu Pro Leu Gln Ala Ser Leu Pro Lys Ala Gln
    1085            1090            1095
```

<210> SEQ ID NO 69
<211> LENGTH: 3294
<212> TYPE: DNA
<213> ORGANISM: Aspergillus oryzae

<400> SEQUENCE: 69

```
atgcgttcct cccccctcct ccgctccgcc gttgtggccg ccctgccggt gttggccctt      60
gccgctgatg gcaggtccac ccgctactgg gactgctgca agccttcgtg cggctgggcc    120
aagaaggctc ccgtgaacca gcctgtcttt tcctgcaacg ccaacttcca gcgtatcacg    180
gacttcgacg ccaagtccgg ctgcgagccg ggcggtgtcg cctactcgtg cgccgaccag    240
accccatggg ctgtgaacga cgacttcgcg ctcggttttg ctgccacctc tattgccggc    300
```

```
agcaatgagg cgggctggtg ctgcgcctgc tacgagctca ccttcacatc cggtcctgtt    360
gctggcaaga agatggtcgt ccagtccacc agcactggcg gtgatcttgg cagcaaccac    420
ttcgatctca acatccccgg cggcggcgtc ggcatcttcg acggatgcac tccccagttc    480
ggtggtctgc ccgccagcg ctacggcggc atctcgtccc gcaacgagtg cgatcggttc    540
cccgacgccc tcaagcccgg ctgctactgg cgcttcgact ggttcaagaa cgccgacaat    600
ccgagcttca gcttccgtca ggtccagtgc ccagccgagc tcgtcgctcg caccggatgc    660
cgccgcaacg acgacggcaa cttccctgcc gtccagatcc ccatgcgttc ctccccctc    720
ctccgctccg ccgttgtggc cgccctgccg gtgttggccc ttgccaagga tgatctcgcg    780
tactcccctc ctttctaccc ttccccatgg gcagatggtc agggtgaatg gcggaagta    840
tacaaacgcg ctgtagacat agtttcccag atgacgttga cagagaaagt caacttaacg    900
actggaacag gatggcaact agagaggtgt gttggacaaa ctggcagtgt tcccagactc    960
aacatcccca gcttgtgttt gcaggatagt cctcttggta ttcgtttctc ggactacaat   1020
tcagctttcc ctgcgggtgt taatgtcgct gccacctggg acaagacgct cgcctacctt   1080
cgtggtcagg caatgggtga ggagttcagt gataagggta ttgacgttca gctgggtcct   1140
gctgctggcc ctctcggtgc tcatccggat ggcggtagaa actgggaaag tttctcacca   1200
gatccagccc tcaccggtgt actttttgcg gagacgatta agggtattca agatgctggt   1260
gtcattgcga cagctaagca ttatatcatg aacgaacaag agcatttccg ccaacaaccc   1320
gaggctgcgg gttacggatt caacgtaagc gacagtttga gttccaacgt tgatgacaag   1380
actatgcatg aattgtacct ctggcccttc gcggatgcag tacgcgctgg agtcggtgct   1440
gttatgtgct cttacaacca aatcaacaac agctacggtt gcgagaatag cgaaactctg   1500
aacaagcttt tgaaggcgga gcttggtttc caaggcttcg tcatgagtga ttggaccgct   1560
caacacagcg gcgtaggcgc tgctttagca ggtctggata tgtcgatgcc cggtgatgtt   1620
accttcgata gtggtacgtc tttctggggt gcaaacttga cggtcggtgt ccttaacggt   1680
acaatccccc aatggcgtgt tgatgacatg gctgtccgta tcatggccgc ttattacaag   1740
gttggccgcg acaccaaata cacccctccc aacttcagct cgtggaccag ggacgaatat   1800
ggtttcgcgc ataaccatgt ttcggaaggt gcttacgaga gggtcaacga attcgtggac   1860
gtgcaacgcg atcatgccga cctaatccgt cgcatcggcg cgcagagcac tgttctgctg   1920
aagaacaagg gtgccttgcc cttgagccgc aaggaaaagc tggtcgccct tctgggagag   1980
gatgcgggtt ccaactcgtg gggcgctaac ggctgtgatg accgtggttg cgataacggt   2040
acccttgcca tggcctgggg tagcggtact gcgaatttcc catacctcgt gacaccagag   2100
caggcgattc agaacgaagt tcttcagggc cgtggtaatg tcttcgccgt gaccgacagt   2160
tgggcgctcg acaagatcgc tgcggctgcc cgccaggcca gcgtatctct cgtgttcgtc   2220
aactccgact caggagaagg ctatcttagt gtggatggaa atgagggcga tcgtaacaac   2280
atcactctgt ggaagaacgg cgacaatgtg gtcaagaccg cagcgaataa ctgtaacaac   2340
accgttgtca tcatccactc cgtcggacca gttttgatcg atgaatggta tgaccacccc   2400
aatgtcactg gtattctctg ggctggtctg ccaggcaggg agtctggtaa ctccattgcc   2460
gatgtgctgt acgtcgtgt caaccctggc gccaagtctc ctttcacttg gggcaagacc   2520
cgggagtcgt atggttctcc cttggtcaag gatgccaaca atggcaacgg agcgccccag   2580
tctgatttca cccagggtgt tttcatcgat taccgccatt tcgataagtt caatgagacc   2640
```

```
cctatctacg agtttggcta cggcttgagc tacaccacct tcgagctctc cgacctccat    2700
gttcagcccc tgaacgcgtc ccgatacact cccaccagtg gcatgactga agctgcaaag    2760
aactttggtg aaattggcga tgcgtcggag tacgtgtatc cggaggggct ggaaaggatc    2820
catgagttta tctatccctg atcaactct  accgacctga aggcatcgtc tgacgattct    2880
aactacggct gggaagactc caagtatatt cccgaaggcg ccacggatgg gtctgcccag    2940
ccccgtttgc ccgctagtgg tggtgccgga ggaaaccccg gtctgtacga ggatcttttc    3000
cgcgtctctg tgaaggtcaa gaacacgggc aatgtcgccg gtgatgaagt tcctcagctg    3060
tacgtttccc taggcggccc gaatgagccc aaggtggtac tgcgcaagtt tgagcgtatt    3120
cacttggccc cttcgcagga ggccgtgtgg acaacgaccc ttacccgtcg tgaccttgca    3180
aactgggacg tttcggctca ggactggacc gtcactcctt accccaagac gatctacgtt    3240
ggaaactcct cacggaaact gccgctccag gcctcgctgc ctaaggccca gtaa          3294
```

<210> SEQ ID NO 70
<211> LENGTH: 1097
<212> TYPE: PRT
<213> ORGANISM: Aspergillus oryzae

<400> SEQUENCE: 70

```
Met Arg Ser Ser Pro Leu Leu Arg Ser Ala Val Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Met Arg Ser Ser Pro Leu
225                 230                 235                 240

Leu Arg Ser Ala Val Val Ala Ala Leu Pro Val Leu Ala Leu Ala Lys
                245                 250                 255

Asp Asp Leu Ala Tyr Ser Pro Pro Phe Tyr Pro Ser Pro Trp Ala Asp
```

```
                260                 265                 270
Gly Gln Gly Glu Trp Ala Glu Val Tyr Lys Arg Ala Val Asp Ile Val
            275                 280                 285

Ser Gln Met Thr Leu Thr Glu Lys Val Asn Leu Thr Thr Gly Thr Gly
        290                 295                 300

Trp Gln Leu Glu Arg Cys Val Gly Gln Thr Gly Ser Val Pro Arg Leu
305                 310                 315                 320

Asn Ile Pro Ser Leu Cys Leu Gln Asp Ser Pro Leu Gly Ile Arg Phe
                325                 330                 335

Ser Asp Tyr Asn Ser Ala Phe Pro Ala Gly Val Asn Val Ala Ala Thr
            340                 345                 350

Trp Asp Lys Thr Leu Ala Tyr Leu Arg Gly Gln Ala Met Gly Glu Glu
        355                 360                 365

Phe Ser Asp Lys Gly Ile Asp Val Gln Leu Gly Pro Ala Ala Gly Pro
370                 375                 380

Leu Gly Ala His Pro Asp Gly Arg Asn Trp Glu Ser Phe Ser Pro
385                 390                 395                 400

Asp Pro Ala Leu Thr Gly Val Leu Phe Ala Glu Thr Ile Lys Gly Ile
                405                 410                 415

Gln Asp Ala Gly Val Ile Ala Thr Ala Lys His Tyr Ile Met Asn Glu
            420                 425                 430

Gln Glu His Phe Arg Gln Gln Pro Glu Ala Ala Gly Tyr Gly Phe Asn
        435                 440                 445

Val Ser Asp Ser Leu Ser Ser Asn Val Asp Asp Lys Thr Met His Glu
450                 455                 460

Leu Tyr Leu Trp Pro Phe Ala Asp Ala Val Arg Ala Gly Val Gly Ala
465                 470                 475                 480

Val Met Cys Ser Tyr Asn Gln Ile Asn Asn Ser Tyr Gly Cys Glu Asn
                485                 490                 495

Ser Glu Thr Leu Asn Lys Leu Leu Lys Ala Glu Leu Gly Phe Gln Gly
            500                 505                 510

Phe Val Met Ser Asp Trp Thr Ala Gln His Ser Gly Val Gly Ala Ala
        515                 520                 525

Leu Ala Gly Leu Asp Met Ser Met Pro Gly Asp Val Thr Phe Asp Ser
530                 535                 540

Gly Thr Ser Phe Trp Gly Ala Asn Leu Thr Val Gly Val Leu Asn Gly
545                 550                 555                 560

Thr Ile Pro Gln Trp Arg Val Asp Asp Met Ala Val Arg Ile Met Ala
                565                 570                 575

Ala Tyr Tyr Lys Val Gly Arg Asp Thr Lys Tyr Thr Pro Pro Asn Phe
            580                 585                 590

Ser Ser Trp Thr Arg Asp Glu Tyr Gly Phe Ala His Asn His Val Ser
        595                 600                 605

Glu Gly Ala Tyr Glu Arg Val Asn Glu Phe Val Asp Val Gln Arg Asp
610                 615                 620

His Ala Asp Leu Ile Arg Arg Ile Gly Ala Gln Ser Thr Val Leu Leu
625                 630                 635                 640

Lys Asn Lys Gly Ala Leu Pro Leu Ser Arg Lys Glu Lys Leu Val Ala
                645                 650                 655

Leu Leu Gly Glu Asp Ala Gly Ser Asn Ser Trp Gly Ala Asn Gly Cys
            660                 665                 670

Asp Asp Arg Gly Cys Asp Asn Gly Thr Leu Ala Met Ala Trp Gly Ser
        675                 680                 685
```

```
Gly Thr Ala Asn Phe Pro Tyr Leu Val Thr Pro Glu Gln Ala Ile Gln
690             695                 700

Asn Glu Val Leu Gln Gly Arg Gly Asn Val Phe Ala Val Thr Asp Ser
705             710                 715                 720

Trp Ala Leu Asp Lys Ile Ala Ala Ala Arg Gln Ala Ser Val Ser
            725                 730                 735

Leu Val Phe Val Asn Ser Asp Ser Gly Glu Gly Tyr Leu Ser Val Asp
            740                 745                 750

Gly Asn Glu Gly Asp Arg Asn Asn Ile Thr Leu Trp Lys Asn Gly Asp
            755                 760             765

Asn Val Val Lys Thr Ala Ala Asn Asn Cys Asn Asn Thr Val Val Ile
        770             775                 780

Ile His Ser Val Gly Pro Val Leu Ile Asp Glu Trp Tyr Asp His Pro
785             790                 795                 800

Asn Val Thr Gly Ile Leu Trp Ala Gly Leu Pro Gly Gln Glu Ser Gly
                805                 810                 815

Asn Ser Ile Ala Asp Val Leu Tyr Gly Arg Val Asn Pro Gly Ala Lys
                820                 825                 830

Ser Pro Phe Thr Trp Gly Lys Thr Arg Glu Ser Tyr Gly Ser Pro Leu
        835                 840                 845

Val Lys Asp Ala Asn Asn Gly Asn Gly Ala Pro Gln Ser Asp Phe Thr
850                 855                 860

Gln Gly Val Phe Ile Asp Tyr Arg His Phe Asp Lys Phe Asn Glu Thr
865                 870                 875                 880

Pro Ile Tyr Glu Phe Gly Tyr Gly Leu Ser Tyr Thr Thr Phe Glu Leu
                885                 890                 895

Ser Asp Leu His Val Gln Pro Leu Asn Ala Ser Arg Tyr Thr Pro Thr
                900                 905                 910

Ser Gly Met Thr Glu Ala Ala Lys Asn Phe Gly Glu Ile Gly Asp Ala
        915                 920                 925

Ser Glu Tyr Val Tyr Pro Glu Gly Leu Glu Arg Ile His Glu Phe Ile
930                 935                 940

Tyr Pro Trp Ile Asn Ser Thr Asp Leu Lys Ala Ser Ser Asp Asp Ser
945                 950                 955                 960

Asn Tyr Gly Trp Glu Asp Ser Lys Tyr Ile Pro Glu Gly Ala Thr Asp
                965                 970                 975

Gly Ser Ala Gln Pro Arg Leu Pro Ala Ser Gly Gly Ala Gly Gly Asn
                980                 985                 990

Pro Gly Leu Tyr Glu Asp Leu Phe Arg Val Ser Val Lys Val Lys Asn
        995                 1000                1005

Thr Gly Asn Val Ala Gly Asp Glu Val Pro Gln Leu Tyr Val Ser
    1010                1015                1020

Leu Gly Gly Pro Asn Glu Pro Lys Val Val Leu Arg Lys Phe Glu
    1025                1030                1035

Arg Ile His Leu Ala Pro Ser Gln Glu Ala Val Trp Thr Thr Thr
    1040                1045                1050

Leu Thr Arg Arg Asp Leu Ala Asn Trp Asp Val Ser Ala Gln Asp
    1055                1060                1065

Trp Thr Val Thr Pro Tyr Pro Lys Thr Ile Tyr Val Gly Asn Ser
    1070                1075                1080

Ser Arg Lys Leu Pro Leu Gln Ala Ser Leu Pro Lys Ala Gln
    1085                1090                1095
```

What is claimed is:

1. A method for producing a fermentation product, comprising:
   (a) saccharifying a cellulosic material with an enzyme composition comprising one or more cellulolytic enzymes in the presence of a peroxide-generating system and a polypeptide having peroxidase activity to form a saccharified cellulosic material, wherein the presence of the polypeptide having peroxidase activity increases saccharification of the cellulosic material compared to the absence of the polypeptide having peroxidase activity;
   (b) fermenting the saccharified cellulosic material of step (a) with one or more fermenting microorganisms to produce the fermentation product; and
   (c) recovering the fermentation product from the fermentation.

2. The method of claim 1, wherein the one or more cellulolytic enzymes are selected from the group consisting of an endoglucanase, a cellobiohydrolase, and a beta-glucosidase.

3. The method of claim 1, wherein the enzyme composition further comprises a polypeptide having cellulolytic enhancing activity.

4. The method of claim 1, wherein the enzyme composition further comprises one or more enzymes selected from the group consisting of a hemicellulase, an esterase, a protease, and a laccase.

5. The method of claim 1, wherein the cellulosic material is pretreated.

6. The method of claim 1, wherein the saccharified cellulosic material is a sugar.

7. The method of claim 6, wherein the sugar is selected from the group consisting of glucose, xylose, mannose, galactose, and arabinose.

8. The method of claim 1, wherein the $K_m$ of the polypeptide having peroxidase activity is in the range of 0.0001 to 50 mM.

9. The method of claim 1, wherein the enzyme composition further comprises one or more enzymes selected from the group consisting of a xylanase, an acetyxylan esterase, a feruloyl esterase, an arabinofuranosidase, a xylosidase, a glucuronidase, and a combination thereof.

10. The method of claim 1, wherein the amount of a polypeptide having peroxidase activity to the cellulosic material is about 0.001 to about 50 mg per g of the cellulosic material.

11. The method of claim 1, wherein the enzyme composition comprises a peroxide-generating system.

12. The method of claim 11, wherein the fermentation product is an alcohol, an organic acid, a ketone, an amino acid, or a gas.

13. The method of claim 1, wherein the polypeptide having peroxidase activity is selected from the group consisting of: E.C. 1.11.1.1 NADH peroxidase, E.C. 1.11.1.2 NADPH peroxidase, E.C. 1.11.1.3 fatty acid peroxidase, E.C. 1.11.1.5 di-heme cytochrome c peroxidase, E.C. 1.11.1.5 cytochrome c peroxidase, E.C. 1.11.1.6 catalase, E.C. 1.11.1.6 manganese catalase, E.C. 1.11.1.7 invertebrate peroxinectin, E.C. 1.11.1.7 eosinophil peroxidase, E.C. 1.11.1.7 lactoperoxidase, E.C. 1.11.1.7 myeloperoxidase, E.C. 1.11.1.8 thyroid peroxidase, E.C. 1.11.1.9 glutathione peroxidase, E.C. 1.11.1.10 chloride peroxidase, E.C. 1.11.1.11 ascorbate peroxidase, E.C. 1.11.1.12 other glutathione peroxidase, E.C. 1.11.1.13 manganese peroxidase, E.C. 1.11.1.14 lignin peroxidase, E.C. 1.11.1.15 cysteine peroxiredoxin, E.C. 1.11.1.16 versatile peroxidase, E.C. 1.11.1.B2 chloride peroxidase, E.C. 1.11.1.B4 haloperoxidase, E.C. 1.11.1.84 no-heme vanadium haloperoxidase, E.C. 1.11.1.B6 iodide peroxidase, E.C. 1.11.1.87 bromide peroxidase, and E.C. 1.11.1.B8 iodide peroxidase.

14. The method of claim 1, wherein the polypeptide having peroxidase activity is selected from horseradish peroxidase and *Corprinus cinereus* peroxidase.

15. The method of claim 1, wherein the peroxide-generating system comprises a peroxide-generating enzyme.

16. The method of claim 1, wherein the peroxide-generating enzyme is selected from the group consisting of: E.C. 1.1.3.x-donor:oxygen oxidoreductase, glucose oxidase (E.C. 1.1.3.4), hexose oxidase (E.C. 1.1.3.5), aryl-alcohol oxidase (E.C. 1.1.3.7), D-arabinono-1,4-lactone oxidase (E.C. 1.1.3.37), vanillyl-alcohol oxidase (E.C. 1.1.3.38), xylitol oxidase (E.C. 1.1.3.41), E.C. 1.1.99.8-alcohol dehydrogenase, E.C. 1.1.99.18-cellobiose dehydrogenase, E.C. 1.2.3.x-aldehyde oxidase (E.C. 1.2.3.1), aryl-aldehyde oxidase (E.C. 1.2.3.9), E.C. 1.3.3.x-dihydroorotate oxidase (E.C. 1.3.3.1), pyrroloquinoline-quinone synthase (E.C. 1.3.3.11), E.C. 1.4.3.x-L-amino acid oxidase (E.C. 1.4.3.2), L-glutamate oxidase (E.C. 1.4.3.11), E.C. 1.5.3.x-polyamine oxidase (1.5.3.11), E.C. 1.6.3.1-NADPH oxidase, E.C. 1.7.3.x-urate oxidase (E.C. 1.7.3.3), hydroxylamine oxidase (E.C. 1.7.3.4), E.C. 1.8.3.x-thiol oxidase (E.C. 1.8.3.2), glutathione oxidase (E.C. 1.8.3.3), E.C. 1.9.3.1-cytochrome c oxidase, E.C. 1.13.11.12 lipoxygenase, E.C. 1.13.11.31 arachidonate 12-lipoxygenase, E.C. 1.13.11.33 arachidonate 15-lipoxygenase, E.C. 1.13.11.34 arachidonate 5-lipoxygenase, E.C. 1.13.11.40 arachidonate 8-lipoxygenase, E.C. 1.13.11.45 linoleate 11-lipoxygenase, E.C. 1.15.1.1-superoxide dismutase, and E.C. 1.17.3.x-xanthine oxidase (E.C. 1.17.3.2).

* * * * *